US012673957B2

(12) United States Patent
Kovacs

(10) Patent No.: US 12,673,957 B2
(45) Date of Patent: Jul. 7, 2026

(54) INHIBITION OF GLIAL CELL ACTIVATION

(71) Applicant: LAPKO INC, Las Vegas, NV (US)

(72) Inventor: Bruce Kovacs, Long Beach, CA (US)

(73) Assignee: LAPKO INC, Las Vegas, NV (US)

( * ) Notice: Subject to any disclaimer, the term of this patent is extended or adjusted under 35 U.S.C. 154(b) by 0 days.

(21) Appl. No.: 19/295,468

(22) Filed: Aug. 8, 2025

(65) Prior Publication Data

US 2026/0035380 A1 Feb. 5, 2026

Related U.S. Application Data

(63) Continuation of application No. PCT/US2025/039964, filed on Jul. 30, 2025.

(60) Provisional application No. 63/677,931, filed on Jul. 31, 2024.

(51) Int. Cl.

| | |
|---|---|
| ***C07D 491/056*** | (2006.01) |
| ***A61K 31/4025*** | (2006.01) |
| ***A61K 31/4035*** | (2006.01) |
| ***A61K 31/404*** | (2006.01) |
| ***A61K 31/407*** | (2006.01) |
| ***A61K 31/436*** | (2006.01) |
| ***A61K 31/437*** | (2006.01) |
| ***A61K 31/4439*** | (2006.01) |
| ***A61K 31/506*** | (2006.01) |
| ***A61K 31/519*** | (2006.01) |
| ***A61K 45/06*** | (2006.01) |
| ***A61P 25/00*** | (2006.01) |
| ***C07D 405/06*** | (2006.01) |
| ***C07D 405/10*** | (2006.01) |
| ***C07D 405/12*** | (2006.01) |
| ***C07D 405/14*** | (2006.01) |
| ***C07D 409/14*** | (2006.01) |
| ***C07D 411/06*** | (2006.01) |
| ***C07D 491/147*** | (2006.01) |
| ***C07D 493/04*** | (2006.01) |
| ***C07D 495/04*** | (2006.01) |

(52) U.S. Cl.

CPC ...... *C07D 491/056* (2013.01); *A61K 31/4025* (2013.01); *A61K 31/4035* (2013.01); *A61K 31/404* (2013.01); *A61K 31/407* (2013.01); *A61K 31/436* (2013.01); *A61K 31/437* (2013.01); *A61K 31/4439* (2013.01); *A61K 31/506* (2013.01); *A61K 31/519* (2013.01); *A61K 45/06* (2013.01); *A61P 25/00* (2018.01); *C07D 405/06* (2013.01); *C07D 405/10* (2013.01); *C07D 405/12* (2013.01); *C07D 405/14* (2013.01); *C07D 409/14* (2013.01); *C07D 411/06* (2013.01); *C07D 491/147* (2013.01); *C07D 493/04* (2013.01); *C07D 495/04* (2013.01)

(58) Field of Classification Search

CPC .............. C07D 491/056; C07D 405/06; C07D 405/10; C07D 405/12; C07D 405/14; C07D 409/14; C07D 411/06; C07D 491/147; C07D 493/04; C07D 495/04; A61P 25/00; A61K 31/4025; A61K 31/4035; A61K 31/404; A61K 31/407; A61K 31/436; A61K 31/437; A61K 31/4439; A61K 31/506; A61K 31/519

See application file for complete search history.

(56) References Cited

PUBLICATIONS

Wang, "Synthesis and evaluation of 3-aryl piperidine analogs as potent and efficacious dopamine D4 receptor agonists", Bioorganic & Medicinal Chemistry 13 (2005) 4667-4678.*
Abraham et al, "Burger's Medicinal Chemistry, Drug Discovery and Development" Wiley, 2010. 7th Edition.
Allen NJ et al, "Glia as architects of central nervous system formation and function," Science. 2018. 362 (6411):181-185.
Blicke FF, "The Mannich Reaction". Organic Reactions. 2011. 1(10): 303-341.
Hanessian et al, "Design and Strategy in Organic Synthesis" Wiley-VCH, 2013. 1st Edition. (Abstract).
Ho TL, "Fiesers' Reagents for Organic Synthesis" Wiley, 2013. vol. 27 Edition.
Lan et al, "Modulators of microglial activation and polarization after intracerebral hemorrhage," Nat Rev Neurol. 2017. 7:420-433.
Lee et al, "New advances on glial activation in health and disease," World J Virol. 2015. 4(2):42-55.
Lemke et al, "Foye's Principles of Medicinal Chemistry" Wiley, 2013. 7th Edition.
Purves D, et al, "Neuroglial Cells," Neuroscience. 2nd edition. Sunderland (MA): Sinauer Associates; 2001. pp. 1-3.
Salter et al, "Microglia emerge as central players in brain disease," Nat Med. 2017. 23(9):1018-1027.
Smith M.B., "March's Advanced Organic Chemistry: Reactions, Mechanisms, and Structure" Wiley, 2013. 7th Edition.
Timmerman R et al, "An Overview of in vitro Methods to Study Microglia," Front. Cell. Neurosci. 2018. 12(242):1-12.
Wuts P.G.M. et al, "Greene's Protective Groups in Organic Synthesis" Wiley-Interscience, 2007, 4th Edition.

* cited by examiner

*Primary Examiner* — Sahar Javanmard
(74) *Attorney, Agent, or Firm* — Susan W. Gorman; Intelink Law Group, PC

(57) ABSTRACT

Compounds and methods useful for inhibition of glial cell activation and for the treatment of diseases associated with increased glial cell activation in mammalian species including humans are presented.

13 Claims, 3 Drawing Sheets

INHIBITION OF GLIAL CELL ACTIVATION

This application is a Continuation of PCT International Application No. PCT/US2025/039,964 filed on Jul. 30, 2025, which claims priority under 35 U.S.C. § 119 on U.S. Patent Application No. 63/677,931 filed in the United States Patent and Trademark Office on Jul. 31, 2024, the entire contents of each of which is hereby incorporated by reference.

FIELD OF THE INVENTION

This invention pertains to inhibition of glial cell activation in mammalian species. The invention provides compounds and methods useful for inhibition of glial cell activation and for the treatment of diseases associated with increased glial cell activation in mammalian species including humans.

BACKGROUND OF THE INVENTION

Glia, also called glial cells or neuroglia, are non-neuronal cells in the central nervous system and the peripheral nervous system that do not produce electrical impulses. The neuroglia make up more than one-half the volume of neural tissue in our body. They maintain homeostasis, form myelin in the peripheral nervous system, and provide support and protection for neurons. In the central nervous system, glial cells include oligodendrocytes, astrocytes, ependymal cells, and microglia, and in the peripheral nervous system they include Schwann cells and satellite cells. [1]

Glial cells have several functions: to surround neurons and hold them in place; to supply nutrients and oxygen to neurons; to insulate one neuron from another; to destroy pathogens and remove dead neurons. They also play a role in neurotransmission and synaptic connections, and in physiological processes such as, but not limited to; breathing, motor activity, vision, cognition, hearing, and pain sensation. In various physiologic or pathologic conditions glial cells become activated and change their cellular phenotype and alter their cellular functions to respond to perturbations in the homeostasis of the local environment. These changes can produce damage to the neuronal and other cells in the central or peripheral nervous systems and are responsible for producing disease and/or dysfunction. [2]

Astrocytes are the most abundant cell type in the central nervous system (CNS) of humans and other mammalian species. A major function of astrocytes involves their activation in response to damage. Astrocyte activation, or astrogliosis, plays a central role in the response to most or all neurological insults including trauma, infections, stroke, tumorigenesis, neurodegeneration, and epilepsy. The second most common glial cell in the central nervous system are microglial cells. In a fashion similar to that of astrocytes, microglial cell can become activated and such activation can also cause neurologic disorder and damage to the nervous system. Other types of glial cells exist in the retina, optic nerve and olfactory nerve which are all part of the central nervous system. [3]

The peripheral nervous system (PNS) consists of all the nerves and ganglia which are outside of the CNS. Glial cells in the PNS function in a similar fashion to the glial cells in the CNS acting to supply nutrients and oxygen to neurons; to insulate one neuron from another; to destroy pathogens and remove dead neurons. Activation of the glial cells of the PNS occurs in a similar fashion to that in the central nervous system.

Activation of glial cells is manifested by alterations in the cellular phenotype such as, but not limited to, changes in; cellular morphology, cell motility and cellular molecular biology. Regardless of the central or peripheral location of glial cells, activation occurs due to intrinsic or extrinsic factors acting directly on the glial cell. At the molecular level, activation of glial cells is manifested by the state dependent expression of specific proteins and genes which influence their normal function and the normal functioning of other cells in the local environment. For example, activation of astrocytes (sometimes referred to as reactive astrocytes) is manifested by up-regulation and the appearance of activation specific biomarkers produced only by the activated astrocytes. Non-limiting examples of biomarkers increased in astrocyte activation are; Glial Fibrillary Acid Protein (GFAP), Matrix Metaloproteinase-9 (MMP-9), Interleukin 1 beta (IL-1B), Interleukin-6 (IL-6), C—C motif chemokine ligand 5 (CCL5) and complement component C3a (C3a). Microglial cells induced to an activated state (sometimes referred to a M1 microglia) also change their molecular cellular phenotype including, but not limited to up regulation of gene expression, production of proteins, as well as cellular morphology. These biomarkers, like those from activated astrocytes, are used to detect microglia cell activation. Activation of microglial cell is detected by changes in the glial cell phenotype including increased production of activation specific biomarkers such as, but not limited to; Tumor Necrosis Factor alpha (TNF-alpha), Interleukin-6 (IL-6), Nitric Oxide synthetase (iNOS), Interferon gamma-induced protein 10 (IP-10/CXCL10), Cyclooxygenase-2 (COX2), (RANTES/CCL5), Cluster of Differentiation protein 86 (CD86) and Vascular Endothelia Growth Factor (VEGF). Activation of other types of glial cells including astrocytes also induces up-regulation of some of these same biomarkers. Other types of glial cells, such as but not limited to; Müller cells and Bergmann glia also manifest their activation state by up-regulation of many of the same biomarkers noted above as well as other biomarkers such as but not limited to: C—C motif chemokine ligand 2 (CCL2) and C—X—C motif) ligand 10 (CXCL10). [4]

The activation of glial cells has various causes. For example, in some cases an intrinsic factors leading to glial cell activation is due to a pathologic process in a nerve cell itself or in other cells in the parenchyma of the CNS and PNS which release activating substances into the extracellular milieu, or as a result of abnormal metabolic processes the nervous system such as, but not limited to; acidosis, nutrient level alterations or hypoxia. In other cases, extrinsic factors such as, but not limited to; physical trauma and chemical substances can induce glial cell activation. Non-limiting examples of substances known to activate glial cells are: Lipopolysaccharide (LPS), Linoleic acid, Interferon gamma (IFN-$\gamma$), Nigericin, Human mobility group protein B1 (HMGB1), Methylphenidate (MPH), Zinc, Beta-amyloid (A$\beta$), Paraquat, C—C motif chemokine ligand 2 (CCL2), Purine nucleotides (ATP), S100 Calcium Binding Protein B (S100B), Interleukin 1 beta (IL-1b), and Envelope glycoprotein GP120 (gp120). [5]

Regardless of the source or the particular activator of glial cells, the result of such activation is the loss of the normal homeostatic and nutritive function of glial cells, as well as the loss of their neuronal protective functions. This pathogenic process leads to damage to neurons in the CNS or PNS by the activated glial cells, largely caused by the presence of bioactive substances produced by the activated glial cell and released into the surrounding tissue and results in many disorders in the CNS [6]. Measures which inhibit or reverse glial cell activation have been shown to treat various neurologic disorders. Thus, there is a need for chemical compounds that inhibit and/or reverse the pathogenic activation glial cells associated with disorders of the nervous system.

SUMMARY OF THE INVENTION

According to one embodiment of the present invention, there is provided compounds for inhibition of glial cell activation in the mammalian nervous system comprising the application, either alone or in combination with other bioactive substances of at least one compound according to of Formula 1 below:

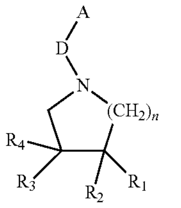

wherein: A is selected from aryl, substituted aryl, heteroaryl, substituted heteroaryl, and wherein D is selected from (CH2)3, COCH2, COCH2CH2, COCH2CH2CH2, CH2COCH2CH2, CHOHCH2CH2, COCHCH, COCH2CH(CH3), COCHC(CH3), COCH2CO, COSCH2CH2, COSCOCH2, $COOCH_2CH2$, CONHCH2CH2, COCH2COCH2, COCOCH2, CSCOCH2, COCOCH2CH2, SO2CH2CH2, SO2CH2CH2CH2, SO2CH2CH(CH3), SO2CHC(CH3), SO2CH2COCH2, CH2COCH2CH2, COarylCH2, arylCOCH2CH2, arylCOCH2, COCH2aryl, COOCH2aryl, COSCH2aryl, COheteroarylCH2, heteroarylCOCH2CH2, heteroarylCOCH2, COCH2heteroaryl, COOCH2heteroaryl, COSCH2heteroaryl, CH2NHCOCH2CH2, CH2CH(OH)CH2CH2 (in each choice aryl and heteroaryl may be optionally substituted);

and wherein n is selected from 1, 2 or 3 and wherein R1, R2, R3, and R4 are independently selected from:

H; OH; F; Cl; Br; I; (halogen)alkyl, optionally substituted C1 to C8 straight chain or branched chain alkyl; optionally substituted C1 to C8 cycloalkyl; heterocycloalkyl; alkylheterocycloalkyl; optionally substituted C1 to C8 alkenyl; optionally substituted C1 to C8 alkynyl; optionally substituted aryl; optionally substituted alkylaryl; optionally substituted heteroaryl; optionally substituted alkylheteroaryl; O-alkyl; O-optionally substituted alkyl, O-cycloalkyl; O-alkylcycloalkyl; O-aryl; O-optionally substituted aryl; alkyl-O-aryl; alkyl-O-optionally substituted aryl; C(O)-aryl; C(O)-optionally substituted aryl; CH2C(O)-aryl; CH2C(O)-optionallysubstituted aryl; O-(halogen)alkyl;

and wherein adjacent substituents R1 and R3, R2 and R4, when present, may form a saturated or unsaturated 5 membered or 6-membered or 7 membered carbocyclic or heterocyclic ring;

wherein alkenyl, if present, may refer to one or more double bond and each double bond may independently be cis or trans, E or Z, a cis/trans mixture, or an E/Z mixture; and wherein if an asymmetric center is present or asymmetric centers are present the compound may be in the form of a racemic mixture, a single enantiomer, a diastereoisomeric mixture, an enantiomeric diastereomer, a meso-compound, a pure epimer, or a mixture of epimers thereof.

and wherein a hydrogen, several hydrogens or all hydrogens may be replaced with deuterium. or wherein, if appropriate, the compound is a pharmaceutically acceptable salt, ester, or prodrug form thereof.

A further embodiment of the invention is the use of a compound as defined above in the manufacture of a medicament for the treatment of a human at risk for or having at least one disease or disorder associated with glial cell activation. Non-limiting examples of general categories of disorders in which glia activation is a known pathogenic factor are: neurodegenerative diseases, neurodevelopmental disorders, neuropsychiatric disorders, and peripheral neuropathies. Non-limiting examples of neurodegenerative diseases; Alzheimer's disease, Amyotrophic lateral sclerosis, Parkinson's disease, Prion diseases, Ataxia, Multiple system atrophy, Corticobasal degeneration, Guillain-Barre syndrome, Lewy body dementia, Multiple sclerosis, Motor neuron disease, Retinopathy, Spinocerebellar ataxia and/or Huntington's disease. Non-limiting examples of neurodevelopmental disorders are; Autism Spectrum Disorder, Attention Deficit Hyperactivity disorder, and Fragile X syndrome. Non-limiting examples of neuropsychiatric disorders are; Anxiety disorder, Bipolar disorder, Depression, Pos-Traumatic Stress disorder and Schizophrenia. Non-limiting examples of Peripheral neuropathies are; Diabetic neuropathies and Neuropathic pain. Other non-limiting examples of disorders associated with glial cell activation include, but are not limited to; Neuromyelitis Optica spectrum disorder, Post-Traumatic Brain Injury syndrome, and several types of epilepsy.

Another embodiment of the invention is the use of a compound as defined above in the manufacture of a medicament for the treatment of a human or having at least one disease or disorder associated with glial cell activation in combination with one or more other therapeutic modalities, including but not limited to: other chemical or biological compositions of matter, such as but not limited to; naturally occurring chemical compounds, inorganic elements or antibodies; synthetic chemical compounds, peptides, or proteins; or physical therapies such as but limited to electroshock, manipulative physical therapy; as well as behavioral or cognitive therapy.

DETAIL DESCRIPTION OF INVENTION

Figure 1A:
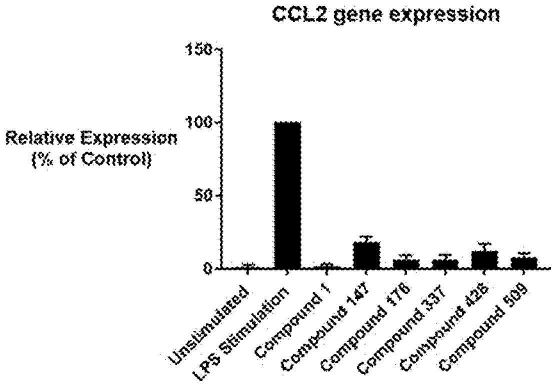
FIGS. 1*a-f*: Biomarkers induced by activation of cultivated human HMC3 microglia cells by exposure to known microglial activators after pre-treatment with compounds of Formula 1. Cells were stimulated with lipopolysaccharide (LPS) at 100 ng/mL in culture media or paraquat dichloride hydrate (PQ) at 40 uM and the relative gene expression of; CCL2, IL-6, IL-1β, and VEGF (FIG. 1*a-d*) and corresponding induced production and secretion of IL-1β, and TNF-alpha, (FIG. 1*e-f*) were measured relative to control HCM3 cells not treated with the compounds of Formula 1, prior to induction of activation. HCM3 cells not induced to activation by LPS (unstimulated) were normal controls. The compounds of Formula 1 simultaneously inhibited the production and/or release of these biomarkers, while not affecting glia cells viability.

The compounds embodied by Formula 1 have been found to inhibit activation of glial cells from mammalian and human tissues. In certain embodiments this disclosure provides compounds that are therefore capable of inhibiting the activation of glial cells and subsequent biologic effects and disorders caused by activated glial cells in the nervous system of mammalian species and provides methods of treatment, prevention, inhibition, or amelioration of one or more diseases associated with glial cell activation in humans using the compounds and compositions disclosed herein.

Compounds embodied by Formula I may have one or several asymmetric centers and therefore can exist in different stereoisomeric configurations. Consequently, the compound of Formula I can occur as individual (pure) enantiomers, individual pure enantiomeric diastereomers as well as a mixture of enantiomers or diastereomers. The scope of the present invention includes both single enantiomers and mixtures thereof in all ratios. The scope of the present invention further includes all tautomeric forms ("tautomers") of the compounds of Formula I, and all mixtures thereof in any ratio. It will be appreciated by one skilled in the art that a single compound may exhibit more than one type of isomerism.

The enantiomeric compounds of Formula I may be resolved into their pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers maybe synthesized by using an optically active starting material, by asymmetric synthesis using optically active reagents, substrates, catalysts or solvents, or by converting one stereoisomer into the other by asymmetric transformation or inversion.

The compounds of the present invention may exist in unsolvated as well as a variety of solvated forms with pharmaceutically acceptable solvents such as water, ethanol, and the like. In general, the solvated forms are considered equivalent to the unsolvated forms for the purposes of the present invention. It should be understood that pharmaceutically acceptable solvents further includes isotopically substituted solvents such as $D_2O$, dimethyl sulfoxide-d6 and the like. The term 'solvate' is used herein to describe a complex comprising the compound of the invention and one or more pharmaceutically acceptable solvent molecules, including water. As such, all manner of hydrates of the compound are included by the term 'solvate'. It is intended that the present invention embrace unsolvated forms, solvated forms and mixtures of solvated forms in any ratio.

The compound of the present invention and/or its salts and/or solvate may exist as amorphous solids or may exist in one or more crystalline states, i.e. polymorphs. Polymorphs of the compound of Formula I are encompassed in the present invention and may be prepared by crystallization under a number of different conditions such as, for example, using different solvents or different solvent mixtures; crystallization at different temperatures; and using various modes of cooling ranging from very fast to very slow during crystallization. Polymorphs may also be obtained by heating or melting a compound of Formula I followed by gradual or fast cooling. The presence of polymorphs may be determined by solid NMR spectroscopy, IR spectroscopy, differential scanning calorimetry, powder x-ray diffraction or other techniques. It should be understood that all such crystalline and amorphous forms of the compound of Formula I, and its salts, solvates and prodrugs thereof are encompassed by the invention and the claims.

The present invention also includes all pharmaceutically acceptable isotopically-labeled variations of the compound of Formula I. Such isotopically-labeled variations are compounds having the same Formula and molecular formula as the compound of Formula I but wherein one or more atoms are replaced by atoms having an atomic mass or mass number different from the atomic mass or mass number usually found in nature. Examples of isotopes that may be incorporated into the compound of the present invention include isotopes of hydrogen, carbon, fluorine, nitrogen, and oxygen, such as $^{2}H$, $^{3}H$, $^{11}C$, $^{13}C$, $^{14}C$, $^{18}F$, $^{13}N$ $^{15}N$ $^{17}O$ and $^{18}O$, respectively.

Certain isotopically labeled variations of the compound of the present invention such as, for example, those incorporating a radioactive isotope such as $^{3}H$ and $^{14}C$, are useful in drug and/or substrate tissue distribution studies. Tritium, i.e. $^{3}H$, and carbon-14, i.e. $^{14}C$, are particularly preferred due their ease of preparation and detection. Further, substitution with heavier isotopes such as deuterium, i.e. $^{2}H$, can afford certain therapeutic advantages resulting from greater metabolic stability, for example, increased in vivo half-life or reduced dosage requirements, and hence may be preferred in some circumstances. Isotopically labeled compounds of Formula I of this invention and prodrugs thereof can generally be prepared by carrying out the procedures disclosed in the Schemes and/or in the Examples by substituting a readily available isotopically labeled reagent for a non-isotopically labeled reagent.

The compounds of Formula I may be administered as a prodrug. The term prodrug refers to a compound which is transformed in vivo to a compound of Formula I, or a pharmaceutically acceptable salt or solvate of the compound. The transformation may occur by various mechanisms, such as via hydrolysis in blood. A prodrug of the compound of Formula I may be formed in a conventional manner according to methods known in the art. A thorough discussion of prodrugs is provided by V. Stella in *Pro-drugs as Novel Delivery Systems*, Vol. 14 of the A.C.S. Symposium Series (Stella (1975)), and in *Bio-reversible Carriers in Drug Design* (Roche (1987)), both of which are incorporated herein by reference.

"Alkyl" means a straight or branched chain, saturated hydrocarbon radical. By way of example, the hydrocarbon chain may have from one to twenty carbons, one to sixteen carbons, one to fourteen carbons, one to twelve carbons, one to ten carbons, one to eight carbons, one to six carbons, one to four carbons, etc. "Lower alkyl" may refer to alkyls having, e.g., one to six carbons, one to four carbons, etc. In certain examples, a straight chain alkyl may have from one to six carbon atoms and a branched alkyl three to six carbon atoms, e.g., methyl, ethyl, propyl, 2-propyl, butyl (including all isomeric forms), pentyl (including all isomeric forms), and the like. "Me" means methyl, "Et" means ethyl, and "iPr" means isopropyl. Alkyl may be optionally substituted, e.g., optionally substituted with oxygen, silicon, sulfur or optionally substituted with OH, O-alkyl, SH, S-alkyl, $NH_2$, NH-alkyl. In another example, alkyl may be $C_1$ to $C_{12}$ straight chain or branched chain alkyl optionally substituted with oxygen, silicon, sulfur or optionally substituted with OH, O-alkyl, SH, S-alkyl, $NH_2$, NH-alkyl.

"Alkylene" means a divalent alkyl, with alkyl as defined above.

"Aryl" means a monocyclic or bicyclic aromatic hydrocarbon radical, e.g., having from of 6 to 20 or 6 to 10 ring atoms e.g., phenyl or naphthyl. Aryl may be optionally substituted, e.g., substituted phenyl or substituted naphthyl. Further examples of optional substitution are defined below.

"Alkylaryl" means a (alkylene)-R radical where R is aryl as defined above. In certain examples, alkylaryl may be alkylphenyl, alkylsubstituted phenyl, alkylnaphthyl or alkyl-substituted naphthyl. Alkylaryl may be optionally substituted. Further examples of optional substitution are defined below.

"Alkenyl" means a straight or branched chain, saturated hydrocarbon radical which contains a carbon-carbon double bond. By way of example, the hydrocarbon chain may have from two to twenty carbons, two to sixteen carbons, two to fourteen carbons, two to twelve carbons, two to ten carbons, two to eight carbons, two to six carbons, two to four carbons, etc. "Lower alkenyl" may refer to alkenyls having, e.g., two to six carbons, two to four carbons, etc. In certain examples, a straight chain alkenyl may have from two to six carbon atoms and a branched alkyl three to six carbon atoms, e.g., a vinyl group, an allyl group, butene (including all isomeric forms), pentene (including all isomeric forms), and the like. Alkenyl may be optionally substituted. In certain examples, alkenyl may be a $C_2$ to $C_{12}$ straight chain or branched chain hydrocarbon containing a carbon-carbon double bond, optionally substituted with oxygen, silicon or sulfur or optionally substituted with OH, O-alkyl, SH, S-alkyl, $NH_2$ or NH-alkyl.

"Alkynyl" means a straight or branched chain, saturated hydrocarbon radical which contains a carbon-carbon triple bond. By way of example, the hydrocarbon chain may have from two to twenty carbons, two to sixteen carbons, two to fourteen carbons, two to twelve carbons, two to ten carbons, two to eight carbons, two to six carbons, two to four carbons, etc. "Lower alkynyl" may refer to alkynyls having, e.g., two to six carbons, two to four carbons, etc. In certain examples, a straight chain alkynyl may have from two to six carbon atoms and a branched alkyl three to six carbon atoms, e.g., an acetylene group, a propargyl group, butyne (including all isomeric forms), pentyne (including all isomeric forms), and the like. Alkynyl may be optionally substituted. In certain examples, alkynyl may be a $C_2$ to $C_{12}$ straight chain or branched chain hydrocarbon containing a carbon-carbon triple bond, optionally substituted with oxygen, silicon or sulfur, or optionally substituted with OH, O-alkyl, SH, S-alkyl, $NH_2$ or NH-alkyl.

"Cycloalkyl" means a cyclic saturated or partially saturated hydrocarbon radical (or an alicyclic radical). By way of example, the cycloalkyl may have from three to twenty carbon atoms, from three to sixteen carbon atoms, from three to fourteen carbon atoms, from three to twelve carbon atoms, from three to ten carbon atoms, from three to eight carbon atoms, from three to seven carbon atoms, from three to six carbon atoms, etc., wherein one or two carbon atoms may be replaced by an oxo group, e.g., admantanyl, cyclopropyl, cyclobutyl, cyclopentyl, cyclohexyl, cyclohexenyl, indanyl and the like.

"Alkylcycloalkyl" means a (alkylene)-R radical where R is cycloalkyl as defined above; e.g., cyclopropylmethyl, cyclobutylmethyl, cyclopentylethyl, or cyclohexylmethyl, and the like. In another example, alkylcycloalkyl has four to twelve carbon atoms, i.e., $C_4$-$C_{12}$ alkylcycloalkyl.

"O-alkyl" means an (oxygen)-R radical where R is alkyl as defined above. For example, O-alkyl may be an oxygen atom bonded to a $C_1$ to $C_6$ straight chain or branched chain alkyl.

"O-cycloalkyl" means an (oxygen)-R radical where R is cycloalkyl as defined above. For example, O-cycloalkyl is an oxygen atom bonded to a $C_3$ to $C_7$ cycloalkyl.

"O-alkylcycloalkyl" means an (oxygen)-R radical where R is alkylcycloalkyl as defined above. For example, O-cycloalkyl is an oxygen atom bonded to a $C_4$ to $C_8$ alkylcycloalkyl.

"Heterocyclyl" or "heterocycloalkyl" means a saturated or unsaturated monocyclic group, in which one or two ring atoms are heteroatom selected from N, O, or S, the remaining ring atoms being C. Heterocyclyl and heterocycloalkyl includes, e.g., where the heterocycle comprises one or two hetero atoms selected from O, S, or N, including a $C_2$ to $C_6$ heterocycloalkyl. The heterocyclyl ring is optionally fused to a (one) aryl or heteroaryl ring as defined herein. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl. "Heterocyclyl" or "heterocyclylalkyl" may be optionally substituted as defined below.

"Alkylheterocycloalkyl" means an -(alkylene)-R radical where R is heterocyclyl ring as defined above e.g., tetrahydrofuranylmethyl, piperazinylmethyl, morpholinylethyl, and the like. Alkylheterocycloalkyl also includes, e.g., where the heterocycle comprises one or two hetero atoms selected from O, S, or N and has three to eleven carbon atoms, i.e., $C_3$ to $C_{11}$ alkylheterocycloalkyl, and includes when N is present in the heterocyclic ring the nitrogen atom may be in the form of an amide, carbamate or urea. "Alkylheterocycloalkyl" may be optionally substituted are defined below.

"Heteroaryl" means a monocyclic or bicyclic aromatic radical, where one or more, preferably one, two, or three, ring atoms are heteroatom selected from N, O, or S, the remaining ring atoms being carbon. Representative examples include, but are not limited to, pyrrolyl, thienyl (thiophenyl), thiazolyl, imidazolyl, furanyl, indolyl, isoindolyl, oxazolyl, isoxazolyl, diazolyl, pyrazolyl, triazolyl, benzothiazolyl, benzoxazolyl, quinolinyl, isoquinolinyl, pyridinyl (pyridyl), pyrimidinyl, pyrazinyl, pyridazinyl, tetrazolyl, and the like. "Heteroaryl" may be optionally substituted as defined below.

"Oxo" or "carbonyl" means a =(O) group or C=O group, respectively.

The term "substituted" or "optionally substituted" means that the referenced group is substituted with one or more additional group(s) individually and independently selected from groups described herein. In some embodiments, an optional substituent is selected from oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoroalkyl, substituted or unsubstituted heteroalkyl, substituted or unsubstituted alkoxy, fluoroalkoxy, —S-alkyl, —$S(O)_2$-alkyl, —CONH ((substituted or unsubstituted alkyl) or (substituted or unsubstituted phenyl)), —CON(H or alkyl)2, —OCON (substituted or unsubstituted alkyl)$_2$, —NHCONH ((substituted or unsubstituted alkyl) or (substituted or unsubstituted phenyl)), —NHCOalkyl, —N(substituted or unsubstituted alkyl) CO (substituted or unsubstituted alkyl), —NHCOO (substituted or unsubstituted alkyl), —C(OH) (substituted or unsubstituted alkyl)$_2$, and —$C(NH_2)$ (substituted or unsubstituted alkyl)$_2$, $B(OH)_2$, $B(OMe)_2$, $B(OEt)_2$, boronate pinacol ester and the like. In some embodiments, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —$S(O)_2$—$CH_3$, —$CONH_2$, —$CONHCH_3$, —$NHCONHCH_3$, —$COCH_3$, —COOH, boronic acid, boronate esters and the like. In some embodiments, substituted groups are substituted with one, two or three of the preceding groups. In some embodiments, substituted groups are substituted with one or two of the preceding groups. In some embodiments, substituted groups are substituted with one of the preceding groups. Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

"Activation" as used herein refers to changes in the cellular phenotype such as, but not limited to, changes in; cellular morphology, cell motility and cellular molecular biology. Regardless of the central or peripheral location of glial cells, activation occurs due to intrinsic or extrinsic factors acting directly on the glial cell. At the molecular level, activation of glial cells is characterized and defined by the activation state dependent expression of specific proteins and genes such as but not limited to; Glial Fibrillary Acid Protein (GFAP), Matrix Metaloproteinase-9 (MMP-9), Interleukin 1 beta (IL-1β), Interleukin-6 (IL-6), C—C motif chemokine ligand 5 (CCL5), complement component C3a (C3a), Tumor Necrosis Factor alpha (TNF-alpha), Interleukin-6 (IL-6), Nitric Oxide Synthetase (iNOS), Interferon gamma-induced protein 10 (IP-10/CXCL10), Cyclooxygenase-2 (COX2), Regulated upon Activation, Normal T Cell Expressed and Secreted (RANTES/CCL5), Vascular Endothelia Growth Factor (VEGF). As defined herein "activation" does not imply the simultaneous and equal change in expression of all associated proteins and genes. In kind, the term "activated" as used herein refers to a glial cell which has undergone such activation.

"Addition compound" refers to a complex of two or more complete molecules in which each preserves its fundamental structure, and no covalent bonds are made or broken (for example, hydrates of salts, adducts).

"Aliphatic acid" refers to acids of nonaromatic hydrocarbons. Examples of aliphatic acids include, but are not limited to: butyric acid, hexanoic acid, propionic acid, octanoic acid, and acetic acid.

"Alkene" refers to an unsaturated linear divalent hydrocarbon moiety of one to twelve, typically one to six, carbon atoms or a saturated branched divalent hydrocarbon moiety of three to twelve, typically three to six, carbon atoms. Exemplary alkene groups include, but are not limited to, methylene, ethylene, propylene, butylene, pentylene, and the like.

"Antagonist" refers to a compound or a composition that attenuates the effect of an agonist. The antagonist can directly bind reversibly or irreversibly to a region of the receptor in common with an agonist. An antagonist can also bind at a different site on the receptor or an associated ion channel. Thus, the term "antagonist" includes a functional antagonist. A "functional antagonist" refers to a compound and/or composition that reverses the effects of an agonist by means other than acting at the same receptor as the agonist, i.e., a functional antagonist causes a response in the tissue or animal which opposes the action of an agonist. Examples include agents which have opposing effects on an intracellular second messenger or on a physiologic state in an animal (for example, blood pressure).

"Biological activity" as used herein having an effect on or eliciting a response from a living cell, tissue, organ, or physiologic activity, such as, but not limited to: altering gene and/or protein expression, protein phosphorylation, cellular behavior, tissue activity, organ or organism function.

"Biomarker" as used herein, means a measurable substance or physical property of a biological entity whose presence is indicative of some particular state of the biological entity or phenomenon occurring to it such as, but not limited to; a disease, infection, or environmental exposure. More generally as used herein, a biomarker is anything that can be used as an indicator of a particular state or some other physiological state of a cell, tissue, organ or an organism that may also be a measurable indicator of the severity or the presence of a particular disease state.

"Carboxyl" refers to an organic functional group consisting of a carbon atom double bonded to an oxygen atom and single bonded to a hydroxyl group.

"Cellular phenotype" as used herein refers to the physical, functional, biochemical, molecular biological and morphologic characteristics of a cell in a particular environment.

"Central Nervous System, (CNS)" as used herein refers to the part of the mammalian nervous system consisting of the brain and spinal cord, as well as the retina, optic nerve, olfactory and auditory nerves.

"Chiral center" (i.e., stereochemical center, stereocenter, or stereogenic center) refers to an asymmetrically substituted atom, e.g., a carbon atom to which four different groups are attached. The ultimate criterion of a chiral center, however, is non-superimposability of its mirror image. If an asymmetric center is present in one or more substituents, the compound may be in the form of a racemic mixture, a single enantiomer, a diastereoisomeric mixture, an enantiomeric diastereomer, a meso compound, a pure epimer, or a mixture of epimers thereof.

"Clinically significant" refers to an effect which produces a change in the existing phenotype.

"Derivative" refers to a compound that is derived from some parent compound where one atom is replaced with another atom or group of atoms and usually maintains its general structure. For example, trichloromethane (chloroform) is a derivative of methane.

"Epithelium (epithelia, plural) or epithelial tissues" as used herein means a type of animal tissue made up of densely packed cells that rest on a basement membrane to act as a covering of a free surface such as, but not limited to the surface of the human body; or lining of various bodily surfaces, such as but not limited to the eyes; or lining various body cavities such as but not limited the abdominal cavity; or lining the lumina of tubular structures within organs. Non-limiting examples of epithelial tissues include, but are not limited to the; oral, nasal, ocular, respiratory, rectal and urogenital epithelium.

"Enantiomeric excess" refers to the difference between the amounts of enantiomers. The percentage of enantiomeric excess (% ee) can be calculated by subtracting the percentage of one enantiomer from the percentage of the other enantiomer. For example, if the % of (R)-enantiomer is 99% and % of(S)-enantiomer is 1%, the % ee of (R)-isomer is 99%-1% or 98%.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by the same or different halo atoms. The term "haloalkyl" also includes perhalogenated alkyl groups in which all alkyl hydrogen atoms are replaced by halogen atoms. Exemplary haloalkyl groups include, but are not limited to: $—CH_2F$, $—CH_2Cl$, $—CF_3$, $—CH_2CF_3$, $—CH_2CCl_3$, and the like.

"Hetero-substituted alkyl" refers to an alkyl group, as defined herein, that contains one or more heteroatoms such as N, O, or S. Such heteroatoms can be hydroxy, alkoxy, amino, mono-, di-alkyl amino, thiol, alkylthiol, etc.

"Hydroxyalkyl" refers to an alkyl group, as defined herein, having one or more hydroxyl substituent(s).

"Glial cells, (Glia)" as used herein refers to a family of related non-neuronal cells present in the central and peripheral nervous system of humans and other mammals. As a family of cells, glial cells have various names including, but not limited to; Astrocytes, Bergmann glia, Ependymal cells, Oligodendrocytes, Microglia, Müller cells, Radial glia, Satellite cells, and Schwann cells.

"Keto acid" refers to organic compounds that contain a carboxylic acid group and a ketone group.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N, O-dimethylhydroxylamino, and the like.

"Leukocyte or leukocytes" as used herein refer to a colorless cell that circulates in the blood and body fluids and is involved in counteracting foreign substances and infectious disease as well as being causative of inflammatory diseases. They have also been referred to as white (blood) cells. There are several types, all are amoeboid cells with a nucleus, including lymphocytes, granulocytes, monocytes, and macrophages.

"Ligand" as used herein means a biochemical substance in the form of a nucleic acid, protein or peptide that forms a complex with another biomolecule in a cell or tissue to serve a biological purpose.

"Modulate" as used herein means to decrease or increase the quality, quantity, intensity or duration of a biological product or process.

"Peripheral blood mononuclear cell (PBMC)" as used herein means any peripheral blood cell having a round nucleus. These cells are a subset of leukocytes and consist of lymphocytes (T cells, B cells, NK cells) and monocytes, whereas erythrocytes and platelets have no nuclei and granulocytes (neutrophils, basophils, and eosinophils) have multi-lobed nuclei.

"Peripheral nervous system, (PNS)" as used herein refers to that portion of the mammalian nervous system consisting of the nerves and ganglia, which lie outside the brain and the spinal cord, with the exceptions of the olfactory nerve and epithelia and the optic nerve (cranial nerve II) along with the retina, which are considered parts of the central nervous system based on their developmental origin.

"Pharmaceutically acceptable excipient" refers to an excipient that is useful in preparing a pharmaceutical composition that is generally safe, non-toxic, and neither biologically nor otherwise undesirable, and includes excipients that are acceptable for veterinary use as well as human pharmaceutical use.

"Pharmaceutically acceptable salt" of a compound means a salt that is pharmaceutically acceptable and that possesses the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A "pharmaceutically acceptable salt" of a compound also includes salts formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Pharmaceutically acceptable vehicle means a carrier or inert medium used as a solvent (or diluent) in which the medicinally active agent is formulated and/or administered.

The term "Phenotype" as used herein refers to the observed set of physical properties of a biological entity, such as but not limited to; a cell, a tissue, or whole organism, resulting from expression of the set of genes it possesses (i.e., "genotype') and the influence of the current environment of the biological entity.

The terms "pro-drug" and "prodrug" are used interchangeably herein and refer to any compound which releases an active parent drug according to Formula 1, or a pharmaceutically acceptable salt or solvate of Formula 1, in vivo when such prodrug is administered to a mammalian subject. Prodrugs of a compound of Formula 1 are prepared by modifying one or more functional group(s) present in the compound of Formula 1 in such a way that the modification (s) may be cleaved in vivo to release the parent compound. Prodrugs include compounds of Formula 1 wherein a hydroxy group in a compound of Formula 1 is bonded to any group that may be cleaved in vivo to regenerate the free hydroxyl, aliphatic alcohol, amino, or sulfhydryl group, respectively. Examples of prodrugs include, but are not limited to, esters (e.g., acetate, formate, glycol and benzoate derivatives of Formula 1) and the like. For example, the compound according to Formula 1 that is methyl 3-(4-hydroxyphenoxy)-3-methyl-butanoate can be reacted under acidic conditions with 2-hydroxybenzoic acid to produce, [4-(3-methoxy-1, -1-dimethyl-3oxo-propoxy) 2-hydoxybenzoate an ester prodrug that will be hydrolyzed to 2-hydroxybenzoic acid and the starting compound by esterase enzymes in tissues. The transformation from prodrug to a compound of Formula 1, or a pharmaceutically acceptable salt or solvate thereof, may occur by various mechanisms, such as via hydrolysis in blood. A prodrug of the compound of Formula 1 may be formed in a conventional manner according to methods known in the art. A thorough discussion of prodrugs is provided by V. Stella in *Pro-drugs as Novel Delivery Systems*, Vol. 14 of the A.C.S. Symposium Series (Stella (1975)), and in *Bioreversible Carriers in Drug Design* (Roche (1987)), both of which are incorporated herein by reference.

The term "prophylaxis" of a state, disorder, disease or condition as used herein refers to prevention of the appearance of clinical symptoms of the state, disorder, disease or condition developing in a patient that is predisposed to the state, disorder, disease, or condition.

"Protecting group" refers to a moiety, with the exception of alkyl groups, that when attached to a reactive group in a molecule masks, reduces, or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated by reference herein in their entirety. Representative hydroxy protecting groups include acyl groups, benzyl and trityl ethers, tetrahydropyranyl ethers, trialkylsilyl ethers, and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P, or S) to which it is attached.

"Retinopathy" is a medical term which refers to any disease of the retina. Examples of retinopathy include, but are not limited to, diabetic retinopathy, retinopathy of prematurity, hypertensive retinopathy, central serous retinopathy, diabetic macular edema, and macular degeneration.

"Signal transduction" or "signaling pathway activity" refers to a biochemical causal relationship generally initiated by a protein-protein interaction such as binding of a biological active factor to a receptor, resulting in transmission of a signal from one portion of a cell to another portion of a cell. In general, the transmission can involve specific phosphorylation of one or more tyrosine, serine, or threonine residues on one or more protein components such as enzymes or transcription factors (i.e. intracellular secondary messengers) in the series of reactions causing signal transduction (often referred to as a cascade) that results in measurable changes to the cell. Penultimate cellular processes typically include nuclear events, resulting in a change in gene expression. Terminal events of signal transduction cascade result in changes in cellular activity such as but not limited to, alterations in protein products produced and/or secreted by the cell, changes in cellular behavior characteristics of division, motility, adherence, etc.

"Stereoisomer" means molecules that have the same molecular formula, molecular weight and sequence of bonded atoms (constitution), but differ in the three-dimensional orientations of their atoms in space. By definition, molecules that are stereoisomers of each other represent the same structural isomer. The chemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

"A therapeutically effective amount" means the amount of a compound that, when administered to an individual for treating a disease, is sufficient to effect such treatment for the disease, as defined below. The "therapeutically effective amount" will vary depending on the compound, the disease and its severity or affected organ or tissue and the age, weight, etc., of the individual to be treated.

"Tautomer" or "tautomeric form" means structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. The compounds of the present invention according to Formula 1 can exist in different tautomeric states depending on the environment of the particular compound, such as the acidity or alkalinity (i.e. pH) of the solution in which they are dissolved.

"Treating" or "treatment" of a disease means inhibiting the disease, i.e., arresting or reducing the pathophysiologic process or processes of the disease or its clinical symptoms; or relieving the disease, i.e., causing regression of the pathophysiologic process or processes of disease or reducing the clinical manifestations of the pathophysiologic process or processes of the specific disease.

In some embodiments, a compound of the disclosure is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the lipid modulating compound described herein are reacted with an organic base, such as, but not limited to, ethanolamine, diethanolamine, triethanolamine, methylamine, dimethylamine, trimethylamine, ethylamine, diethylamine, triethylamine, N-methylglucamine, dicyclohexylamine, tris (hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

In the scope of the embodiments, the compounds described herein include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including, but not limited to, single enantiomers and enantiomeric diastereomers, meso compounds, stereoisomers, racemic mixtures, and diasteroisomeric mixtures. Compounds described herein having one or more double bonds include cis/trans isomers, E/Z isomers and geometric isomers.

In some embodiments, sites on the compounds disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group. Examples of such substituents can be found in Burger's Medicinal Chemistry, Drug Discovery and Development, 8 Volume Set (Abraham (2010)) and in Foye's Principles of Medicinal Chemistry (Lemke (2012)).

In some embodiments, sites on the compounds disclosed herein are not susceptible to various metabolic reactions. Therefore incorporation of appropriate substituents at or near or distant from the places of a lack of metabolic reactions will modulate, enhance, or maximize the metabolic pathways. In specific embodiments, the appropriate substituent (metabolic handle) to enhance, or maximize the susceptibility of the aromatic ring to metabolic reactions is, by way of example only, is a phenolic or methoxy or carboxylate group. Examples of such substituents can be found in Burger's Medicinal Chemistry, Drug Discovery and Development, 8 Volume Set (Abraham (2010)) and in Foye's Principles of Medicinal Chemistry (Lemke (2012)).

Throughout the specification, groups and substituents thereof can be chosen by one skilled in the field to provide stable moieties and compounds.

I. SYNTHESIS OF THE COMPOUNDS

In general, compounds of Formula I may be prepared using a number of methods known in the chemical arts, particularly in light of the description contained herein, in combination with the knowledge of the skilled artisan. Various starting materials, intermediates, and reagents may be purchased from commercial sources or made according to literature methods or adaptations thereof. Although other reagents, compounds or methods can be used in practice or testing, generalized methods for the preparation of the compound of Formula I are illustrated by the following descriptions and reaction Schemes. The methods disclosed herein, including those outlined in the Schemes, descriptions, and Examples are for intended for illustrative purposes and are not to be construed in any manner as limitations thereon. Various changes and modifications will be obvious to those of skill in the art given the benefit of the present disclosure and are deemed to be within the spirit and scope of the present disclosure as further defined in the appended claims.

Although specific embodiments of various aspects of the invention will be described with reference to the Schemes, Preparations and/or Examples, it should be understood that such embodiments are by way of example only and are merely illustrative of a small number of the many possible specific embodiments which can represent applications of the principles of the present disclosure. The starting materials used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March's Advanced Organic Chemistry: Reactions, Mechanisms, and Structure (Smith (2013)), Design and Strategy in Organic Synthesis (Hanessian (2013)) Greene's Protective Groups in Organic Synthesis (Wuts (2006)) and Fiesers' Reagents for Organic Synthesis (Volumes 1-27) (Ho (2013)), each of which are incorporated by reference in their entirety.

General methods for the preparation of the compounds as disclosed herein may be derived from known reactions in the field, and the reactions may be modified by the use of appropriate reagents and conditions, as would be recognized by the skilled person, for the introduction of the various moieties found in the formulae as provided herein.

The intermediate products described can be recovered by extraction, evaporation, or other techniques known in the art. The crude materials may then be optionally purified by chromatography, HPLC, recrystallization, trituration, distillation, or other techniques known in the art. In the discussions below, the following abbreviations were used: EtOH (ethanol) NaOH (sodium ethoxide), DMSO (dimethylsulfoxide), MOM (methoxymethyl), THF (tetrahydrofuran), Dess-Martin (Dess-Martin Periodinane) and TBS (tert-butyldimethylsilyl).

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. Methods of introducing and removing protecting groups are well known to those of ordinary skill in the art and are described in Greene's Protective Groups in Organic Synthesis (Wuts (2006)). Alternate reagents, starting materials, as well as methods for optimizing or adapting the procedures described herein would also be readily determined by one skilled in the art.

Synthesis of Analogs in Table 1

Beginning with a suitable nitrile alcohol having the desired substitutions $R_1$, $R_2$, $R_3$, and $R_4$, as shown in Scheme 1 below, reduction of the CN to $CH_2NH_2$ can be achieved using an aluminum hydride such as $LIAlH_4$ or catalytic Hydrogenation with Hydrogen over Raney Nickel, Palladium Black or $PtO_2$. The resulting amino alcohol may spontaneously cyclize to the pyrrolidine or may require some help such as a trace of acid catalysis. A Mannich reaction (Blicke, F. F. (2011). "The Mannich Reaction". Organic Reactions. 1 (10): 303-341) between the pyrrolidine, the appropriate aryl methyl ketone and formaldehyde leads to the desired adduct after purification.

Scheme 1

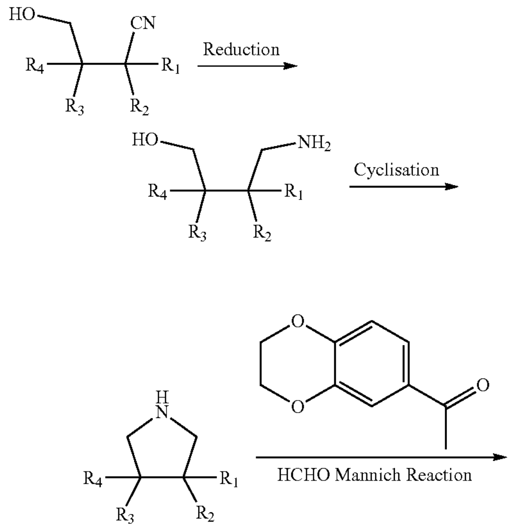

-continued

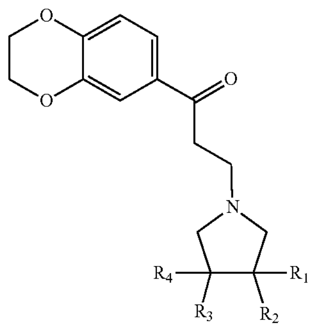

The 1-(2,3-dihydro-1,4-benzodioxin-6-yl) ethenone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 2

The synthesis of these analogs is similar starting from a suitable nitrile alcohol having the desired substitutions $R_1$, $R_2$, $R_3$, and $R_4$, as shown in Scheme 2 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 2

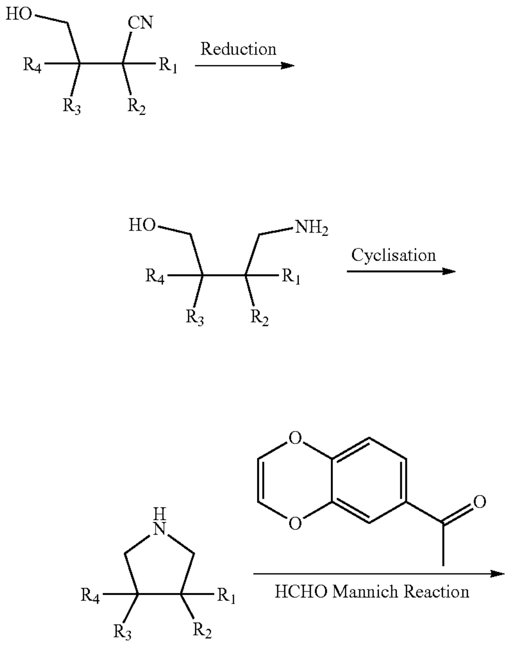

-continued

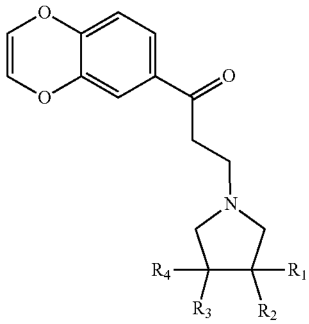

In this case the 1-(1,4-benzodioxin-6-yl) ethenone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 3

The synthesis of these analogs is similar starting from a suitable nitrile alcohol having the desired substitutions $R_1$, $R_2$, $R_3$, and $R_4$, as shown in Scheme 3 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 3

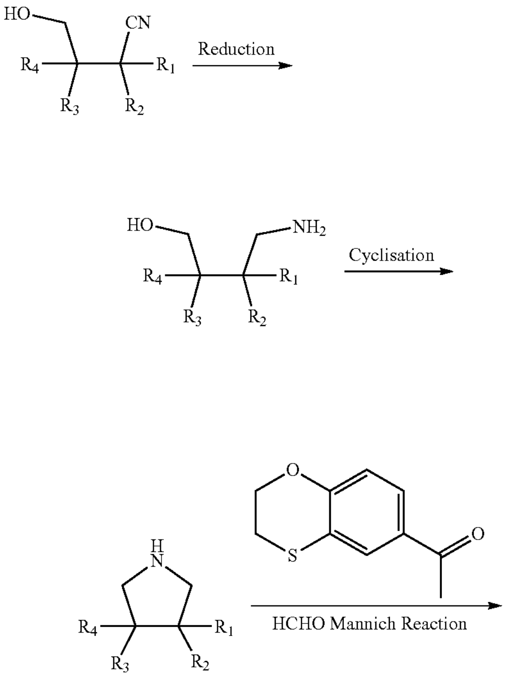

-continued

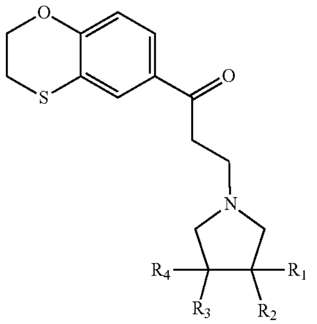

In this case the 1-(2,3-dihydro-1,4-benzoxathiin-6-yl) ethenone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 4

The synthesis of these analogs is similar starting from a suitable nitrile alcohol having the desired substitutions $R_1$, $R_2$, $R_3$, and $R_4$, as shown in Scheme 4 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 4

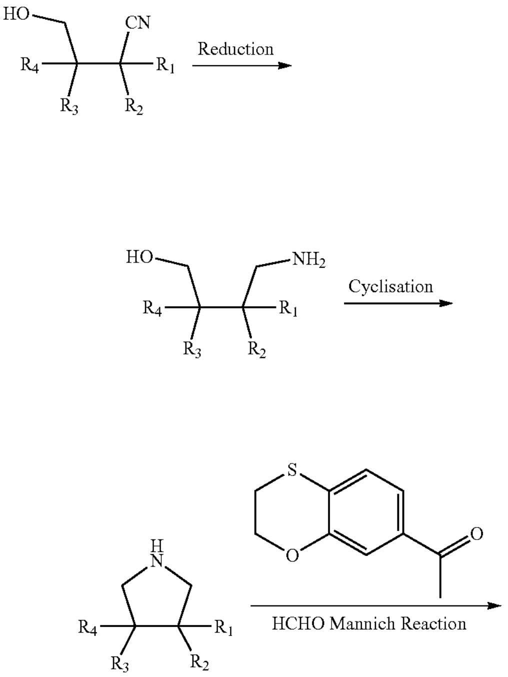

-continued

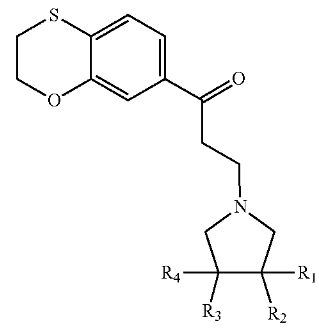

In this case the 1-(2,3-dihydro-1,4-benzoxathiin-7-yl) ethenone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 5

The synthesis of these sulfonyl analogs is similar starting from a suitable nitrile alcohol having the desired substitutions $R_1$, $R_2$, $R_3$, and $R_4$, as shown in Scheme 5 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl sulfonyl derivative and formaldehyde leads to the desired adduct after purification.

Scheme 5

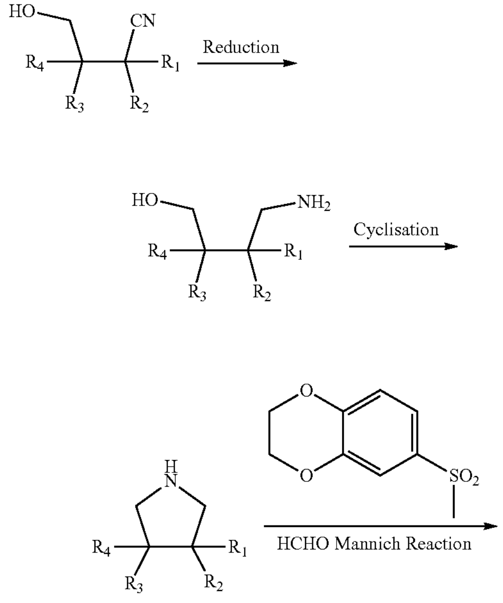

-continued

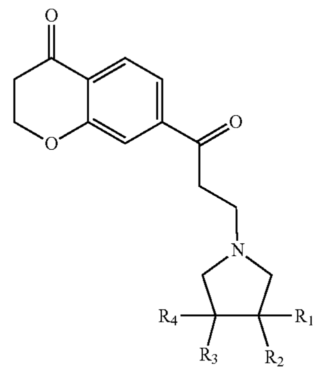

The 6-methylsulfonyl-2,3-dihydro-1,4-benzodioxine used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 6

The synthesis of these analogs is similar starting from a suitable nitrile alcohol having the desired substitutions $R_1$, $R_2$, $R_3$, and $R_4$, as shown in Scheme 6 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 6

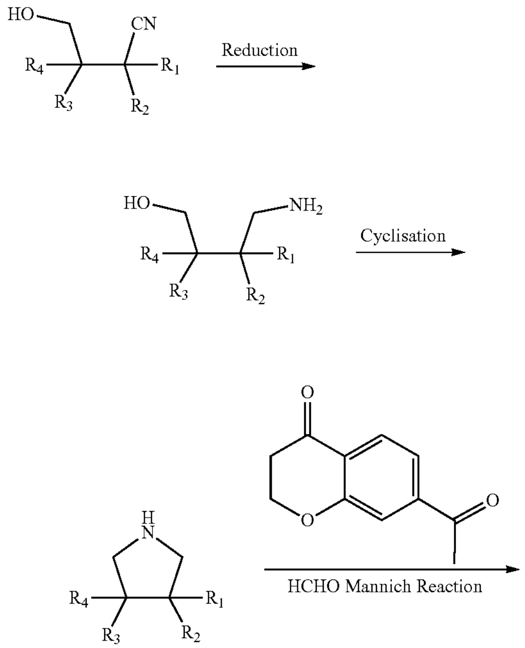

-continued

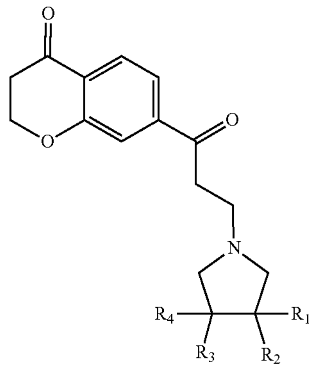

In this case the 7-acetylchroman-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 7

The synthesis of these analogs is similar starting from a suitable nitrile alcohol having the desired substitutions $R_1$, $R_2$, $R_3$, and $R_4$, as shown in Scheme 7 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 7

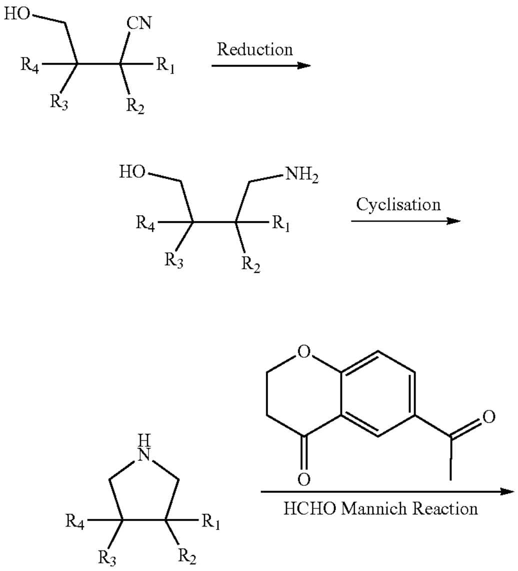

-continued

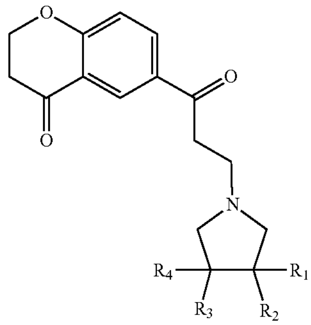

In this case the 6-acetylchroman-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 8

The synthesis of these analogs is similar starting from a suitable nitrile alcohol having the desired substitutions $R_1$, $R_2$, $R_3$, and $R_4$, as shown in Scheme 8 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 8

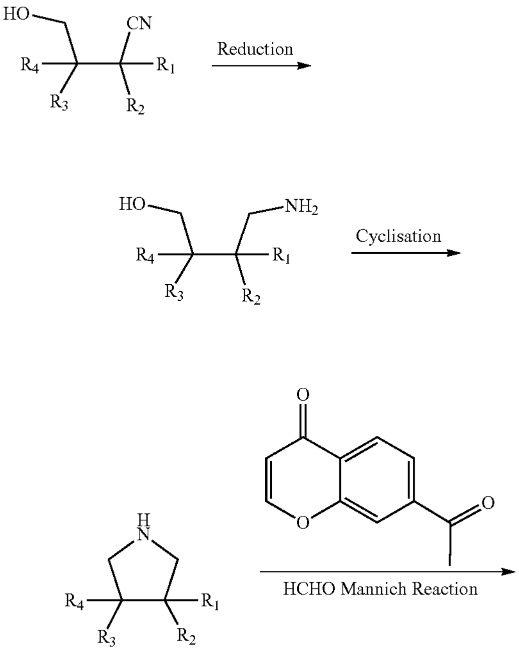

-continued

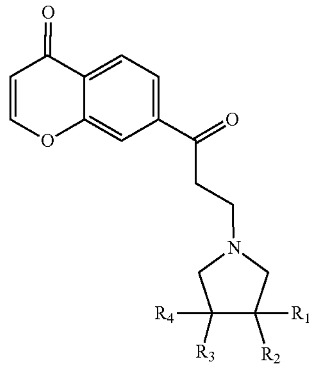

In this case the 7-acetylchromen-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 9

The synthesis of these analogs is similar starting from a suitable nitrile alcohol having the desired substitutions $R_1$, $R_2$, $R_3$, and $R_4$, as shown in Scheme 9 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 9

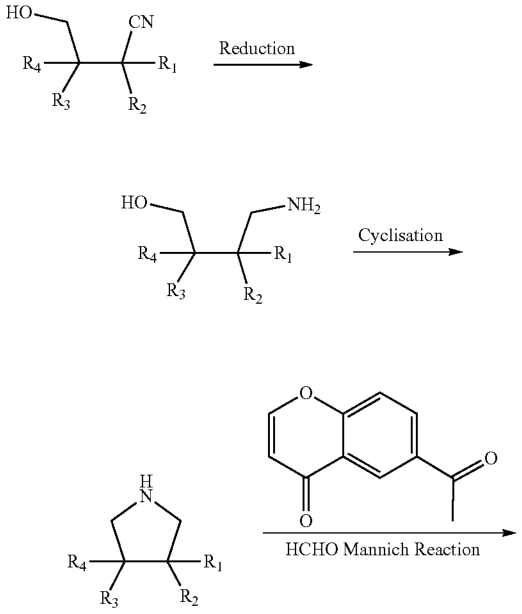

-continued

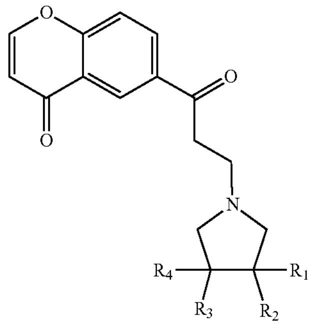

In this case the 6-acetylchromen-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 10

The synthesis of these analogs is similar starting from a suitable nitrile alcohol having the desired substitutions $R_1$, $R_2$, $R_3$, and $R_4$, as shown in Scheme 10 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 10

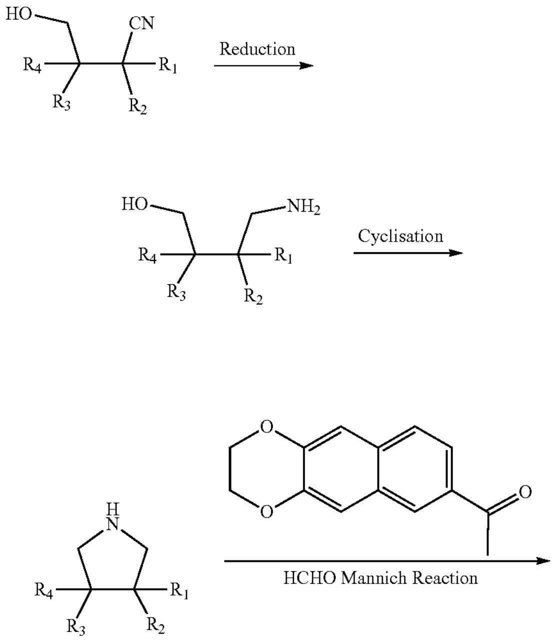

-continued

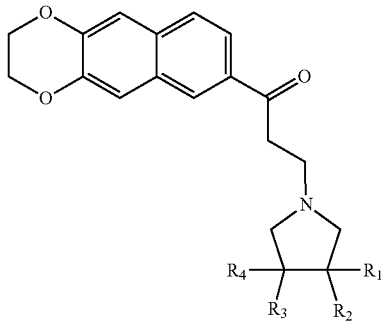

In this case the 1-(2,3-dihydrobenzo[g][1,4]benzodioxin-7-yl) ethenone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 11

The synthesis of these analogs is similar starting from a suitable nitrile alcohol having the desired substitutions $R_1$, $R_2$, $R_3$, and $R_4$, as shown in Scheme 11 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 11

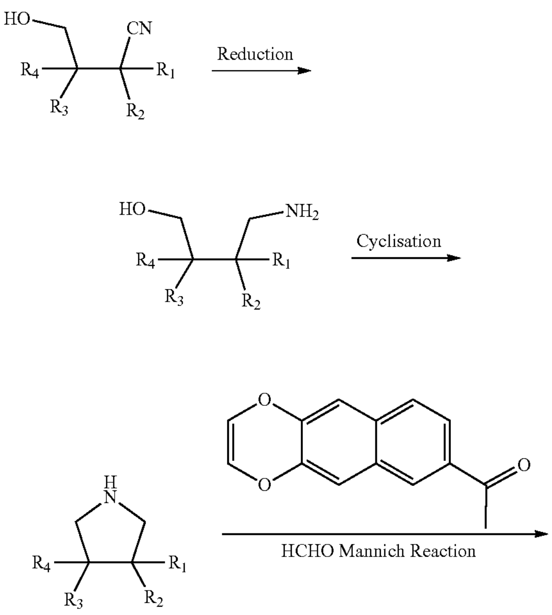

-continued

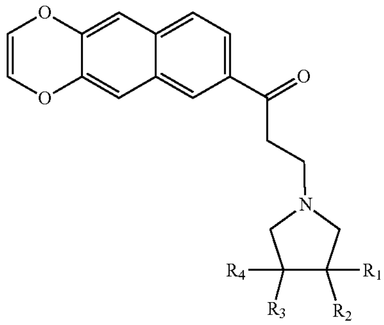

In this case the 1-benzo[g][1,4]benzodioxin-7-ylethanone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 12

The synthesis of these analogs is similar starting from a suitable nitrile alcohol having the desired substitutions $R_1$, $R_2$, $R_3$, and $R_4$, as shown in Scheme 12 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 12

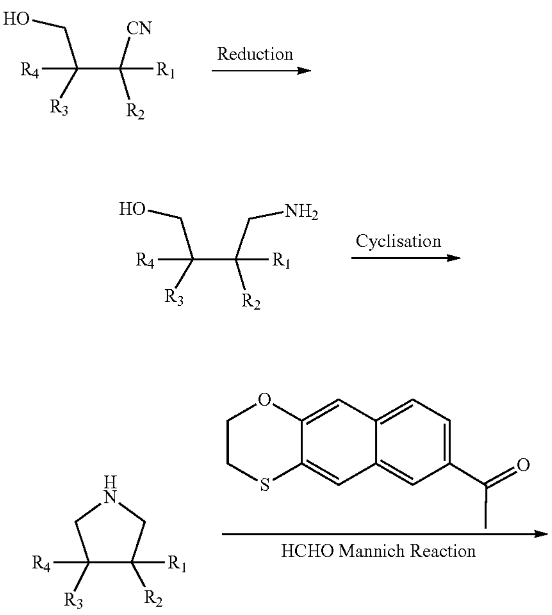

-continued

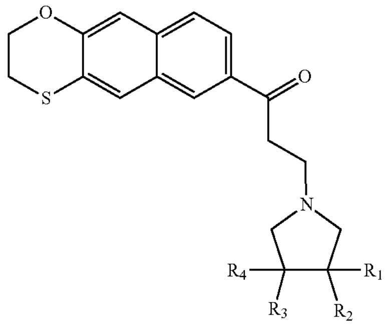

In this case the 1-(2,3-dihydrobenzo[g][1,4]benzoxathiin-7-yl) ethenone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 13

The synthesis of these analogs is similar starting from a suitable nitrile alcohol having the desired substitutions $R_1$, $R_2$, $R_3$, and $R_4$, as shown in Scheme 13 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 13

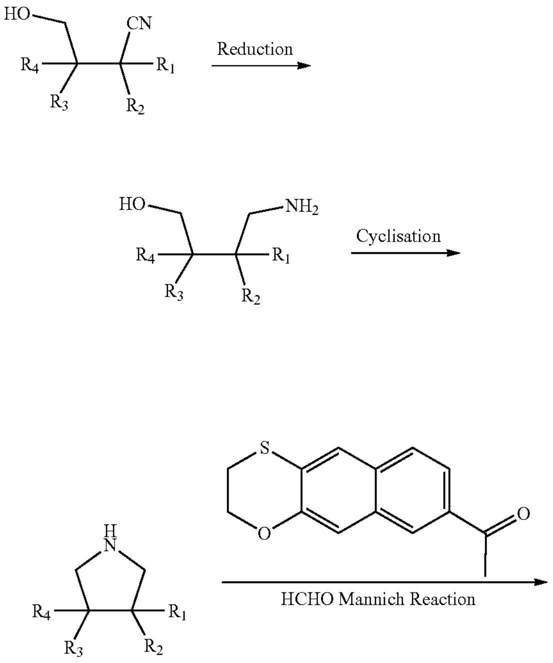

-continued

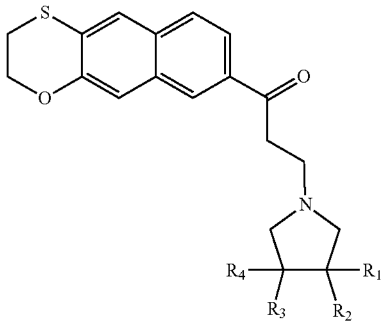

In this case the 1-(2,3-dihydrobenzo[g][1,4]benzoxathiin-8-yl) ethanone used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 14

The synthesis of these analogs is similar starting from a suitable nitrile alcohol having the desired substitutions $R_1$, $R_2$, $R_3$, and $R_4$, as shown in Scheme 14 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 14

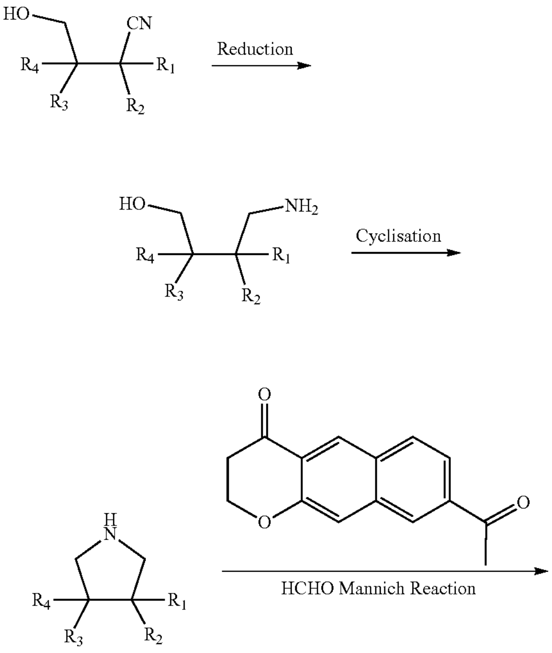

-continued

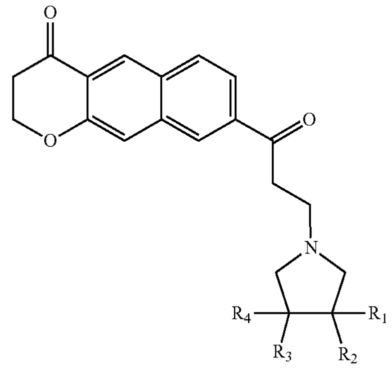

In this case the 8-acetyl-2,3-dihydrobenzo[g]chromen-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 15

The synthesis of these analogs is similar starting from a suitable nitrile alcohol having the desired substitutions $R_1$, $R_2$, $R_3$, and $R_4$, as shown in Scheme 15 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 15

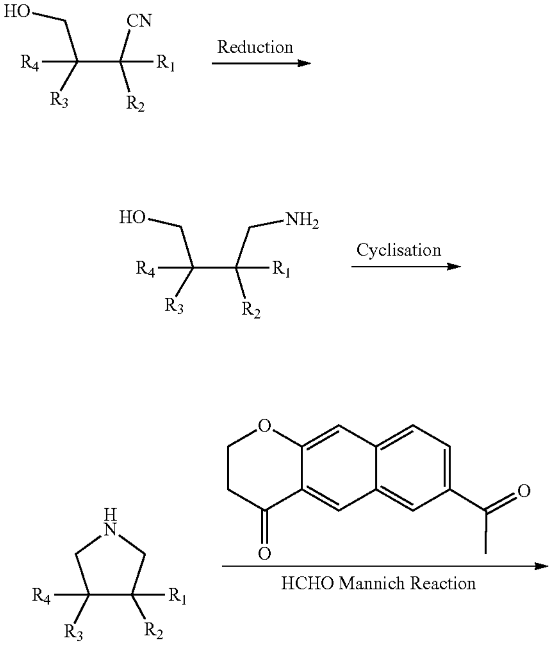

-continued

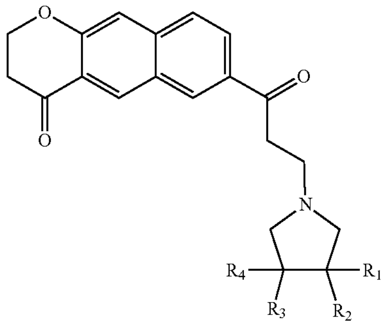

In this case the 7-acetyl-2,3-dihydrobenzo[g]chromen-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 16

The synthesis of these analogs is similar starting from a suitable nitrile alcohol having the desired substitutions $R_1$, $R_2$, $R_3$, and $R_4$, as shown in Scheme 16 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 16

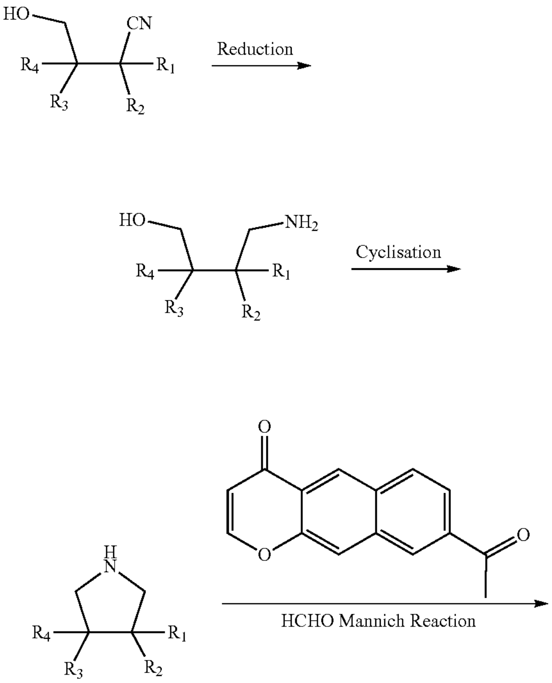

-continued

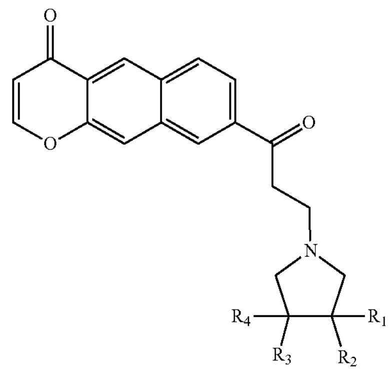

In this case the 8-acetylbenzo[g]chromen-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 17

The synthesis of these analogs is similar starting from a suitable nitrile alcohol having the desired substitutions $R_1$, $R_2$, $R_3$, and $R_4$, as shown in Scheme 17 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 17

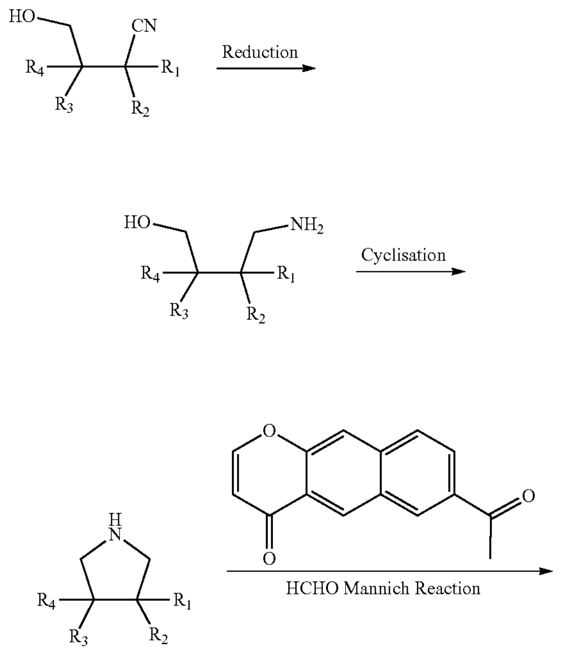

-continued

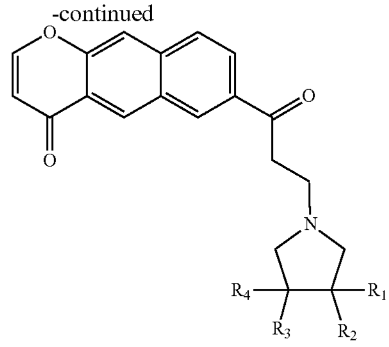

In this case the 7-acetylbenzo[g]chromen-4-one used in the Mannich Reaction final step can be appropriately substituted if required. Enantiomers are available from chiral HPLC methods or classical diastereomeric salt formation and crystallization.

Double bond analogs in the linker D (Formula I) can be generated from the Mannich products using standard synthetic organic chemistry well known to those skilled in the art.

The Analogs in Table 18

The synthesis of these analogs is similar starting from a suitable nitrile alcohol having the desired substitutions $R_1$, $R_2$, $R_3$, and $R_4$, as shown in Scheme 18 below. For reduction of the CN to $CH_2NH_2$ an aluminum Hydride such as $LIAlH_4$ is preferred. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 18

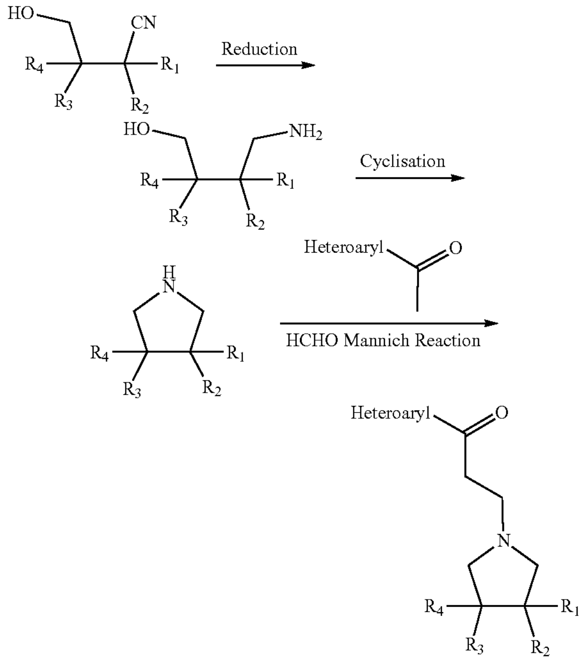

In this case the Heteroarylmethyl ketone used in the Mannich Reaction final step can be appropriately substituted if required. Enantiomers are available from chiral HPLC methods or classical diastereomeric salt formation and crystallization.

Some analogs which do not quite fit the Mannich pathway can be synthesized using standard synthetic organic chemistry well known to those skilled in the art.

Synthesis of Analogs in Table 19

Beginning with a suitable nitrile alcohol having the desired substitutions $R_1$, $R_2$, $R_3$, and $R_4$, as shown in Scheme 19 below, reduction of the CN to $CH_2NH_2$ can be achieved using an Aluminum Hydride such as $LIAlH_4$ or catalytic Hydrogenation with Hydrogen over Raney Nickel, Palladium Black or $PtO_2$. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 19

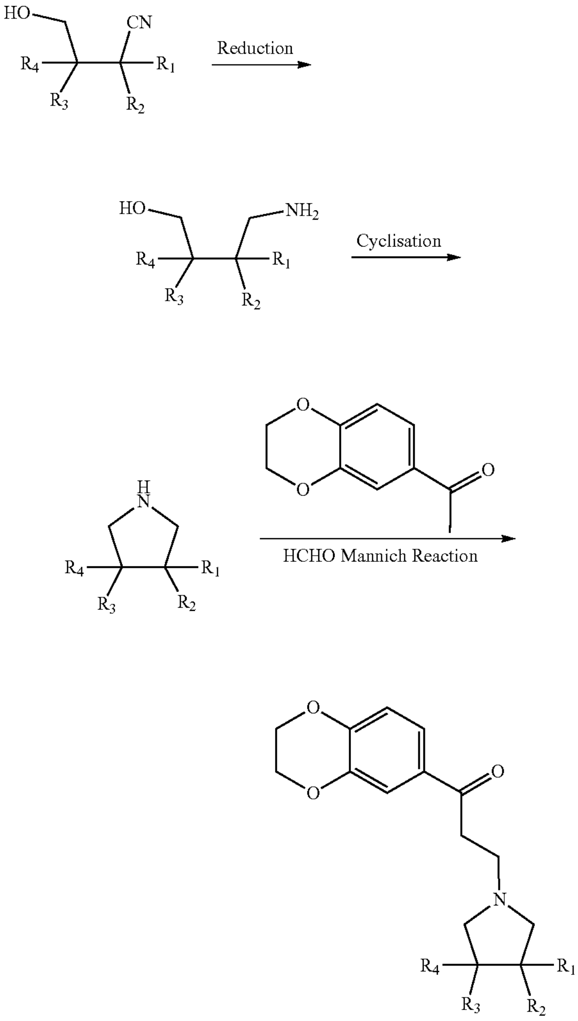

The 1-(2,3-dihydro-1,4-benzodioxin-6-yl) ethenone used in the Mannich Reaction final step can be appropriately substituted if required. Enantiomers are available from chiral HPLC methods or classical diastereomeric salt formation and crystallization.

Some analogs which do not quite fit the Mannich pathway can be synthesized using standard synthetic organic chemistry well known to those skilled in the art.

Synthesis of Analogs in Table 20

Beginning with a suitable nitrile alcohol having the desired substitutions $R_1$, $R_2$, $R_3$, and $R_4$, as shown in Scheme 20 below, reduction of the CN to $CH_2NH_2$ can be achieved using an aluminum Hydride such as $LIAlH_4$ or catalytic Hydrogenation with Hydrogen over Raney Nickel, Palladium Black or $PtO_2$. The resulting amino alcohol may spontaneously cyclize to the pyrrolidine or may require some help such as a trace of acid catalysis. A Mannich reaction between the pyrrolidine, the appropriate aryl methyl ketone and formaldehyde leads to the desired adduct after purification.

Scheme 1

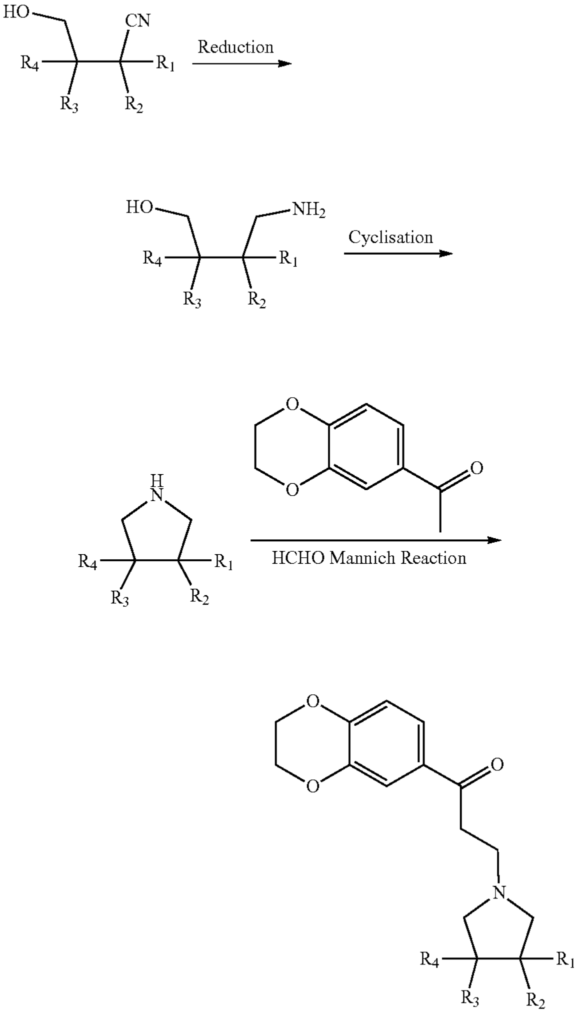

The 1-(2,3-dihydro-1,4-benzodioxin-6-yl) ethenone used in the Mannich Reaction final step can be appropriately substituted if required. Enantiomers are available from chiral HPLC methods or classical diastereomeric salt formation and crystallization.

Some analogs which do not quite fit the Mannich pathway can be synthesized using standard synthetic organic chemistry well known to those skilled in the art.

The following Tables 1 through 20 illustrate the analogs prepared.

TABLE 1
| Structure | |
|---|---|
| 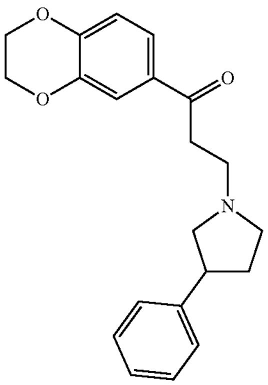 | 1) |
| 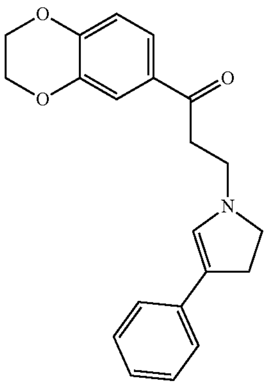 | 2) |
| 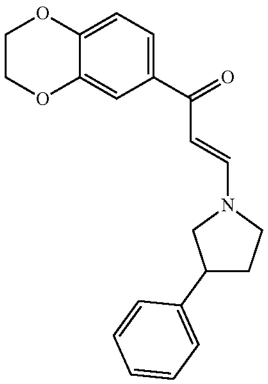 | 3) |
| 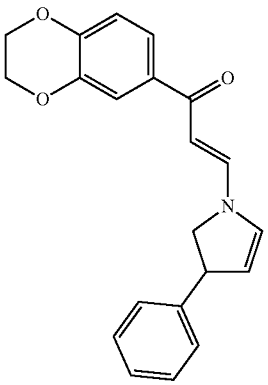 [SMILES: O=C(/C=C/N1C=CC(c2ccccc2)C1)c1ccc2c(c1)OCCO2] | 4) |
TABLE 1-continued
| Structure | |
|---|---|
| 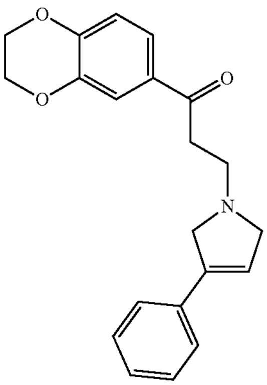 | 5) |
| 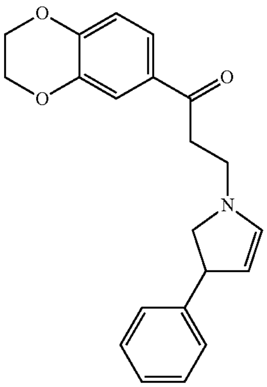 | 6) |
| 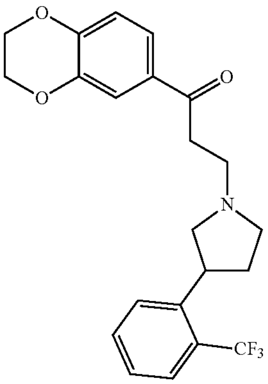 [SMILES: O=C(CCN1CCC(c2ccccc2C(F)(F)F)C1)c1ccc2c(c1)OCCO2] | 7) |
| 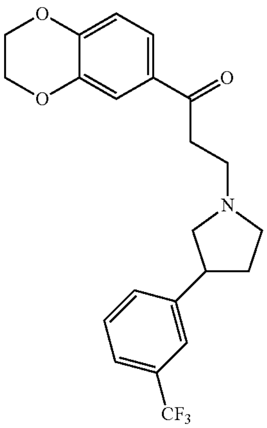 | 8) |

TABLE 1-continued
| Structure | |
|---|---|
| 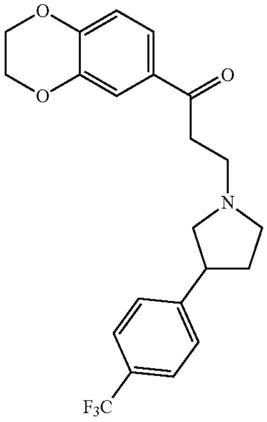 | 9) |
| 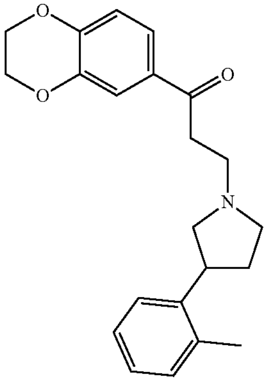 [SMILES: Cc1ccccc1C1CCN(CCC(=O)c2ccc3c(c2)OCCO3)C1] | 10) |
| 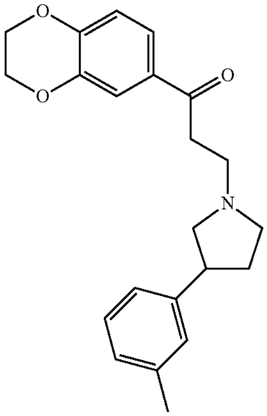 [SMILES: Cc1cccc(C2CCN(CCC(=O)c3ccc4c(c3)OCCO4)C2)c1] | 11) |
| 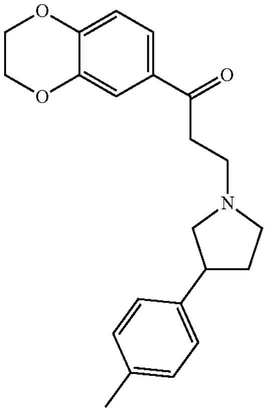 [SMILES: Cc1ccc(C2CCN(CCC(=O)c3ccc4c(c3)OCCO4)C2)cc1] | 12) |
| 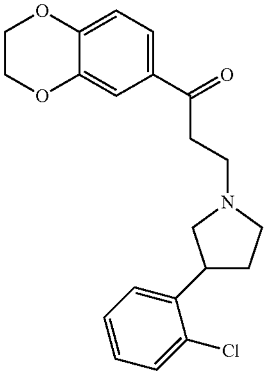 | 13) |
| 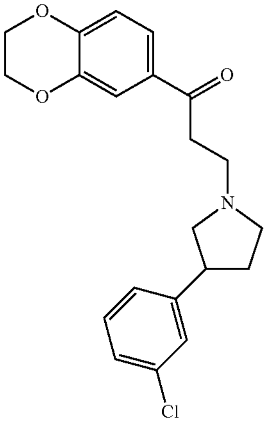 [SMILES: O=C(CCN1CCC(c2cccc(Cl)c2)C1)c1ccc2c(c1)OCCO2] | 14) |
| 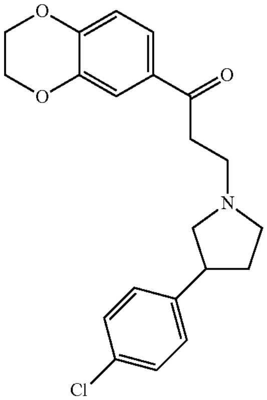 [SMILES: O=C(CCN1CCC(c2ccc(Cl)cc2)C1)c1ccc2c(c1)OCCO2] | 15) |

TABLE 1-continued
| Structure | |
|---|---|
| 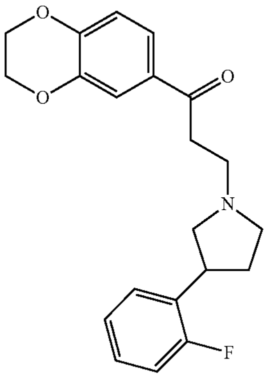 | 16) |
| 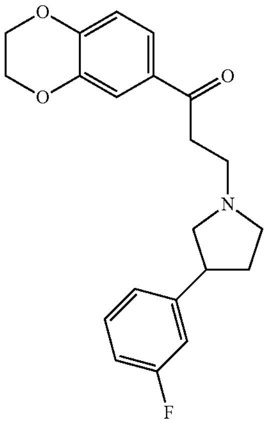 [SMILES: O=C(CCN1CCC(c2cccc(F)c2)C1)c1ccc2c(c1)OCCO2] | 17) |
| 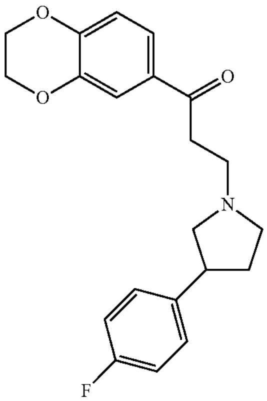 | 18) |
| 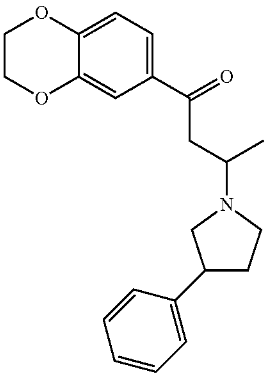 | 19) |
TABLE 1-continued
| Structure | |
|---|---|
| 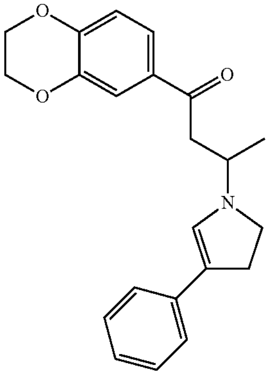 [SMILES: CC(CC(=O)c1ccc2c(c1)OCCO2)N1C=C(c2ccccc2)CC1] | 20) |
| 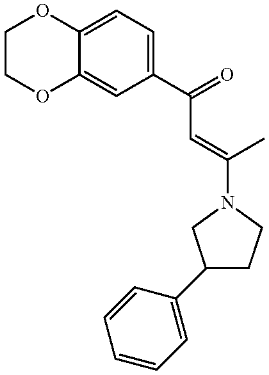 [SMILES: C/C(=C\C(=O)c1ccc2c(c1)OCCO2)N1CCC(c2ccccc2)C1] | 21) |
| 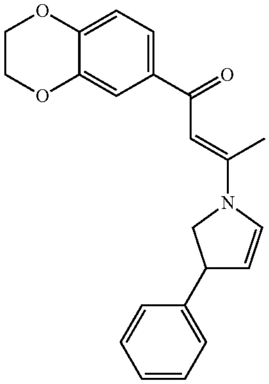 | 22) |
| 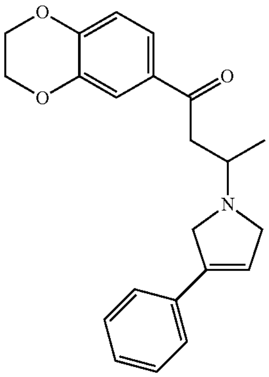 [SMILES: CC(CC(=O)c1ccc2c(c1)OCCO2)N1CC=C(c2ccccc2)C1] | 23) |

TABLE 1-continued
| Structure | |
|---|---|
| 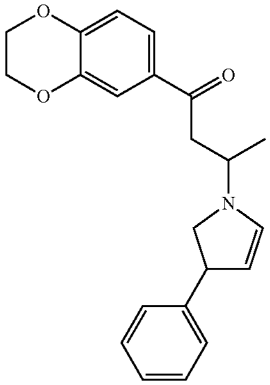 | 24) |
| 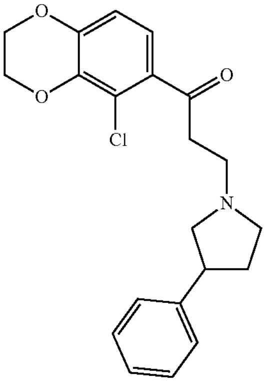 [SMILES: O=C(CCN1CCC(c2ccccc2)C1)c1ccc2c(c1Cl)OCCO2] | 25) |
| 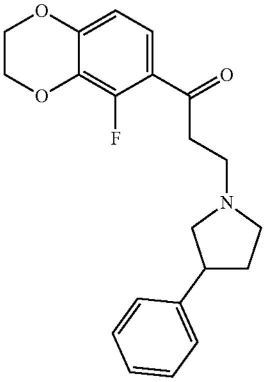 [SMILES: O=C(CCN1CCC(c2ccccc2)C1)c1ccc2c(c1F)OCCO2] | 26) |
| 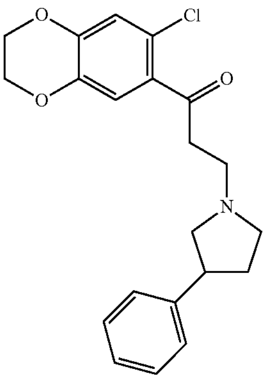 [SMILES: O=C(CCN1CCC(c2ccccc2)C1)c1cc2c(cc1Cl)OCCO2] | 27) |
TABLE 1-continued
| Structure | |
|---|---|
| 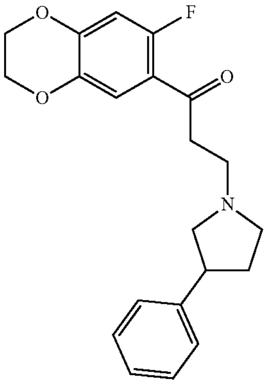 [SMILES: O=C(CCN1CCC(c2ccccc2)C1)c1cc2c(cc1F)OCCO2] | 28) |
| 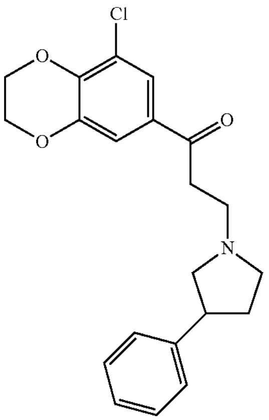 [SMILES: O=C(CCN1CCC(c2ccccc2)C1)c1cc(Cl)c2c(c1)OCCO2] | 29) |
| 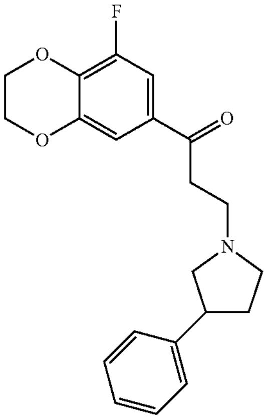 [SMILES: O=C(CCN1CCC(c2ccccc2)C1)c1cc(F)c2c(c1)OCCO2] | 30) |

TABLE 2
| Structure | |
|---|---|
| 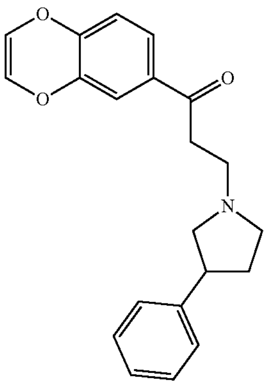 [SMILES: O=C(CCN1CCC(c2ccccc2)C1)c1ccc2c(c1)OC=CO2] | 31) |
| 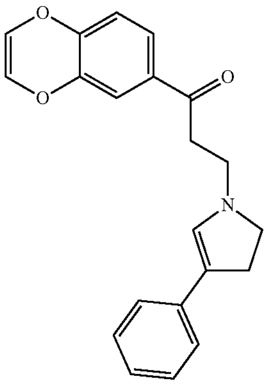 [SMILES: O=C(CCN1C=C(c2ccccc2)CC1)c1ccc2c(c1)OC=CO2] | 32) |
| 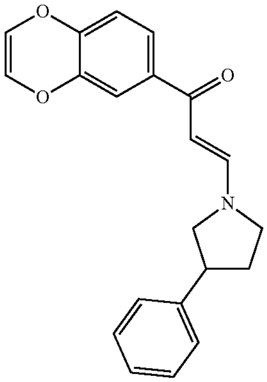 [SMILES: O=C(/C=C/N1CCC(c2ccccc2)C1)c1ccc2c(c1)OC=CO2] | 33) |
| 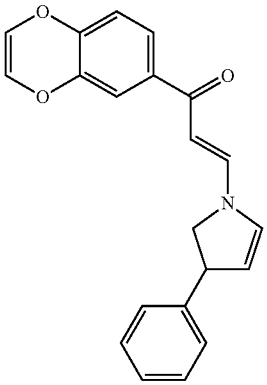 [SMILES: O=C(/C=C/N1C=CC(c2ccccc2)C1)c1ccc2c(c1)OC=CO2] | 34) |
TABLE 2-continued
| Structure | |
|---|---|
| 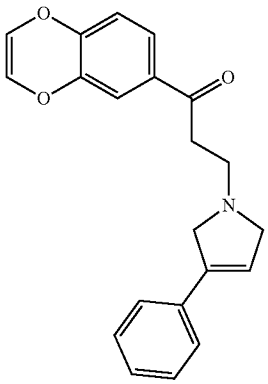 [SMILES: O=C(CCN1CC=C(c2ccccc2)C1)c1ccc2c(c1)OC=CO2] | 35) |
| 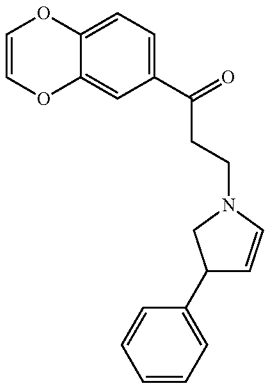 [SMILES: O=C(CCN1C=CC(c2ccccc2)C1)c1ccc2c(c1)OC=CO2] | 36) |
| 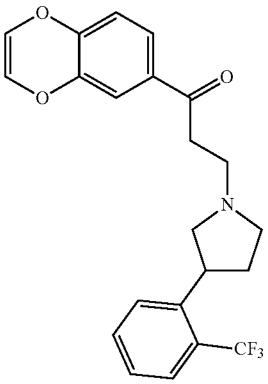 [SMILES: O=C(CCN1CCC(c2ccccc2C(F)(F)F)C1)c1ccc2c(c1)OC=CO2] | 37) |
| 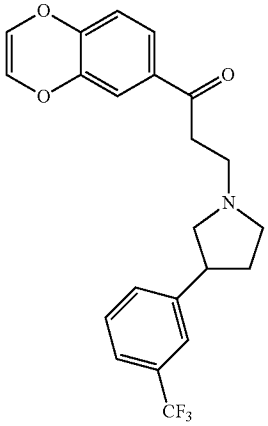 [SMILES: O=C(CCN1CCC(c2cccc(C(F)(F)F)c2)C1)c1ccc2c(c1)OC=CO2] | 38) |

TABLE 2-continued
| Structure | |
|---|---|
| 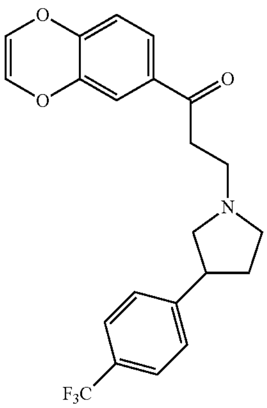 [SMILES: O=C(CCN1CCC(c2ccc(C(F)(F)F)cc2)C1)c1ccc2c(c1)OC=CO2] | 39) |
| 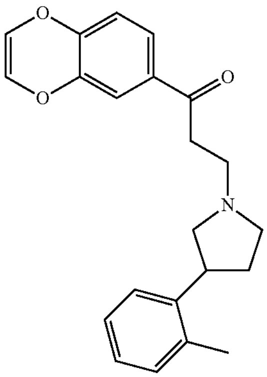 [SMILES: Cc1ccccc1C1CCN(CCC(=O)c2ccc3c(c2)OC=CO3)C1] | 40) |
| 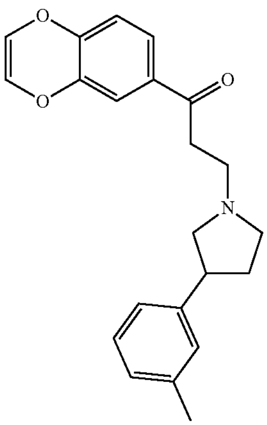 [SMILES: Cc1cccc(C2CCN(CCC(=O)c3ccc4c(c3)OC=CO4)C2)c1] | 41) |
TABLE 2-continued
| Structure | |
|---|---|
| 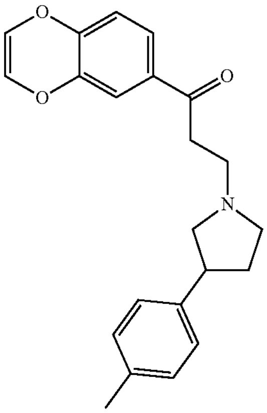 [SMILES: Cc1ccc(C2CCN(CCC(=O)c3ccc4c(c3)OC=CO4)C2)cc1] | 42) |
| 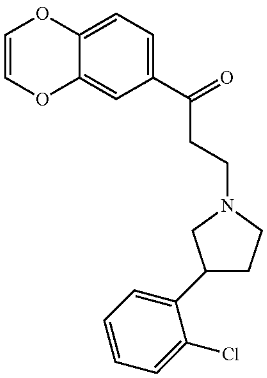 | 43) |
| 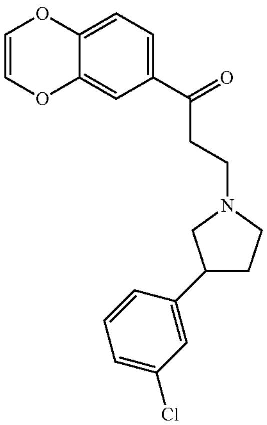 [SMILES: O=C(CCN1CCC(c2cccc(Cl)c2)C1)c1ccc2c(c1)OC=CO2] | 44) |
| 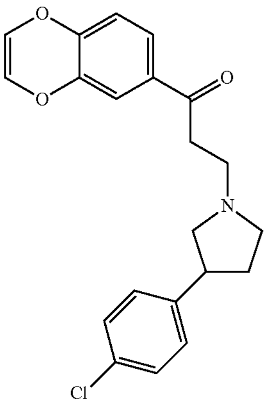 [SMILES: O=C(CCN1CCC(c2ccc(Cl)cc2)C1)c1ccc2c(c1)OC=CO2] | 45) |

TABLE 2-continued
| Structure | |
|---|---|
| 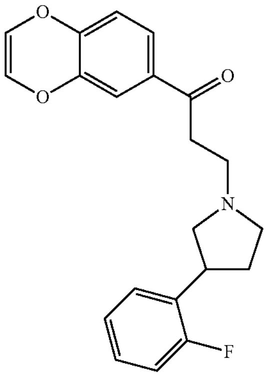 [SMILES: O=C(CCN1CCC(c2ccccc2F)C1)c1ccc2c(c1)OC=CO2] | 46) |
| 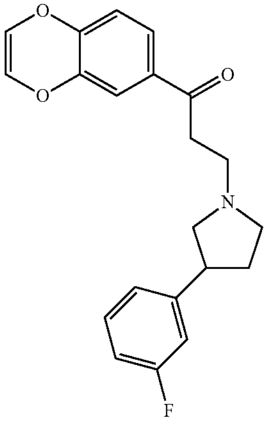 [SMILES: O=C(CCN1CCC(c2cccc(F)c2)C1)c1ccc2c(c1)OC=CO2] | 47) |
| 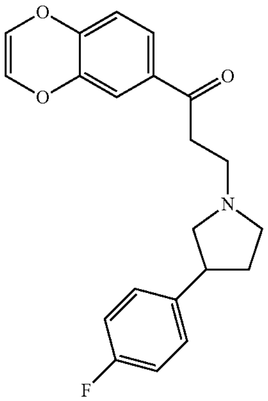 [SMILES: O=C(CCN1CCC(c2ccc(F)cc2)C1)c1ccc2c(c1)OC=CO2] | 48) |
| 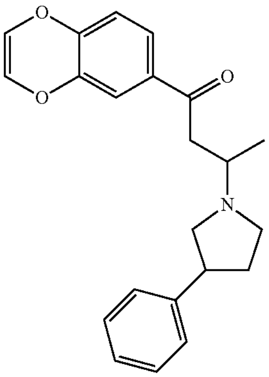 [SMILES: CC(CC(=O)c1ccc2c(c1)OC=CO2)N1CCC(c2ccccc2)C1] | 49) |
TABLE 2-continued
| Structure | |
|---|---|
| 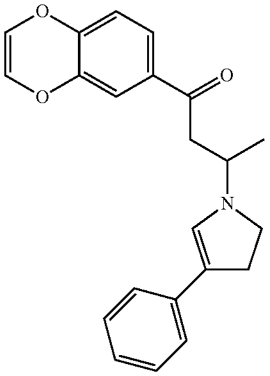 [SMILES: CC(CC(=O)c1ccc2c(c1)OC=CO2)N1C=C(c2ccccc2)CC1] | 50) |
| 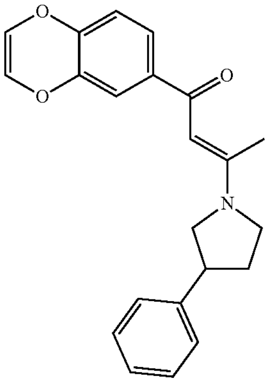 [SMILES: C/C(=C\C(=O)c1ccc2c(c1)OC=CO2)N1CCC(c2ccccc2)C1] | 51) |
| 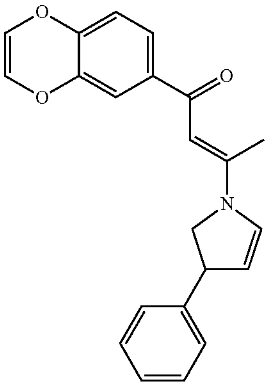 [SMILES: C/C(=C\C(=O)c1ccc2c(c1)OC=CO2)N1C=CC(c2ccccc2)C1] | 52) |
| 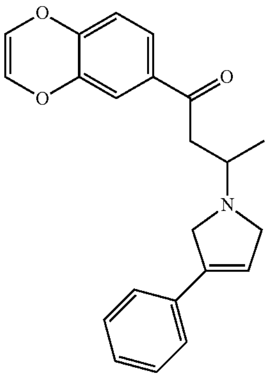 [SMILES: CC(CC(=O)c1ccc2c(c1)OC=CO2)N1CC=C(c2ccccc2)C1] | 53) |

TABLE 2-continued
| Structure |
| --- |
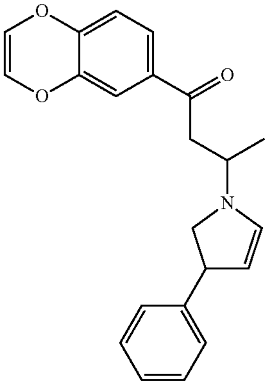 [SMILES: CC(CC(=O)c1ccc2c(c1)OC=CO2)N1C=CC(c2ccccc2)C1]
54)
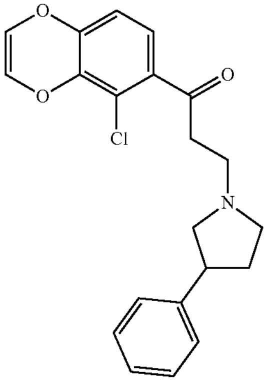 [SMILES: O=C(CCN1CCC(c2ccccc2)C1)c1ccc2c(c1Cl)OC=CO2]
55)
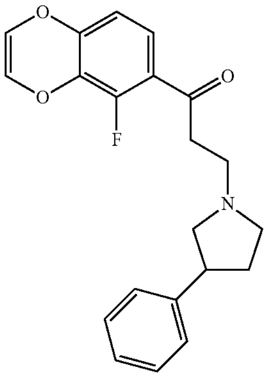 [SMILES: O=C(CCN1CCC(c2ccccc2)C1)c1ccc2c(c1F)OC=CO2]
56)
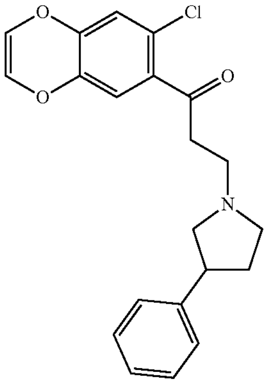
57)
TABLE 2-continued
| Structure |
| --- |
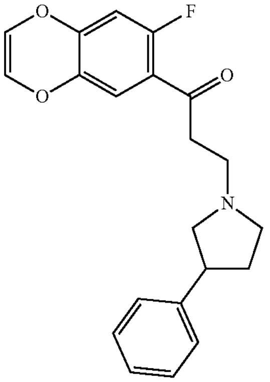 [SMILES: O=C(CCN1CCC(c2ccccc2)C1)c1cc2c(cc1F)OC=CO2]
58)
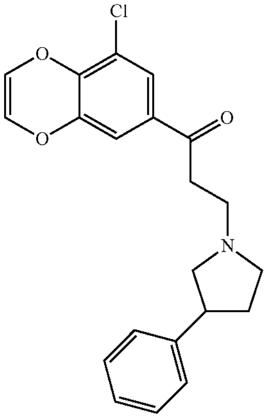 [SMILES: O=C(CCN1CCC(c2ccccc2)C1)c1cc(Cl)c2c(c1)OC=CO2]
59)
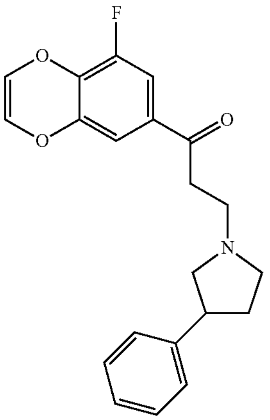 [SMILES: O=C(CCN1CCC(c2ccccc2)C1)c1cc(F)c2c(c1)OC=CO2]
60)

TABLE 3
| Structure | |
|---|---|
| 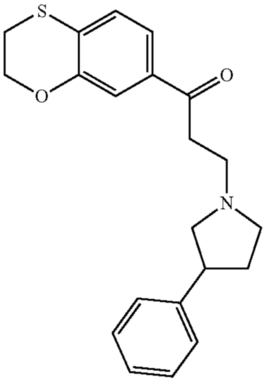 [SMILES: O=C(CCN1CCC(c2ccccc2)C1)c1ccc2c(c1)OCCS2] | 61) |
| 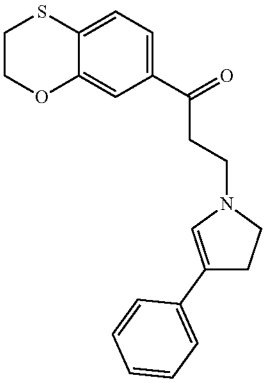 [SMILES: O=C(CCN1C=C(c2ccccc2)CC1)c1ccc2c(c1)OCCS2] | 62) |
| 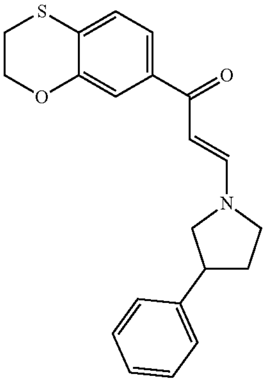 [SMILES: O=C(/C=C/N1CCC(c2ccccc2)C1)c1ccc2c(c1)OCCS2] | 63) |
| 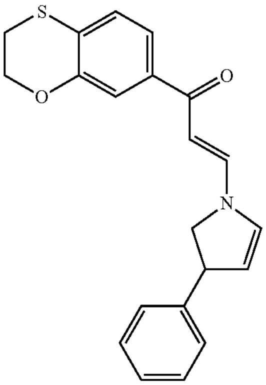 [SMILES: O=C(/C=C/N1C=CC(c2ccccc2)C1)c1ccc2c(c1)OCCS2] | 64) |
TABLE 3-continued
| Structure | |
|---|---|
| 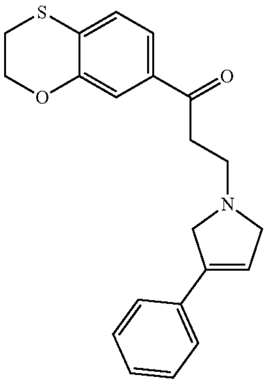 [SMILES: O=C(CCN1CC=C(c2ccccc2)C1)c1ccc2c(c1)OCCS2] | 65) |
| 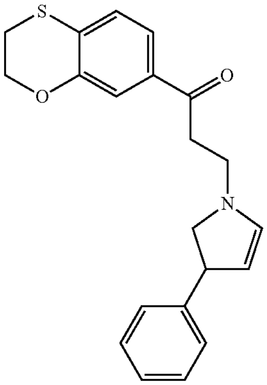 [SMILES: O=C(CCN1C=CC(c2ccccc2)C1)c1ccc2c(c1)OCCS2] | 66) |
| 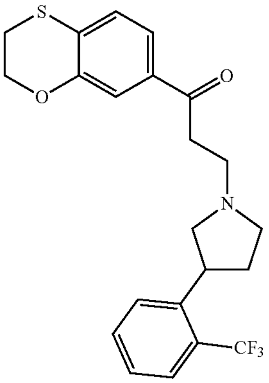 | 67) |
| 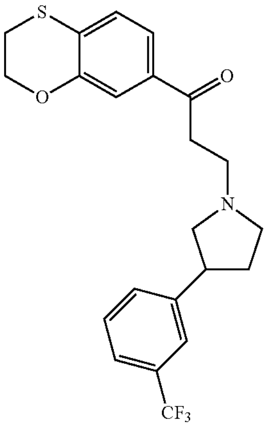 [SMILES: O=C(CCN1CCC(c2cccc(C(F)(F)F)c2)C1)c1ccc2c(c1)OCCS2] | 68) |

TABLE 3-continued
| Structure | |
|---|---|
| 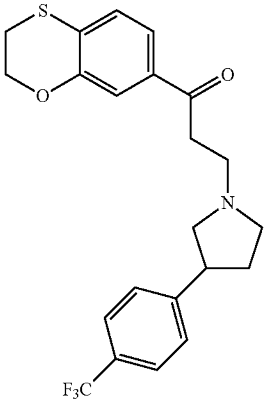 [SMILES: O=C(CCN1CCC(c2ccc(C(F)(F)F)cc2)C1)c1ccc2c(c1)OCCS2] | 69) |
| 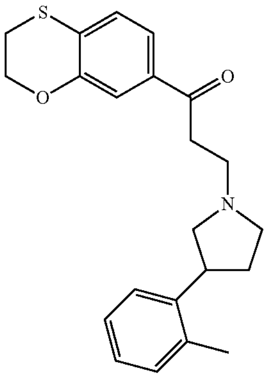 [SMILES: Cc1ccccc1C1CCN(CCC(=O)c2ccc3c(c2)OCCS3)C1] | 70) |
| 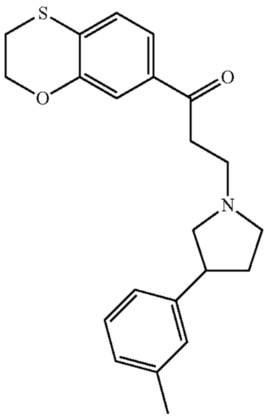 | 71) |
| 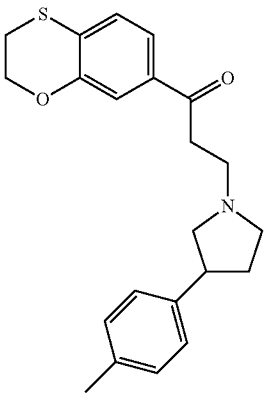 | 72) |
TABLE 3-continued
| Structure | |
|---|---|
| 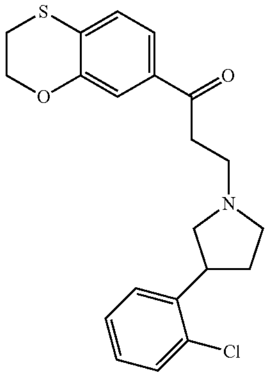 | 73) |
| 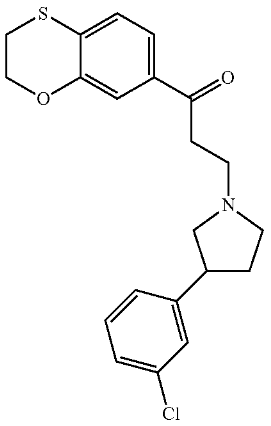 | 74) |
| 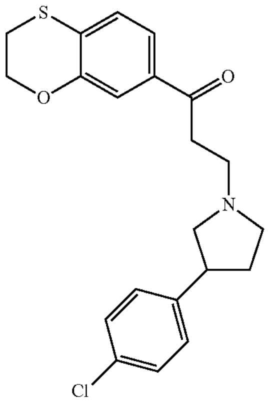 | 75) |
| 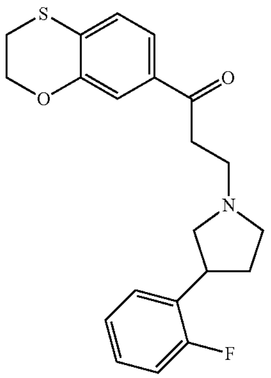 | 76) |

TABLE 3-continued
| Structure | |
|---|---|
| 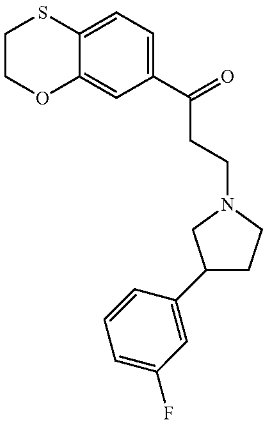 | 77) |
| 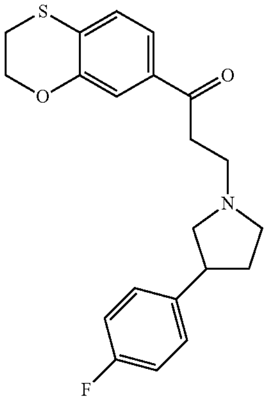 | 78) |
| 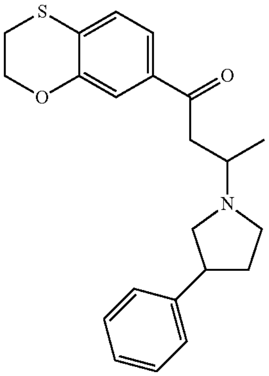 [SMILES: CC(CC(=O)c1ccc2c(c1)OCCS2)N1CCC(c2ccccc2)C1] | 79) |
| 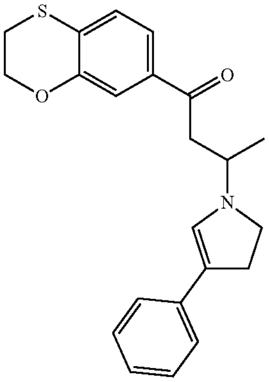 [SMILES: CC(CC(=O)c1ccc2c(c1)OCCS2)N1C=C(c2ccccc2)CC1] | 80) |
TABLE 3-continued
| Structure | |
|---|---|
| 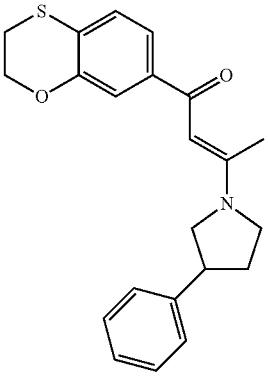 | 81) |
| 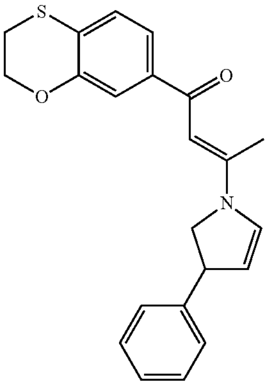 | 82) |
| 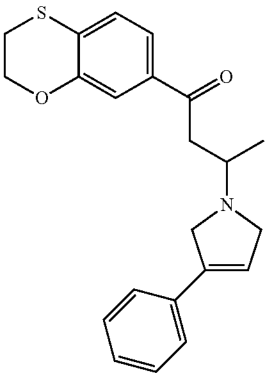 | 83) |
| 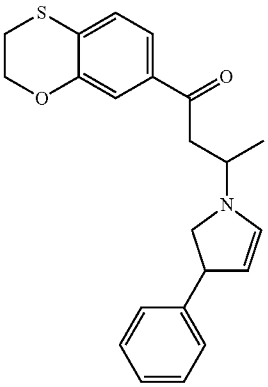 | 84) |

TABLE 3-continued
| Structure |
|---|
| 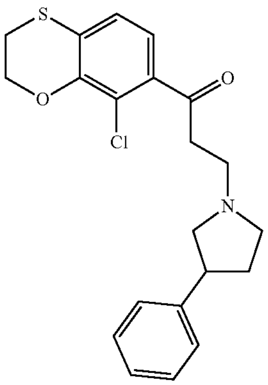 [SMILES: O=C(CCN1CCC(c2ccccc2)C1)c1ccc2c(c1Cl)OCCS2] 85) |
| 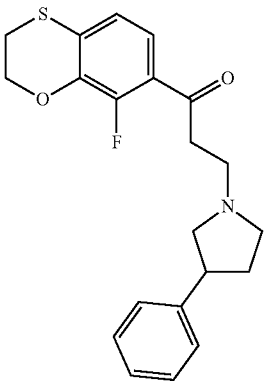 [SMILES: O=C(CCN1CCC(c2ccccc2)C1)c1ccc2c(c1F)OCCS2] 86) |
| 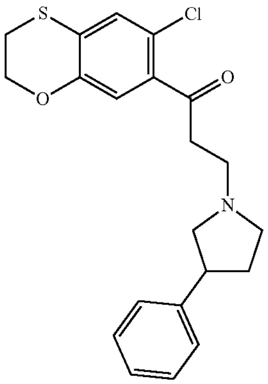 [SMILES: O=C(CCN1CCC(c2ccccc2)C1)c1cc2c(cc1Cl)SCCO2] 87) |
| 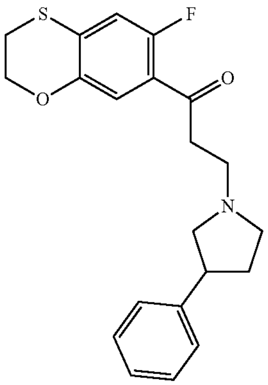 [SMILES: O=C(CCN1CCC(c2ccccc2)C1)c1cc2c(cc1F)SCCO2] 88) |
TABLE 3-continued
| Structure |
|---|
| 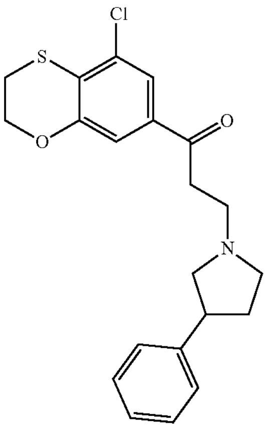 [SMILES: O=C(CCN1CCC(c2ccccc2)C1)c1cc(Cl)c2c(c1)OCCS2] 89) |
| 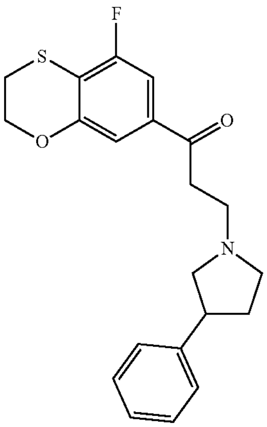 [SMILES: O=C(CCN1CCC(c2ccccc2)C1)c1cc(F)c2c(c1)OCCS2] 90) |
TABLE 4
| Structure |
|---|
| 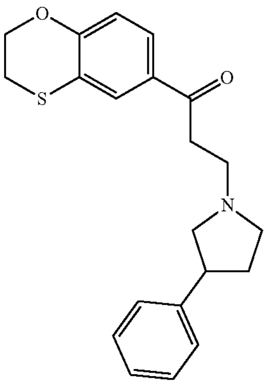 [SMILES: O=C(CCN1CCC(c2ccccc2)C1)c1ccc2c(c1)SCCO2] 91) |

TABLE 4-continued
| Structure |
| --- |
| 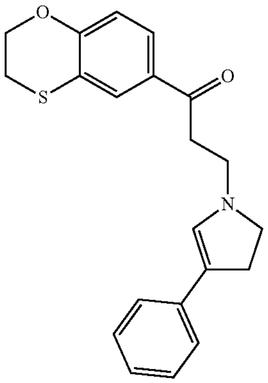 [SMILES: O=C(CCN1C=C(c2ccccc2)CC1)c1ccc2c(c1)SCCO2] 92) |
| 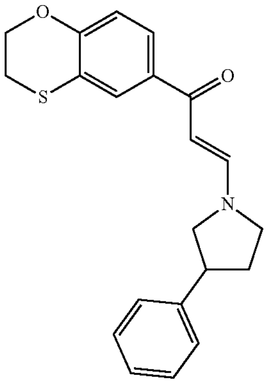 [SMILES: O=C(/C=C/N1CCC(c2ccccc2)C1)c1ccc2c(c1)SCCO2] 93) |
| 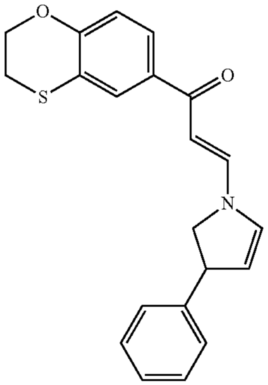 [SMILES: O=C(/C=C/N1C=CC(c2ccccc2)C1)c1ccc2c(c1)SCCO2] 94) |
| 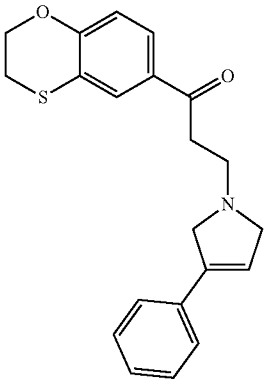 [SMILES: O=C(CCN1CC=C(c2ccccc2)C1)c1ccc2c(c1)SCCO2] 95) |
TABLE 4-continued
| Structure |
| --- |
| 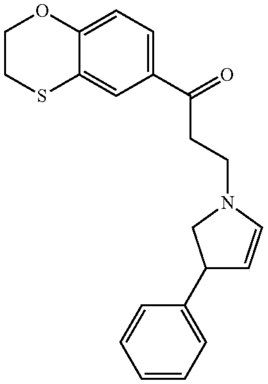 96) |
| 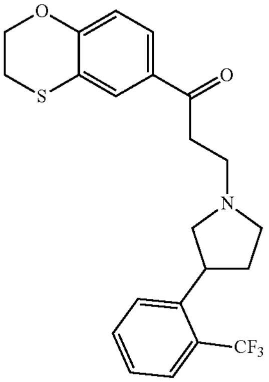 97) |
| 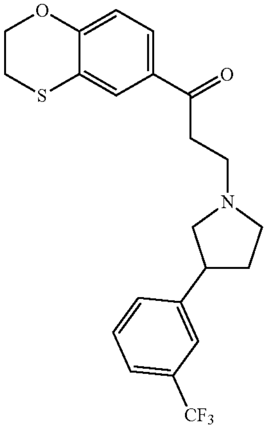 [SMILES: O=C(CCN1CCC(c2cccc(C(F)(F)F)c2)C1)c1ccc2c(c1)SCCO2] 98) |

TABLE 4-continued
| Structure |
|---|
| 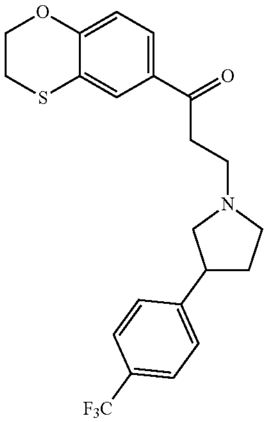 [SMILES: O=C(CCN1CCC(c2ccc(C(F)(F)F)cc2)C1)c1ccc2c(c1)SCCO2] 99) |
| 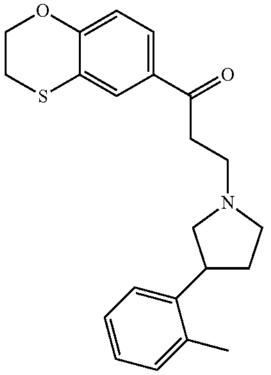 [SMILES: Cc1ccccc1C1CCN(CCC(=O)c2ccc3c(c2)SCCO3)C1] 100) |
| 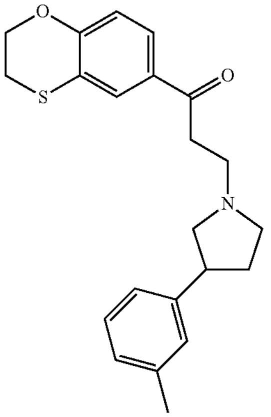 101) |
| 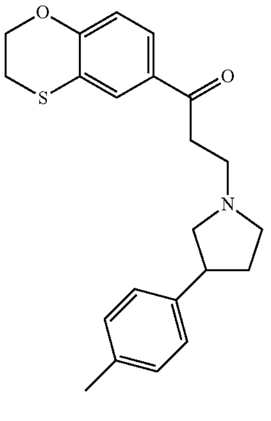 [SMILES: Cc1ccc(C2CCN(CCC(=O)c3ccc4c(c3)SCCO4)C2)cc1] 102) |
TABLE 4-continued
| Structure |
|---|
| 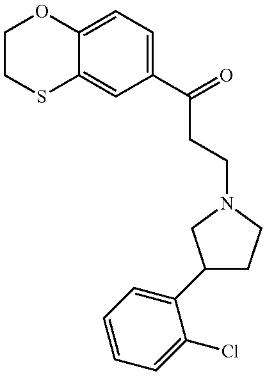 [SMILES: O=C(CCN1CCC(c2ccccc2Cl)C1)c1ccc2c(c1)SCCO2] 103) |
| 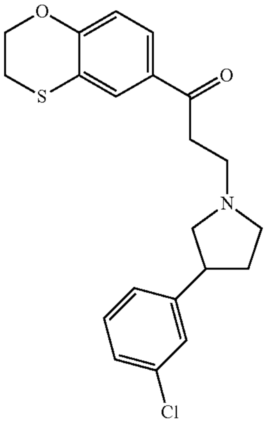 104) |
| 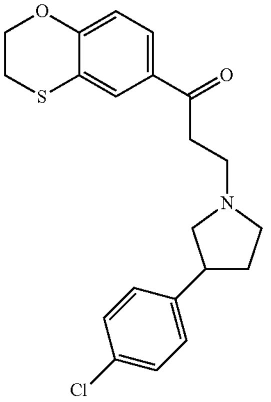 105) |
| 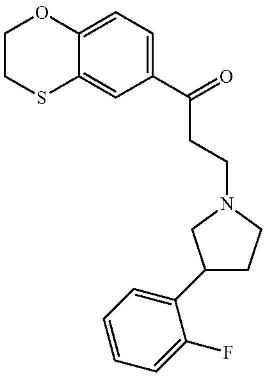 [SMILES: O=C(CCN1CCC(c2ccccc2F)C1)c1ccc2c(c1)SCCO2] 106) |

TABLE 4-continued
| Structure |
|---|
| 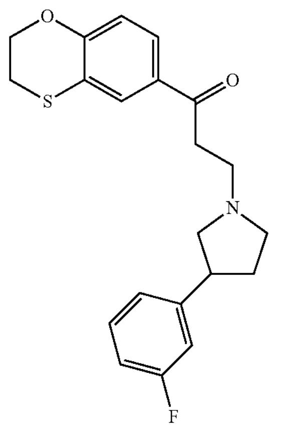 107) |
| 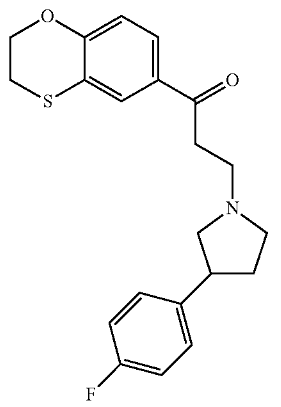 108) |
| 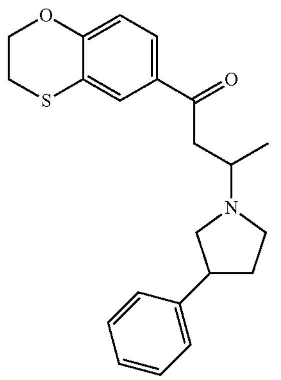 109) |
| 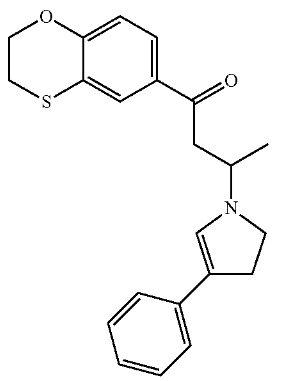 [SMILES: CC(CC(=O)c1ccc2c(c1)SCCO2)N1C=C(c2ccccc2)CC1] 110) |
TABLE 4-continued
| Structure |
|---|
| 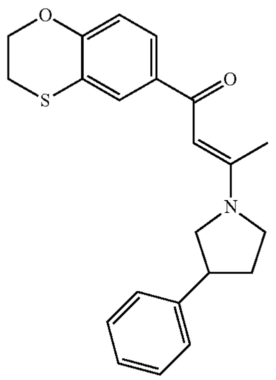 [SMILES: C/C(=C\C(=O)c1ccc2c(c1)SCCO2)N1CCC(c2ccccc2)C1] 111) |
| 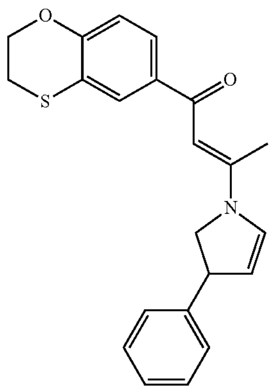 112) |
| 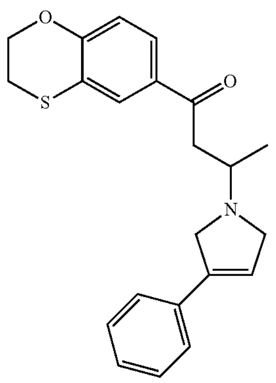 [SMILES: CC(CC(=O)c1ccc2c(c1)SCCO2)N1CC=C(c2ccccc2)C1] 113) |
| 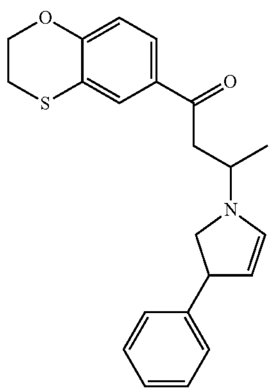 [SMILES: CC(CC(=O)c1ccc2c(c1)SCCO2)N1C=CC(c2ccccc2)C1] 114) |

TABLE 4-continued
| Structure |
| --- |
| 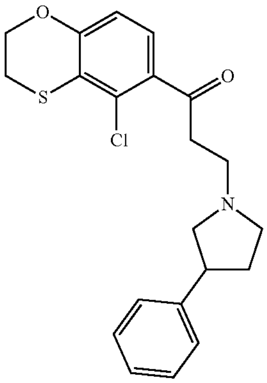 [SMILES: O=C(CCN1CCC(c2ccccc2)C1)c1ccc2c(c1Cl)SCCO2] 115) |
| 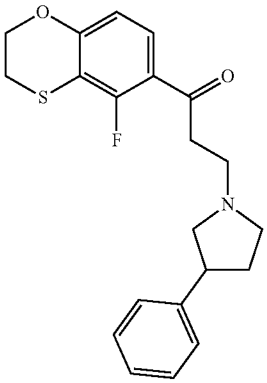 [SMILES: O=C(CCN1CCC(c2ccccc2)C1)c1ccc2c(c1F)SCCO2] 116) |
| 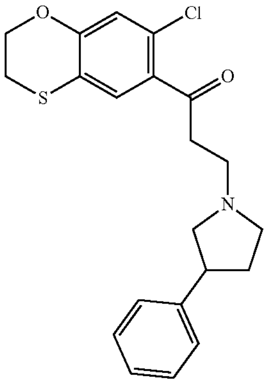 [SMILES: O=C(CCN1CCC(c2ccccc2)C1)c1cc2c(cc1Cl)OCCS2] 117) |
| 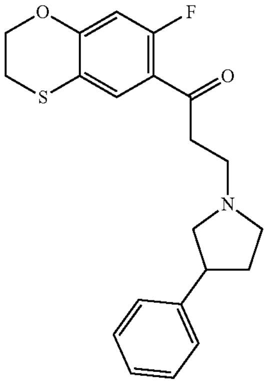 [SMILES: O=C(CCN1CCC(c2ccccc2)C1)c1cc2c(cc1F)OCCS2] 118) |
TABLE 4-continued
| Structure |
| --- |
| 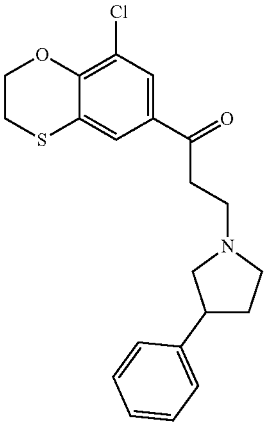 [SMILES: O=C(CCN1CCC(c2ccccc2)C1)c1cc(Cl)c2c(c1)SCCO2] 119) |
| 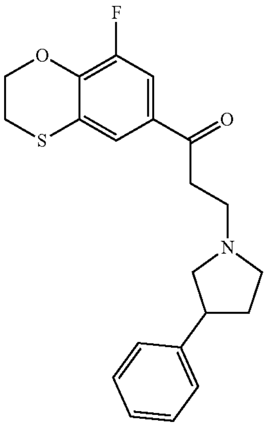 [SMILES: O=C(CCN1CCC(c2ccccc2)C1)c1cc(F)c2c(c1)SCCO2] 120) |
TABLE 5
| Structure |
| --- |
| 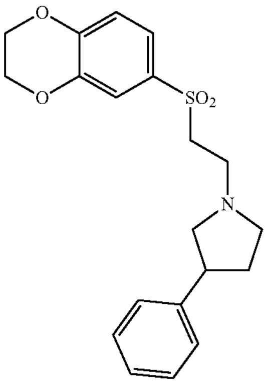 [SMILES: O=S(=O)(CCN1CCC(c2ccccc2)C1)c1ccc2c(c1)OCCO2] 121) |

TABLE 5-continued
| Structure | |
|---|---|
| 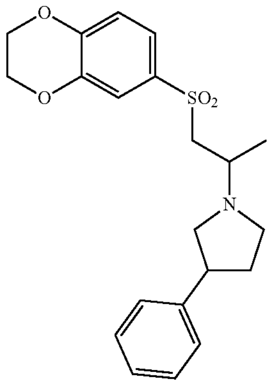 [SMILES: CC(CS(=O)(=O)c1ccc2c(c1)OCCO2)N1CCC(c2ccccc2)C1] | 122) |
| 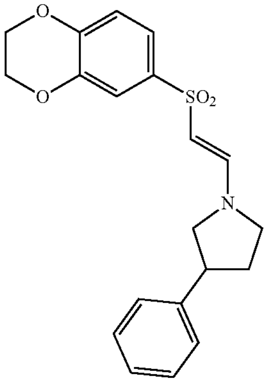 [SMILES: O=S(=O)(/C=C/N1CCC(c2ccccc2)C1)c1ccc2c(c1)OCCO2] | 123) |
| 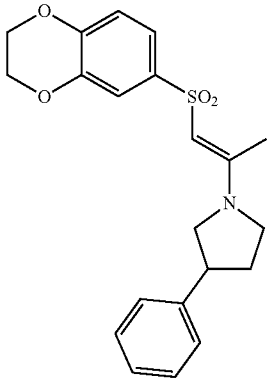 [SMILES: C/C(=C\S(=O)(=O)c1ccc2c(c1)OCCO2)N1CCC(c2ccccc2)C1] | 124) |
| 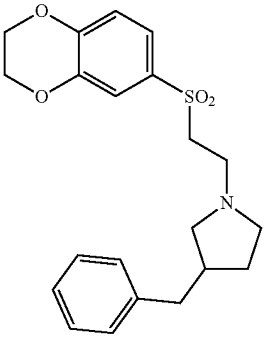 [SMILES: O=S(=O)(CCN1CCC(Cc2ccccc2)C1)c1ccc2c(c1)OCCO2] | 125) |
TABLE 5-continued
| Structure | |
|---|---|
| 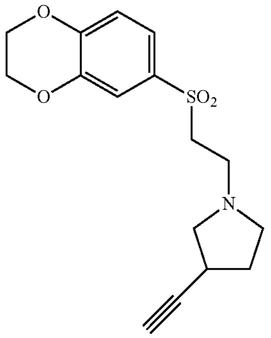 [SMILES: C#CC1CCN(CCS(=O)(=O)c2ccc3c(c2)OCCO3)C1] | 126) |
| 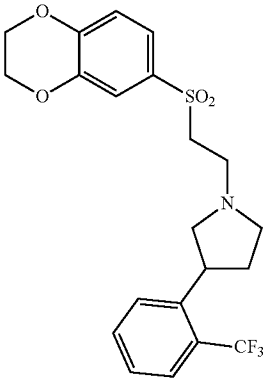 [SMILES: O=S(=O)(CCN1CCC(c2ccccc2C(F)(F)F)C1)c1ccc2c(c1)OCCO2] | 127) |
| 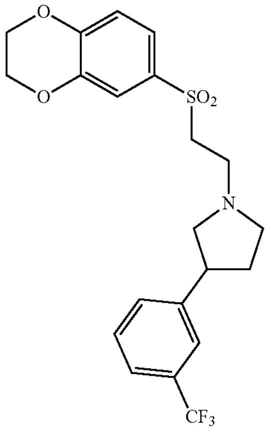 [SMILES: O=S(=O)(CCN1CCC(c2cccc(C(F)(F)F)c2)C1)c1ccc2c(c1)OCCO2] | 128) |
| 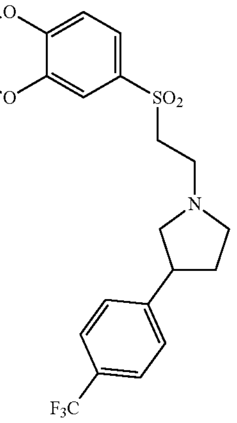 | 129) |

TABLE 5-continued
| Structure | |
|---|---|
| 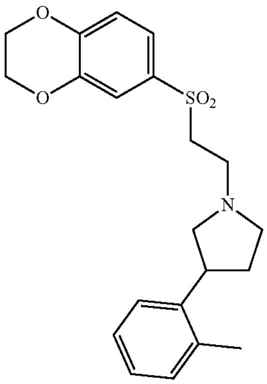 [SMILES: Cc1ccccc1C1CCN(CCS(=O)(=O)c2ccc3c(c2)OCCO3)C1] | 130) |
| 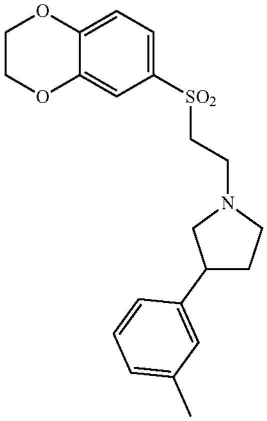 [SMILES: Cc1cccc(C2CCN(CCS(=O)(=O)c3ccc4c(c3)OCCO4)C2)c1] | 131) |
| 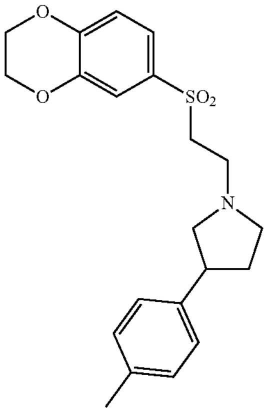 [SMILES: Cc1ccc(C2CCN(CCS(=O)(=O)c3ccc4c(c3)OCCO4)C2)cc1] | 132) |
| 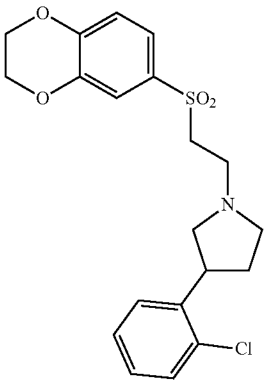 [SMILES: O=S(=O)(CCN1CCC(c2ccccc2Cl)C1)c1ccc2c(c1)OCCO2] | 133) |
TABLE 5-continued
| Structure | |
|---|---|
| 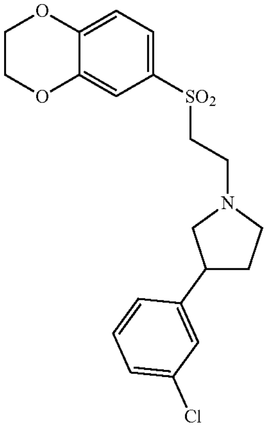 [SMILES: O=S(=O)(CCN1CCC(c2cccc(Cl)c2)C1)c1ccc2c(c1)OCCO2] | 134) |
| 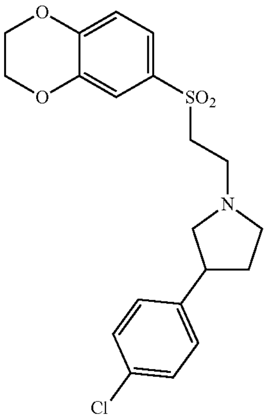 [SMILES: O=S(=O)(CCN1CCC(c2ccc(Cl)cc2)C1)c1ccc2c(c1)OCCO2] | 135) |
| 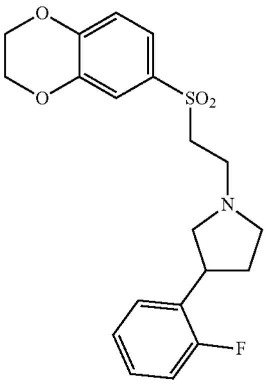 [SMILES: O=S(=O)(CCN1CCC(c2ccccc2F)C1)c1ccc2c(c1)OCCO2] | 136) |

TABLE 5-continued
| Structure | |
|---|---|
| 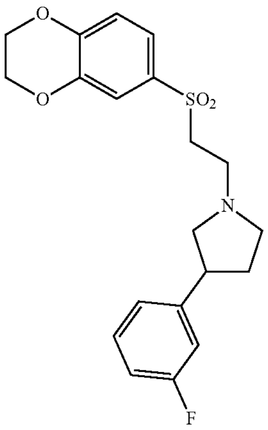 [SMILES: O=S(=O)(CCN1CCC(c2cccc(F)c2)C1)c1ccc2c(c1)OCCO2] | 137) |
| 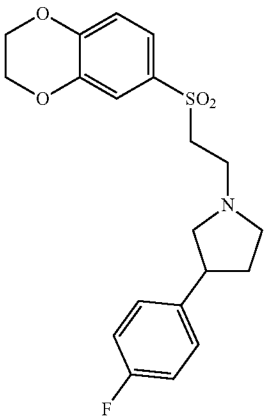 | 138) |
| 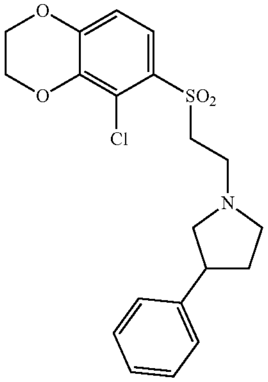 [SMILES: O=S(=O)(CCN1CCC(c2ccccc2)C1)c1ccc2c(c1Cl)OCCO2] | 139) |
| 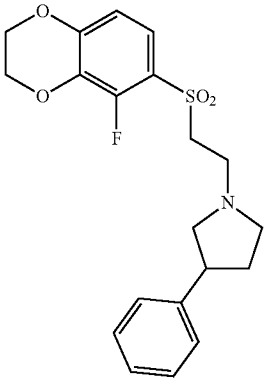 [SMILES: O=S(=O)(CCN1CCC(c2ccccc2)C1)c1ccc2c(c1F)OCCO2] | 140) |
TABLE 5-continued
| Structure | |
|---|---|
| 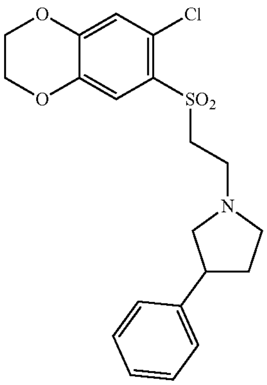 | 141) |
| 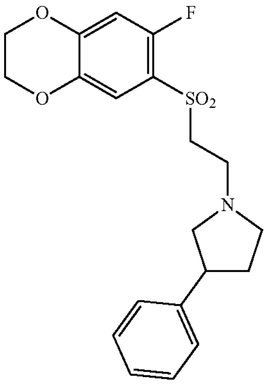 [SMILES: O=S(=O)(CCN1CCC(c2ccccc2)C1)c1cc2c(cc1F)OCCO2] | 142) |
| 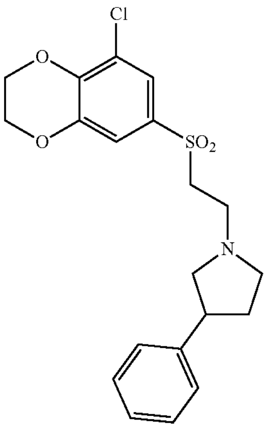 [SMILES: O=S(=O)(CCN1CCC(c2ccccc2)C1)c1cc(Cl)c2c(c1)OCCO2] | 143) |

TABLE 5-continued
| Structure | |
|---|---|
| 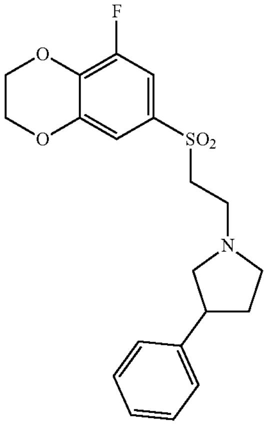 [SMILES: O=S(=O)(CCN1CCC(c2ccccc2)C1)c1cc(F)c2c(c1)OCCO2] | 144) |
TABLE 6
| Structure | |
|---|---|
| 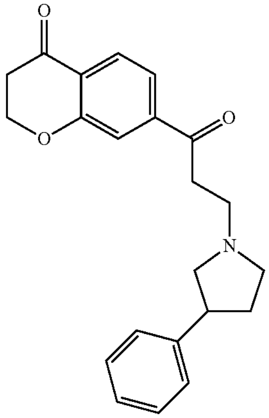 [SMILES: O=C(CCN1CCC(c2ccccc2)C1)c1ccc2c(c1)OCCC2=O] | 145) |
| 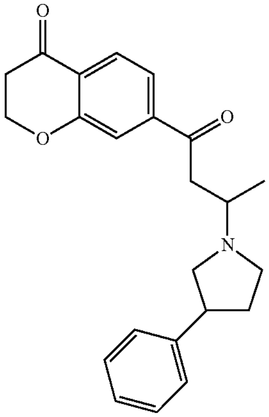 [SMILES: CC(CC(=O)c1ccc2c(c1)OCCC2=O)N1CCC(c2ccccc2)C1] | 146) |
TABLE 6-continued
| Structure | |
|---|---|
| 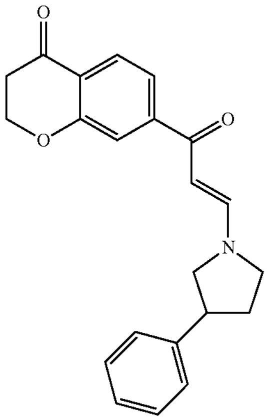 [SMILES: O=C(/C=C/N1CCC(c2ccccc2)C1)c1ccc2c(c1)OCCC2=O] | 147) |
| 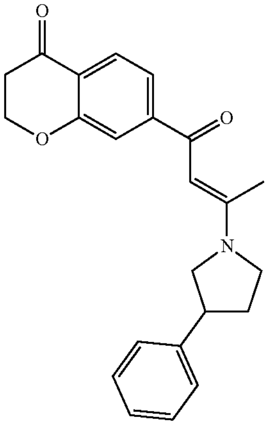 [SMILES: C/C(=C\C(=O)c1ccc2c(c1)OCCC2=O)N1CCC(c2ccccc2)C1] | 148) |
| 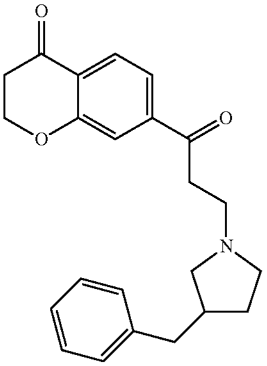 [SMILES: O=C(CCN1CCC(Cc2ccccc2)C1)c1ccc2c(c1)OCCC2=O] | 149) |
| 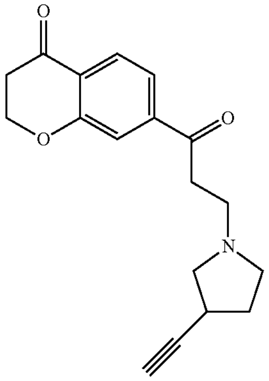 [SMILES: C#CC1CCN(CCC(=O)c2ccc3c(c2)OCCC3=O)C1] | 150) |

TABLE 6-continued
| Structure |
| --- |
| 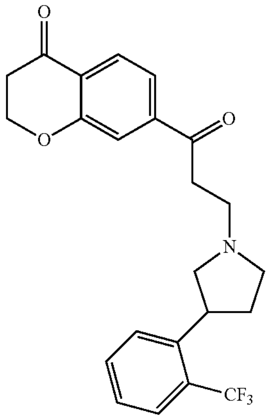 [SMILES: O=C(CCN1CCC(c2ccccc2C(F)(F)F)C1)c1ccc2c(c1)OCCC2=O] 151) |
| 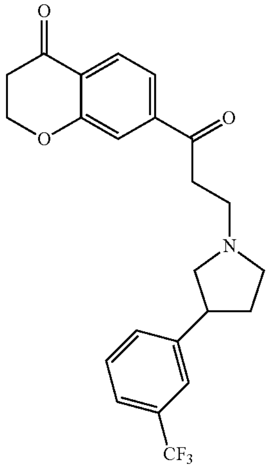 [SMILES: O=C(CCN1CCC(c2cccc(C(F)(F)F)c2)C1)c1ccc2c(c1)OCCC2=O] 152) |
| 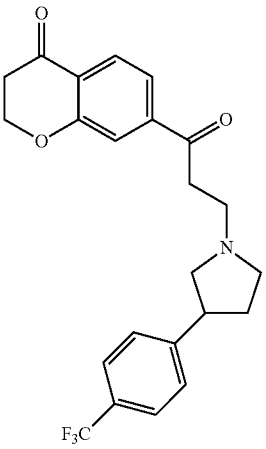 [SMILES: O=C(CCN1CCC(c2ccc(C(F)(F)F)cc2)C1)c1ccc2c(c1)OCCC2=O] 153) |
TABLE 6-continued
| Structure |
| --- |
| 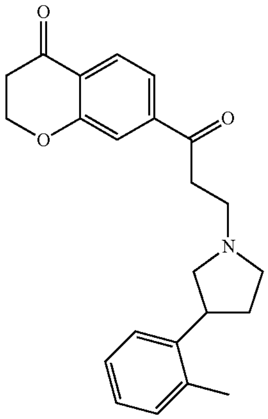 [SMILES: Cc1ccccc1C1CCN(CCC(=O)c2ccc3c(c2)OCCC3=O)C1] 154) |
| 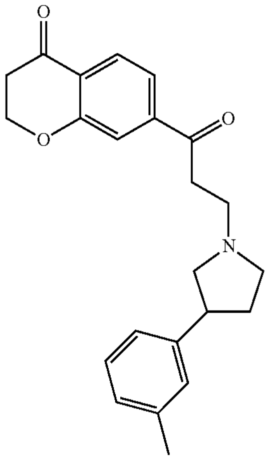 [SMILES: Cc1cccc(C2CCN(CCC(=O)c3ccc4c(c3)OCCC4=O)C2)c1] 155) |
| 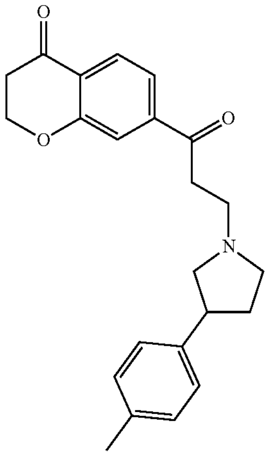 [SMILES: Cc1ccc(C2CCN(CCC(=O)c3ccc4c(c3)OCCC4=O)C2)cc1] 156) |

TABLE 6-continued
| Structure |
| --- |
| 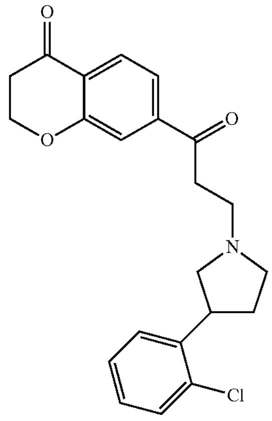 [SMILES: O=C(CCN1CCC(c2ccccc2Cl)C1)c1ccc2c(c1)OCCC2=O] 157) |
| 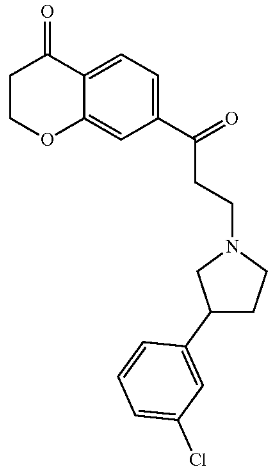 [SMILES: O=C(CCN1CCC(c2cccc(Cl)c2)C1)c1ccc2c(c1)OCCC2=O] 158) |
| 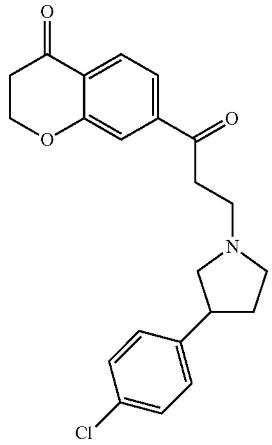 [SMILES: O=C(CCN1CCC(c2ccc(Cl)cc2)C1)c1ccc2c(c1)OCCC2=O] 159) |
TABLE 6-continued
| Structure |
| --- |
| 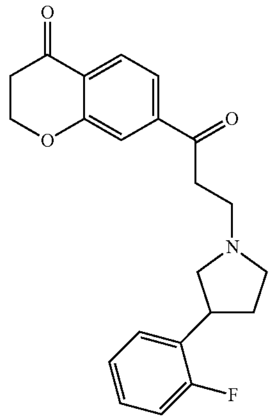 [SMILES: O=C(CCN1CCC(c2ccccc2F)C1)c1ccc2c(c1)OCCC2=O] 160) |
| 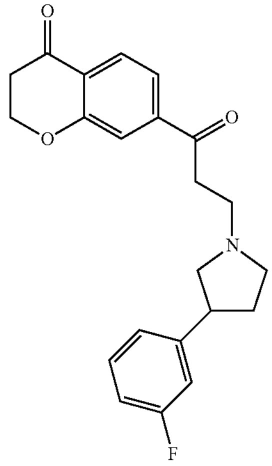 [SMILES: O=C(CCN1CCC(c2cccc(F)c2)C1)c1ccc2c(c1)OCCC2=O] 161) |
| 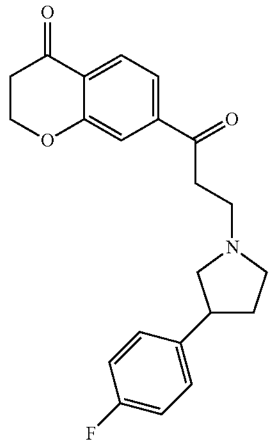 [SMILES: O=C(CCN1CCC(c2ccc(F)cc2)C1)c1ccc2c(c1)OCCC2=O] 162) |

TABLE 6-continued
| Structure | |
|---|---|
| 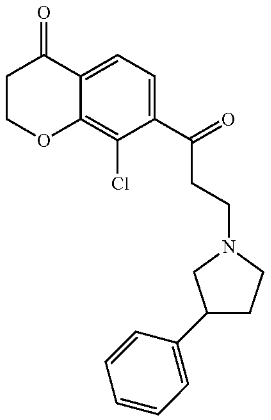 [SMILES: O=C(CCN1CCC(c2ccccc2)C1)c1ccc2c(c1Cl)OCCC2=O] | 163 |
| 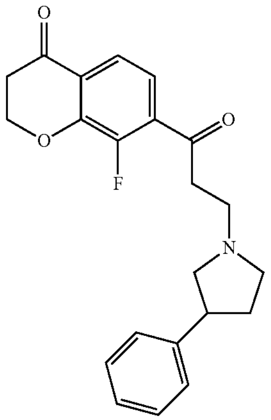 [SMILES: O=C(CCN1CCC(c2ccccc2)C1)c1ccc2c(c1F)OCCC2=O] | 164) |
| 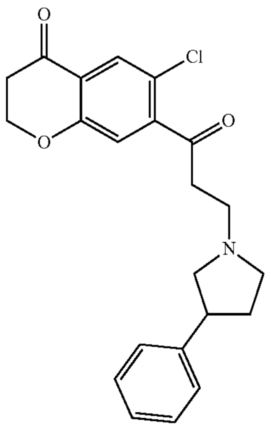 [SMILES: O=C(CCN1CCC(c2ccccc2)C1)c1cc2c(cc1Cl)C(=O)CCO2] | 165) |
TABLE 6-continued
| Structure | |
|---|---|
| 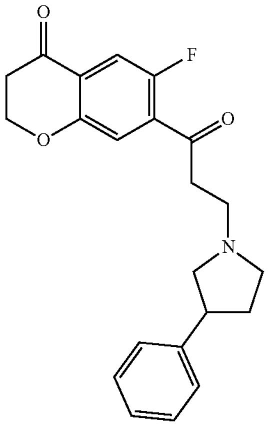 [SMILES: O=C(CCN1CCC(c2ccccc2)C1)c1cc2c(cc1F)C(=O)CCO2] | 166) |
| 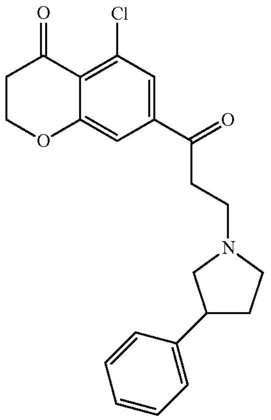 [SMILES: O=C(CCN1CCC(c2ccccc2)C1)c1cc(Cl)c2c(c1)OCCC2=O] | 167) |
| 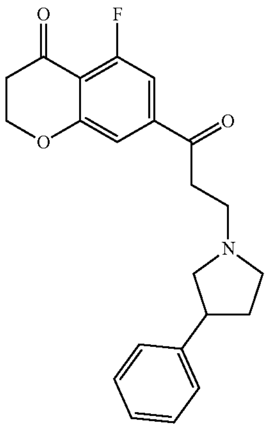 [SMILES: O=C(CCN1CCC(c2ccccc2)C1)c1cc(F)c2c(c1)OCCC2=O] | 168) |

TABLE 7
| Structure | |
|---|---|
| 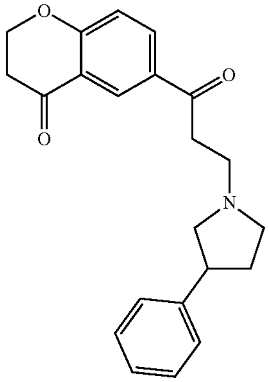 [SMILES: O=C(CCN1CCC(c2ccccc2)C1)c1ccc2c(c1)C(=O)CCO2] | 169) |
| 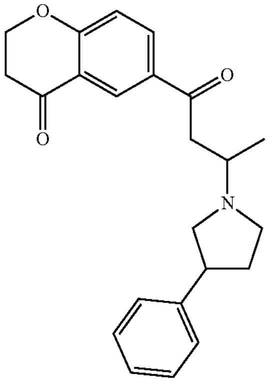 [SMILES: CC(CC(=O)c1ccc2c(c1)C(=O)CCO2)N1CCC(c2ccccc2)C1] | 170) |
| 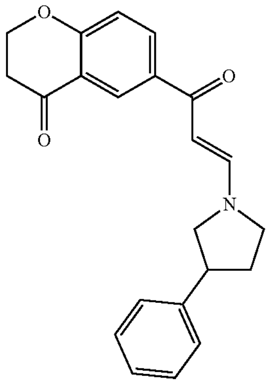 [SMILES: O=C(/C=C/N1CCC(c2ccccc2)C1)c1ccc2c(c1)C(=O)CCO2] | 171) |
| 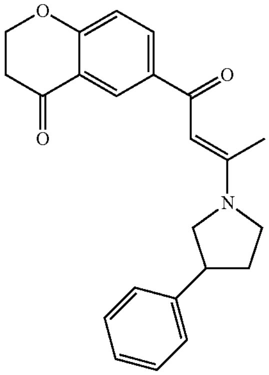 [SMILES: C/C(=C\C(=O)c1ccc2c(c1)C(=O)CCO2)N1CCC(c2ccccc2)C1] | 172) |
TABLE 7-continued
| Structure | |
|---|---|
| 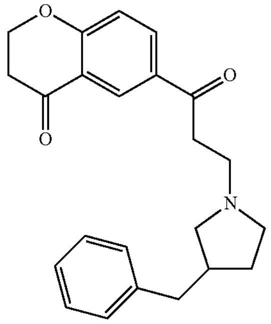 [SMILES: O=C(CCN1CCC(Cc2ccccc2)C1)c1ccc2c(c1)C(=O)CCO2] | 173) |
| 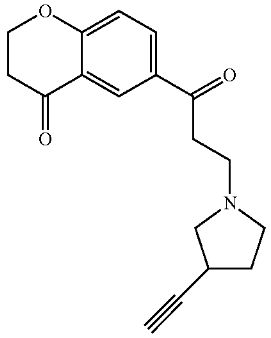 [SMILES: C#CC1CCN(CCC(=O)c2ccc3c(c2)C(=O)CCO3)C1] | 174) |
| 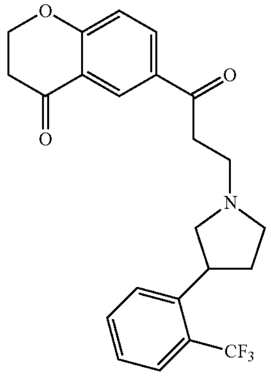 | 175) |
| 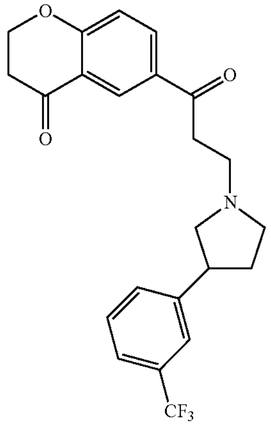 [SMILES: O=C(CCN1CCC(c2cccc(C(F)(F)F)c2)C1)c1ccc2c(c1)C(=O)CCO2] | 176) |

TABLE 7-continued
| Structure | |
|---|---|
| 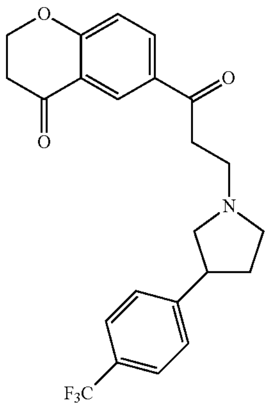 [SMILES: O=C(CCN1CCC(c2ccc(C(F)(F)F)cc2)C1)c1ccc2c(c1)C(=O)CCO2] | 177) |
| 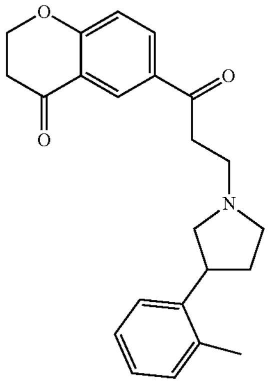 [SMILES: Cc1ccccc1C1CCN(CCC(=O)c2ccc3c(c2)C(=O)CCO3)C1] | 178) |
| 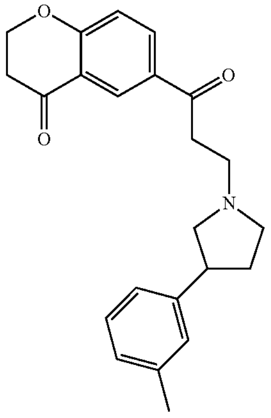 [SMILES: Cc1cccc(C2CCN(CCC(=O)c3ccc4c(c3)C(=O)CCO4)C2)c1] | 179) |
| 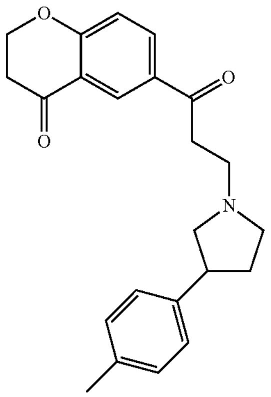 [SMILES: Cc1ccc(C2CCN(CCC(=O)c3ccc4c(c3)C(=O)CCO4)C2)cc1] | 180) |
TABLE 7-continued
| Structure | |
|---|---|
| 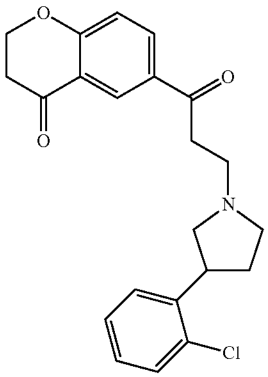 [SMILES: O=C(CCN1CCC(c2ccccc2Cl)C1)c1ccc2c(c1)C(=O)CCO2] | 181) |
| 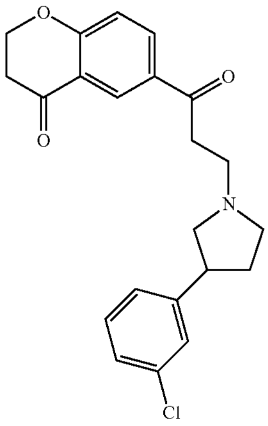 [SMILES: O=C(CCN1CCC(c2cccc(Cl)c2)C1)c1ccc2c(c1)C(=O)CCO2] | 182) |
| 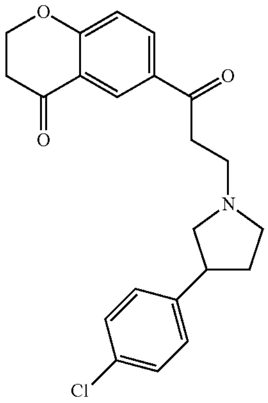 [SMILES: O=C(CCN1CCC(c2ccc(Cl)cc2)C1)c1ccc2c(c1)C(=O)CCO2] | 183) |
| 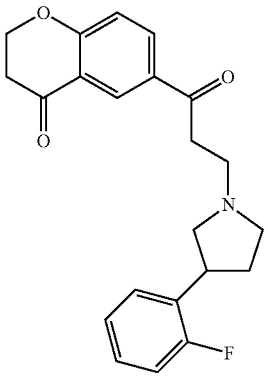 [SMILES: O=C(CCN1CCC(c2ccccc2F)C1)c1ccc2c(c1)C(=O)CCO2] | 184) |

TABLE 7-continued
| Structure | |
|---|---|
| 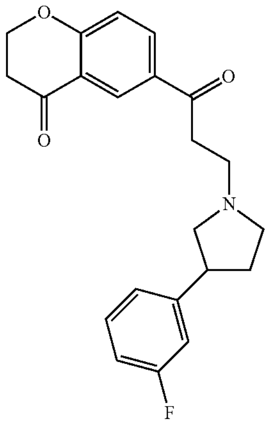 [SMILES: O=C(CCN1CCC(c2cccc(F)c2)C1)c1ccc2c(c1)C(=O)CCO2] | 185) |
| 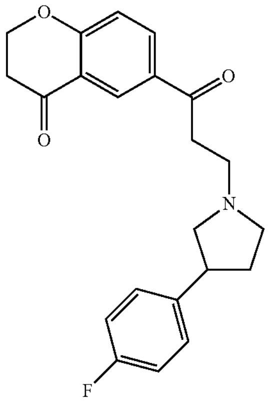 [SMILES: O=C(CCN1CCC(c2ccc(F)cc2)C1)c1ccc2c(c1)C(=O)CCO2] | 186) |
| 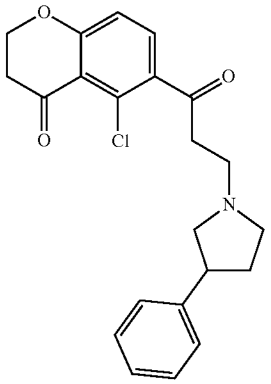 [SMILES: O=C(CCN1CCC(c2ccccc2)C1)c1ccc2c(c1F)C(=O)CCO2] | 187) |
| 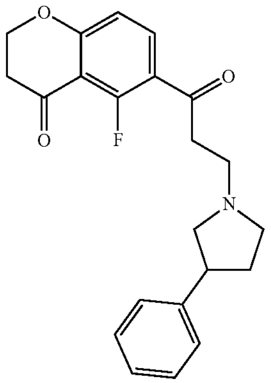 | 188) |
TABLE 7-continued
| Structure | |
|---|---|
| 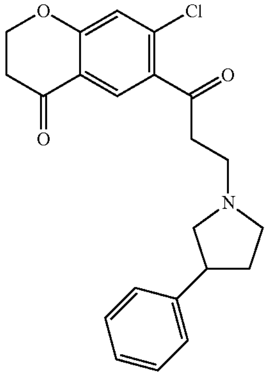 [SMILES: O=C(CCN1CCC(c2ccccc2)C1)c1cc2c(cc1Cl)OCCC2=O] | 189) |
| 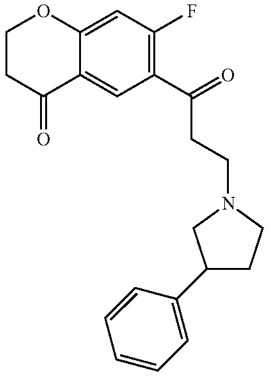 [SMILES: O=C(CCN1CCC(c2ccccc2)C1)c1cc2c(cc1F)OCCC2=O] | 190) |
| 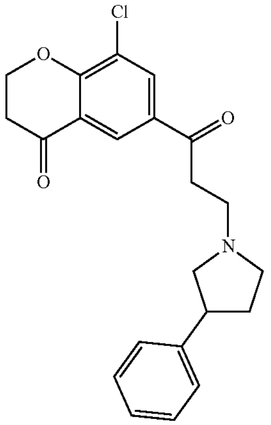 [SMILES: O=C(CCN1CCC(c2ccccc2)C1)c1cc(Cl)c2c(c1)C(=O)CCO2] | 191) |

TABLE 7-continued
| Structure | |
|---|---|
| 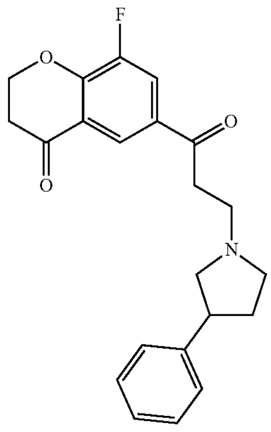 [SMILES: O=C(CCN1CCC(c2ccccc2)C1)c1cc(F)c2c(c1)C(=O)CCO2] | 192) |
TABLE 8
| Structure | |
|---|---|
| 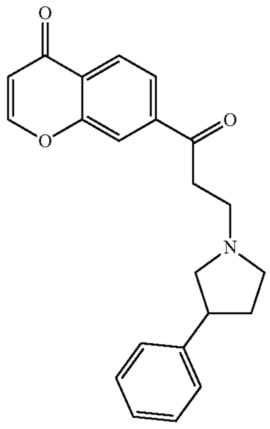 [SMILES: O=C(CCN1CCC(c2ccccc2)C1)c1ccc2c(=O)ccoc2c1] | 193) |
| 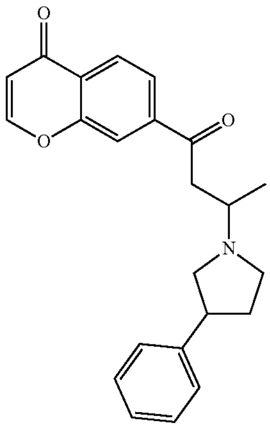 [SMILES: CC(CC(=O)c1ccc2c(=O)ccoc2c1)N1CCC(c2ccccc2)C1] | 194) |
TABLE 8-continued
| Structure | |
|---|---|
| 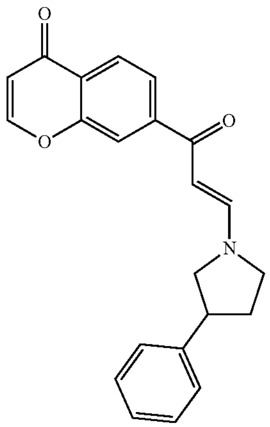 [SMILES: O=C(/C=C/N1CCC(c2ccccc2)C1)c1ccc2c(=O)ccoc2c1] | 195) |
| 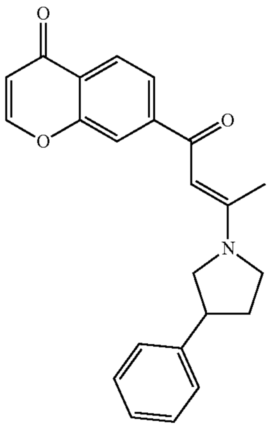 [SMILES: C/C(=C\C(=O)c1ccc2c(=O)ccoc2c1)N1CCC(c2ccccc2)C1] | 196) |
| 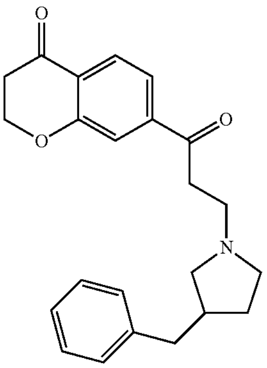 [SMILES: O=C(CCN1CCC(Cc2ccccc2)C1)c1ccc2c(c1)OCCC2=O] | 197) |
| 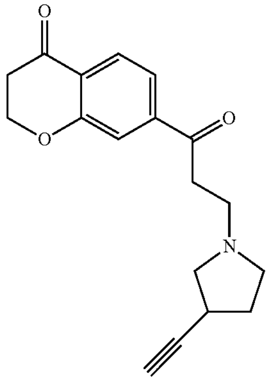 [SMILES: C#CC1CCN(CCC(=O)c2ccc3c(c2)OCCC3=O)C1] | 198) |

TABLE 8-continued
| Structure |
| --- |
| 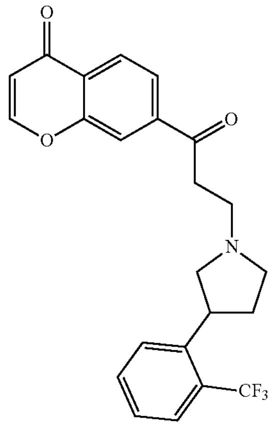 [SMILES: O=C(CCN1CCC(c2ccccc2C(F)(F)F)C1)c1ccc2c(=O)ccoc2c1] 199) |
| 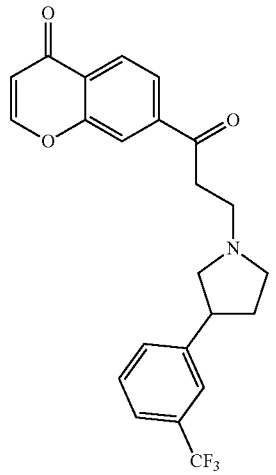 [SMILES: O=C(CCN1CCC(c2cccc(C(F)(F)F)c2)C1)c1ccc2c(=O)ccoc2c1] 200) |
| 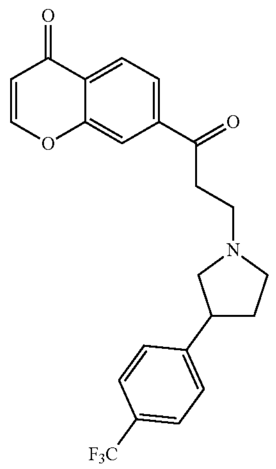 [SMILES: O=C(CCN1CCC(c2ccc(C(F)(F)F)cc2)C1)c1ccc2c(=O)ccoc2c1] 201) |
TABLE 8-continued
| Structure |
| --- |
| 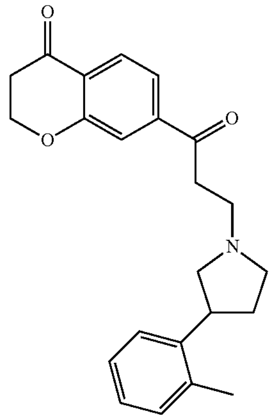 [SMILES: Cc1ccccc1C1CCN(CCC(=O)c2ccc3c(c2)OCCC3=O)C1] 202) |
| 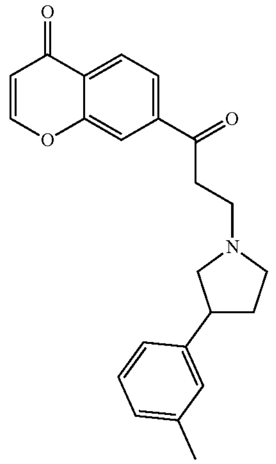 [SMILES: Cc1cccc(C2CCN(CCC(=O)c3ccc4c(=O)ccoc4c3)C2)c1] 203) |
| 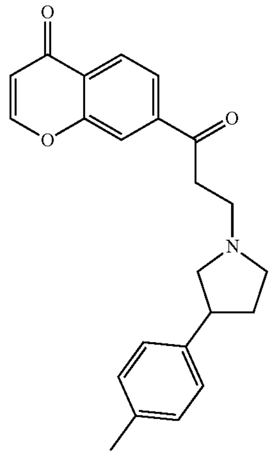 [SMILES: Cc1ccc(C2CCN(CCC(=O)c3ccc4c(=O)ccoc4c3)C2)cc1] 204) |

TABLE 8-continued
| Structure | |
|---|---|
| 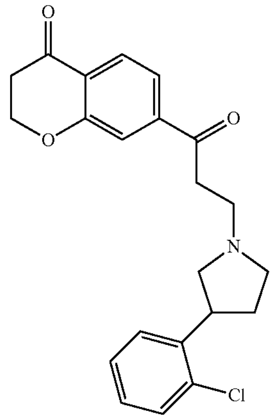 [SMILES: O=C(CCN1CCC(c2ccccc2Cl)C1)c1ccc2c(c1)OCCC2=O] | 205) |
| 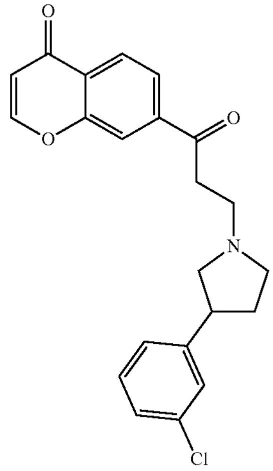 [SMILES: O=C(CCN1CCC(c2cccc(Cl)c2)C1)c1ccc2c(=O)ccoc2c1] | 206) |
| 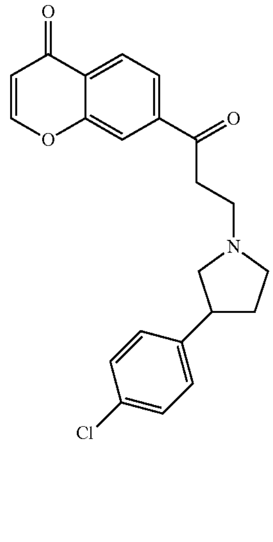 [SMILES: O=C(CCN1CCC(c2ccc(Cl)cc2)C1)c1ccc2c(=O)ccoc2c1] | 207) |
TABLE 8-continued
| Structure | |
|---|---|
| 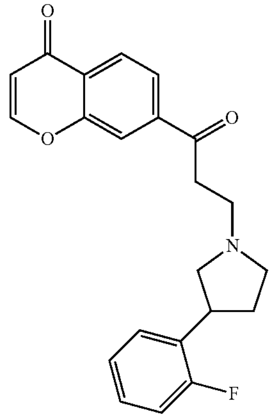 [SMILES: O=C(CCN1CCC(c2ccccc2F)C1)c1ccc2c(=O)ccoc2c1] | 208) |
| 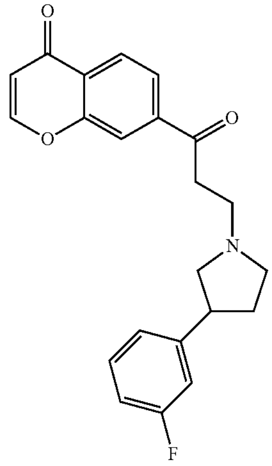 [SMILES: O=C(CCN1CCC(c2cccc(F)c2)C1)c1ccc2c(=O)ccoc2c1] | 209) |
| 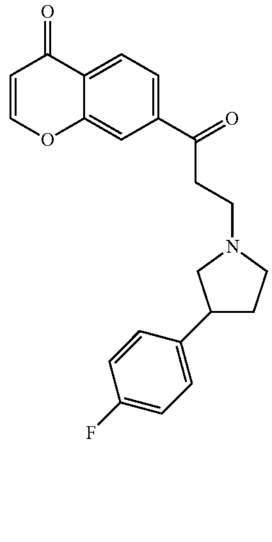 [SMILES: O=C(CCN1CCC(c2ccc(F)cc2)C1)c1ccc2c(=O)ccoc2c1] | 210) |

TABLE 8-continued
| Structure | |
|---|---|
| 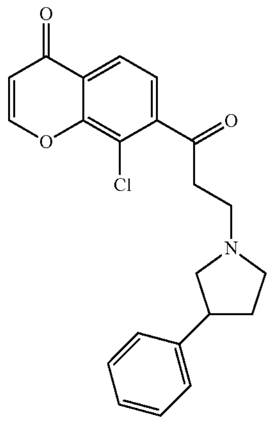 [SMILES: O=C(CCN1CCC(c2ccccc2)C1)c1ccc2c(=O)ccoc2c1Cl] | 211) |
| 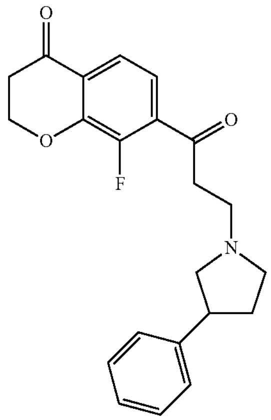 | 212) |
| 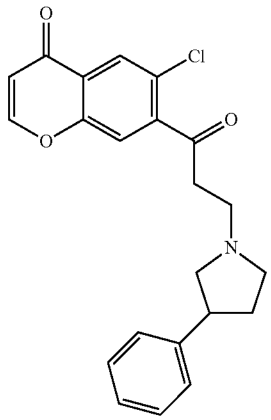 [SMILES: O=C(CCN1CCC(c2ccccc2)C1)c1cc2occc(=O)c2cc1Cl] | 213) |
TABLE 8-continued
| Structure | |
|---|---|
| 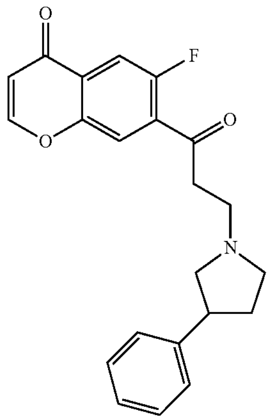 [SMILES: O=C(CCN1CCC(c2ccccc2)C1)c1cc2occc(=O)c2cc1F] | 214) |
| 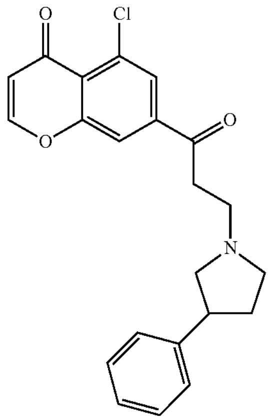 [SMILES: O=C(CCN1CCC(c2ccccc2)C1)c1cc(Cl)c2c(=O)ccoc2c1] | 215) |
| 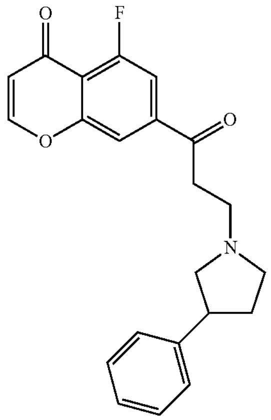 [SMILES: O=C(CCN1CCC(c2ccccc2)C1)c1cc(F)c2c(=O)ccoc2c1] | 216) |

TABLE 9
| Structure |
|---|
| 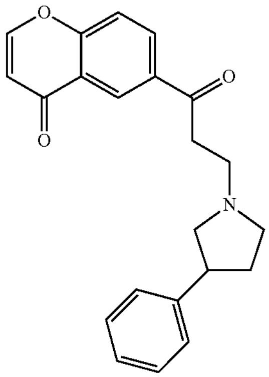 [SMILES: O=C(CCN1CCC(c2ccccc2)C1)c1ccc2occc(=O)c2c1] 217) |
| 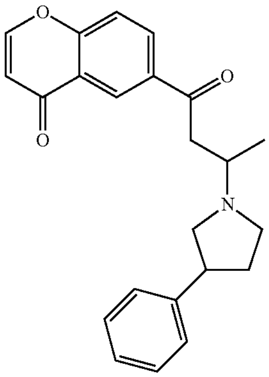 [SMILES: CC(CC(=O)c1ccc2occc(=O)c2c1)N1CCC(c2ccccc2)C1] 218) |
| 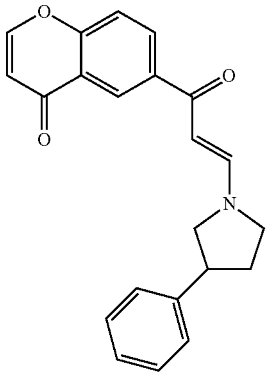 [SMILES: O=C(/C=C/N1CCC(c2ccccc2)C1)c1ccc2occc(=O)c2c1] 219) |
| 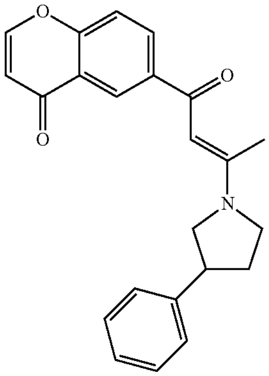 [SMILES: C/C(=C\C(=O)c1ccc2occc(=O)c2c1)N1CCC(c2ccccc2)C1] 220) |
TABLE 9-continued
| Structure |
|---|
| 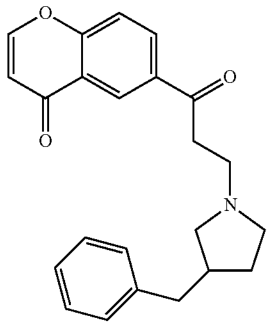 [SMILES: O=C(CCN1CCC(Cc2ccccc2)C1)c1ccc2occc(=O)c2c1] 221) |
| 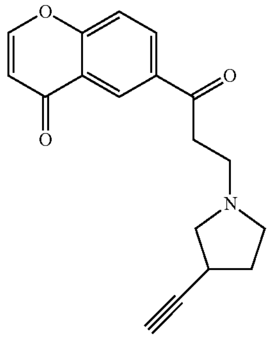 [SMILES: C#CC1CCN(CCC(=O)c2ccc3occc(=O)c3c2)C1] 222) |
| 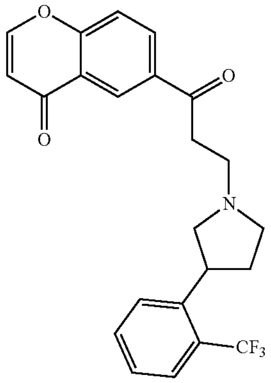 [SMILES: O=C(CCN1CCC(c2ccccc2C(F)(F)F)C1)c1ccc2occc(=O)c2c1] 223) |
| 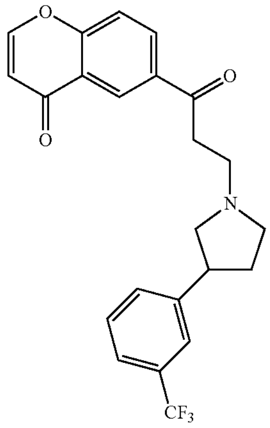 [SMILES: O=C(CCN1CCC(c2cccc(C(F)(F)F)c2)C1)c1ccc2occc(=O)c2c1] 224) |

TABLE 9-continued
| Structure | |
|---|---|
| 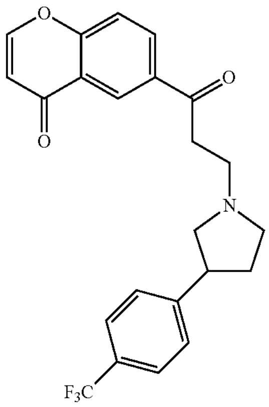 [SMILES: O=C(CCN1CCC(c2ccc(C(F)(F)F)cc2)C1)c1ccc2occc(=O)c2c1] | 225) |
| 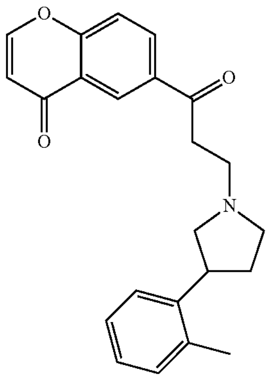 [SMILES: Cc1ccccc1C1CCN(CCC(=O)c2ccc3occc(=O)c3c2)C1] | 226) |
| 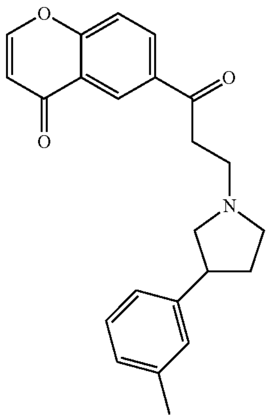 [SMILES: Cc1cccc(C2CCN(CCC(=O)c3ccc4occc(=O)c4c3)C2)c1] | 227) |
| 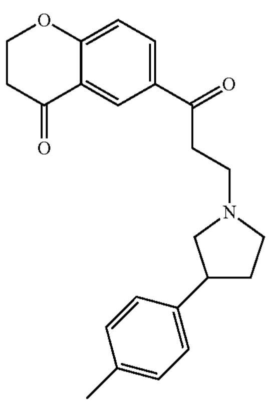 [SMILES: Cc1ccc(C2CCN(CCC(=O)c3ccc4c(c3)C(=O)CCO4)C2)cc1] | 228) |
TABLE 9-continued
| Structure | |
|---|---|
| 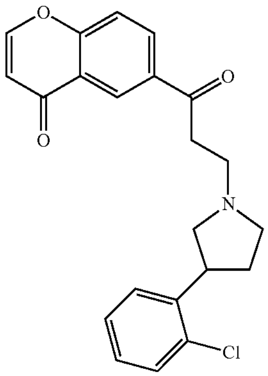 [SMILES: O=C(CCN1CCC(c2ccccc2Cl)C1)c1ccc2occc(=O)c2c1] | 229) |
| 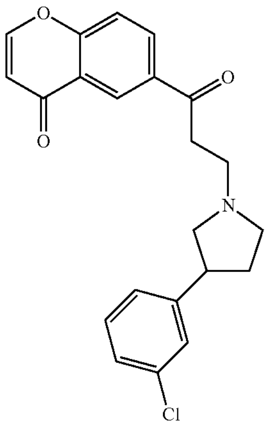 [SMILES: O=C(CCN1CCC(c2cccc(Cl)c2)C1)c1ccc2occc(=O)c2c1] | 230) |
| 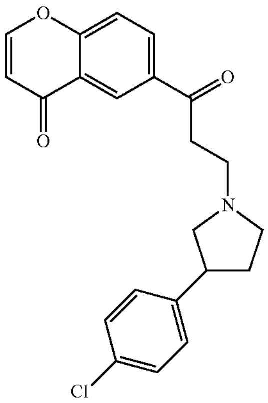 [SMILES: O=C(CCN1CCC(c2ccc(Cl)cc2)C1)c1ccc2occc(=O)c2c1] | 231) |
| 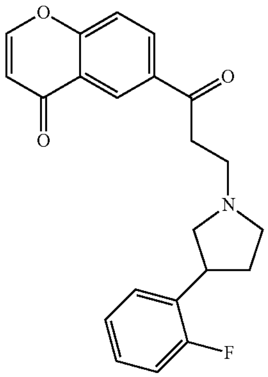 [SMILES: O=C(CCN1CCC(c2ccccc2F)C1)c1ccc2occc(=O)c2c1] | 232) |

TABLE 9-continued
Structure
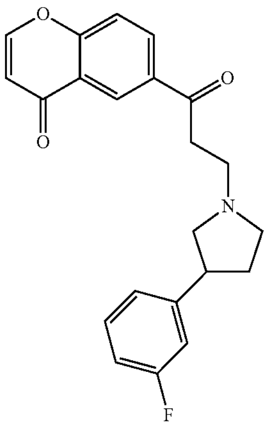 [SMILES: O=C(CCN1CCC(c2cccc(F)c2)C1)c1ccc2occc(=O)c2c1]
233)
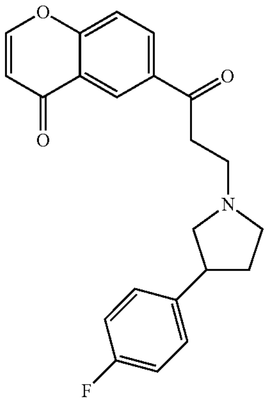 [SMILES: O=C(CCN1CCC(c2ccc(F)cc2)C1)c1ccc2occc(=O)c2c1]
234)
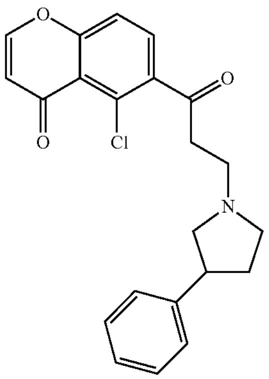
235)
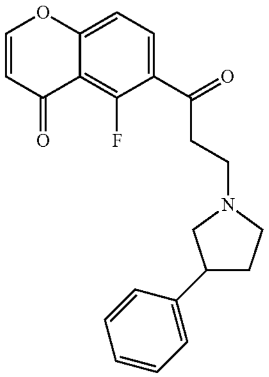 [SMILES: O=C(CCN1CCC(c2ccccc2)C1)c1ccc2occc(=O)c2c1F]
236)
TABLE 9-continued
Structure
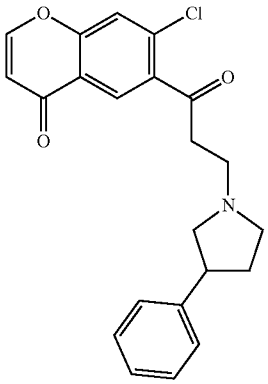 [SMILES: O=C(CCN1CCC(c2ccccc2)C1)c1cc2c(=O)ccoc2cc1Cl]
237)
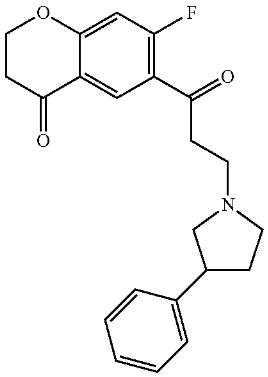 [SMILES: O=C(CCN1CCC(c2ccccc2)C1)c1cc2c(cc1F)OCCC2=O]
238)
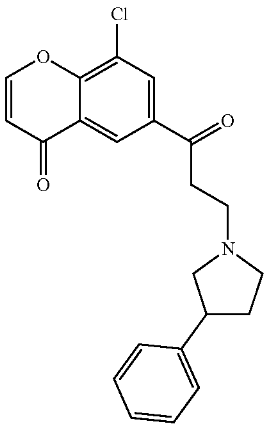 [SMILES: O=C(CCN1CCC(c2ccccc2)C1)c1cc(Cl)c2occc(=O)c2c1]
239)

TABLE 9-continued
| Structure | |
|---|---|
| 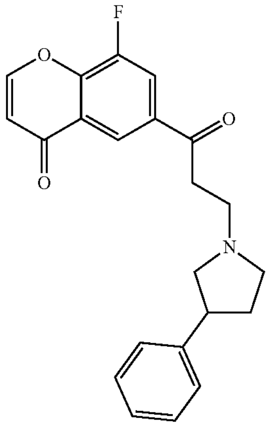 | 240) |
TABLE 10
| Structure | |
|---|---|
| 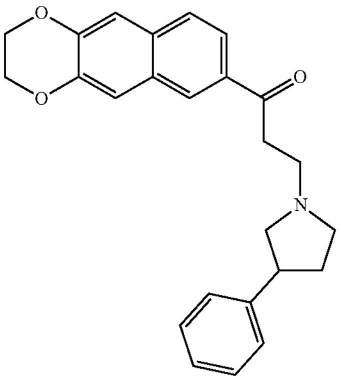 | 241) |
| 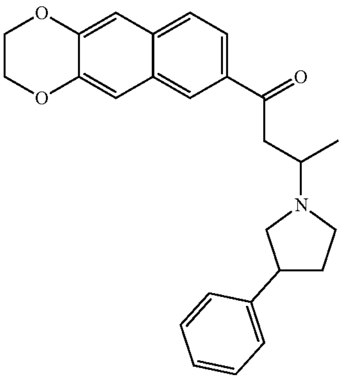 | 242) |
TABLE 10-continued
| Structure | |
|---|---|
| 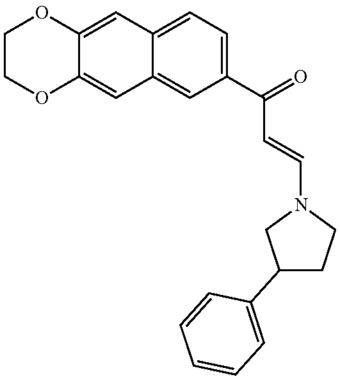 [SMILES: O=C(/C=C/N1CCC(c2ccccc2)C1)c1ccc2cc3c(cc2c1)OCCO3] | 243) |
| 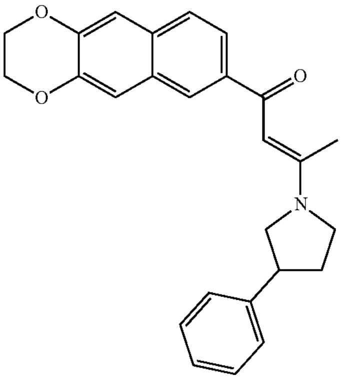 | 244) |
| 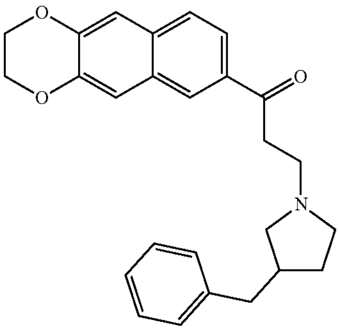 [SMILES: O=C(CCN1CCC(Cc2ccccc2)C1)c1ccc2cc3c(cc2c1)OCCO3] | 245) |
| 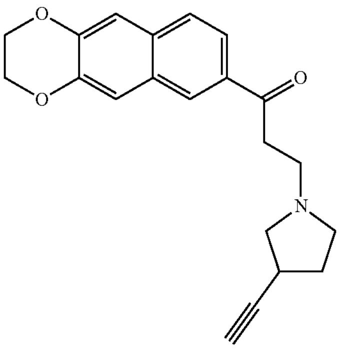 [SMILES: C#CC1CCN(CCC(=O)c2ccc3cc4c(cc3c2)OCCO4)C1] | 246) |

TABLE 10-continued
| Structure | |
|---|---|
| 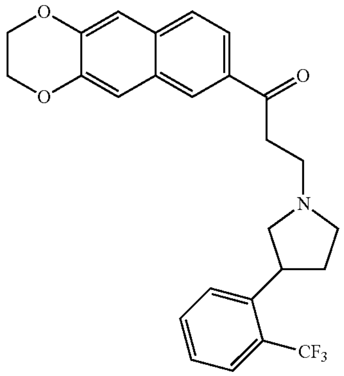 | 247) |
| 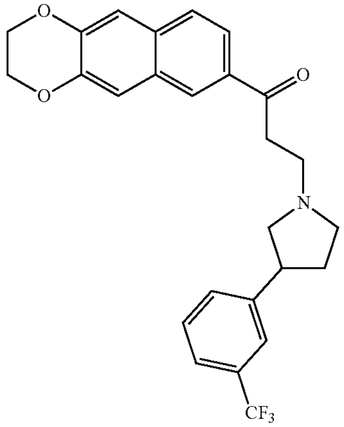 [SMILES: O=C(CCN1CCC(c2cccc(C(F)(F)F)c2)C1)c1ccc2cc3c(cc2c1)OCCO3] | 248) |
| 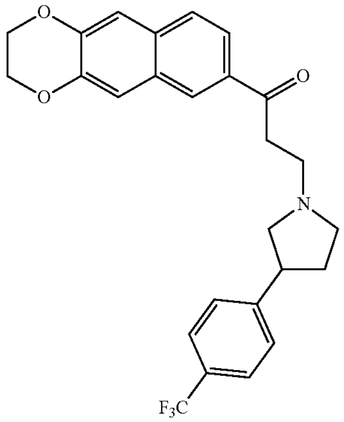 [SMILES: O=C(CCN1CCC(c2ccc(C(F)(F)F)cc2)C1)c1ccc2cc3c(cc2c1)OCCO3] | 249) |
| 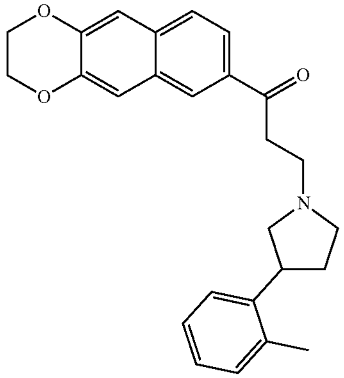 [SMILES: Cc1ccccc1C1CCN(CCC(=O)c2ccc3cc4c(cc3c2)OCCO4)C1] | 250) |
TABLE 10-continued
| Structure | |
|---|---|
| 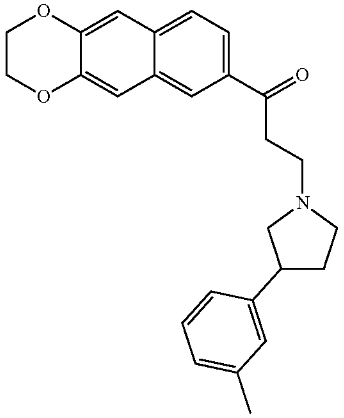 [SMILES: Cc1cccc(C2CCN(CCC(=O)c3ccc4cc5c(cc4c3)OCCO5)C2)c1] | 251) |
| 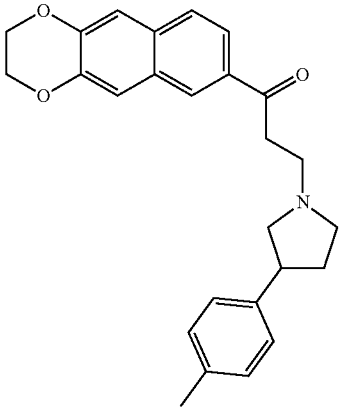 [SMILES: Cc1ccc(C2CCN(CCC(=O)c3ccc4cc5c(cc4c3)OCCO5)C2)cc1] | 252) |
| 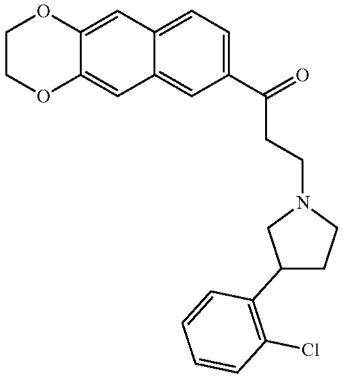 | 253) |

TABLE 10-continued
| Structure |
|---|
| 254) 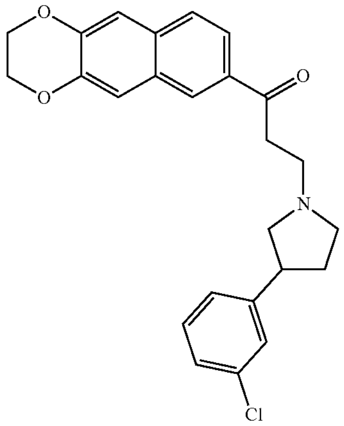 [SMILES: O=C(CCN1CCC(c2cccc(Cl)c2)C1)c1ccc2cc3c(cc2c1)OCCO3] |
| 255) 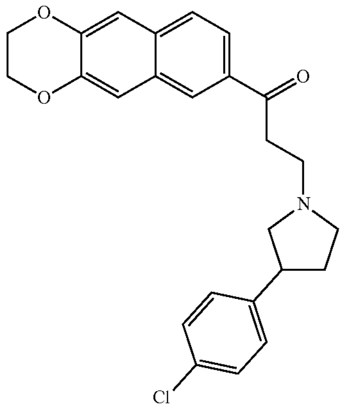 |
| 256) 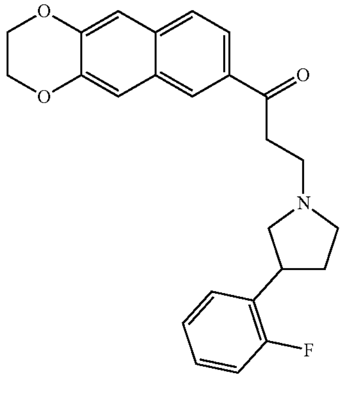 [SMILES: O=C(CCN1CCC(c2ccccc2F)C1)c1ccc2cc3c(cc2c1)OCCO3] |
TABLE 10-continued
| Structure |
|---|
| 257) 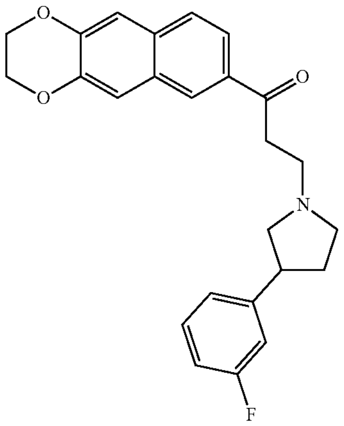 |
| 258) 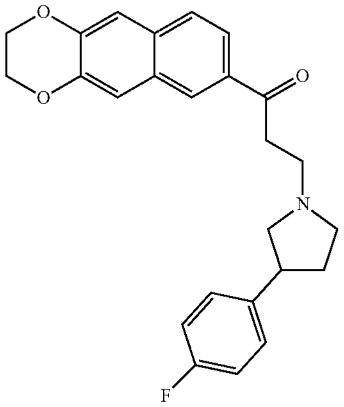 |
| 259) 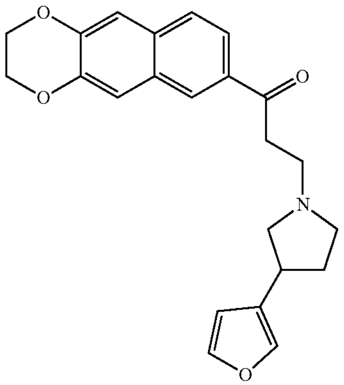 |
| 260) 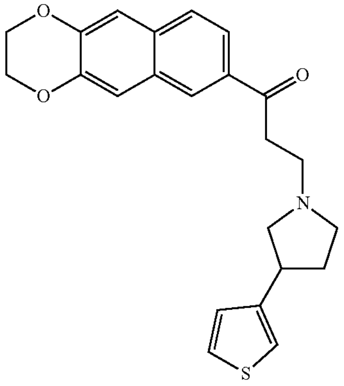 |

TABLE 10-continued
| Structure |
| --- |
| 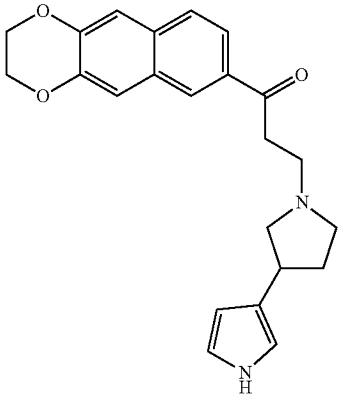 261) |
| 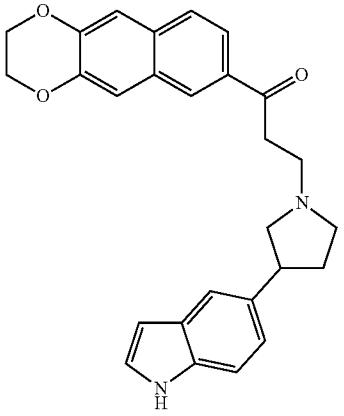 262) |
| 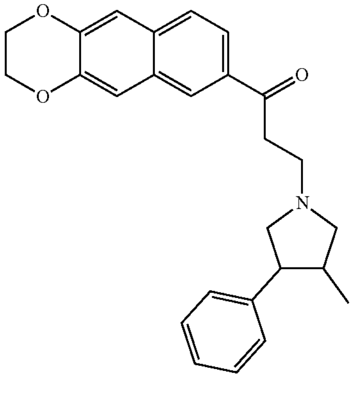 263) |
| 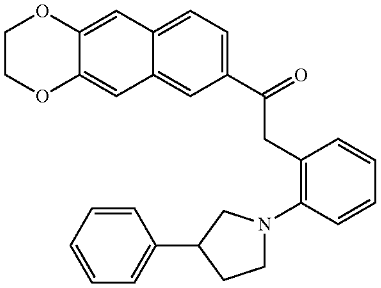 [SMILES: O=C(Cc1ccccc1N1CCC(c2ccccc2)C1)c1ccc2cc3c(cc2c1)OCCO3] 264) |
TABLE 11
| Structure |
| --- |
| 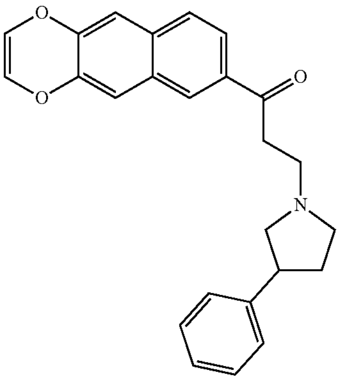 [SMILES: O=C(CCN1CCC(c2ccccc2)C1)c1ccc2cc3c(cc2c1)OC=CO3] 265) |
| 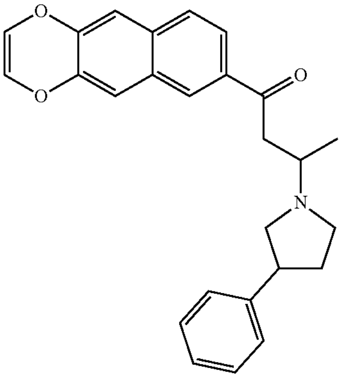 [SMILES: CC(CC(=O)c1ccc2cc3c(cc2c1)OC=CO3)N1CCC(c2ccccc2)C1] 266) |
| 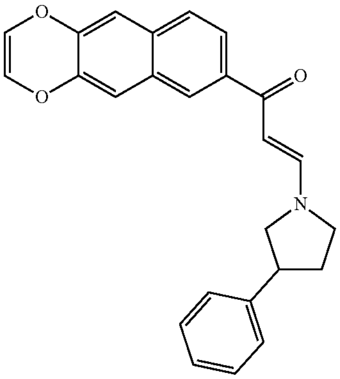 [SMILES: O=C(/C=C/N1CCC(c2ccccc2)C1)c1ccc2cc3c(cc2c1)OC=CO3] 267) |
| 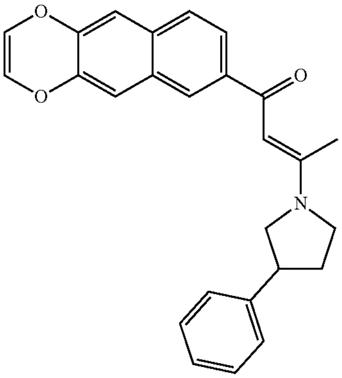 268) |

TABLE 11-continued
| Structure |
| --- |
| 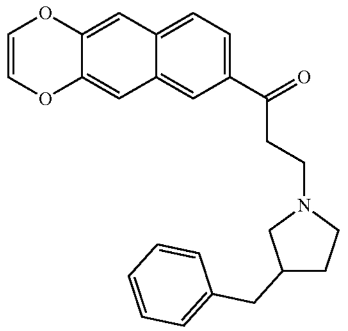 [SMILES: O=C(CCN1CCC(Cc2ccccc2)C1)c1ccc2cc3c(cc2c1)OC=CO3] 269) |
| 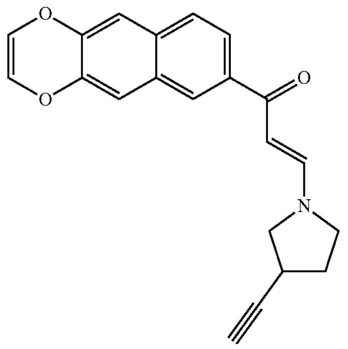 [SMILES: C#CC1CCN(/C=C/C(=O)c2ccc3cc4c(cc3c2)OC=CO4)C1] 270) |
| 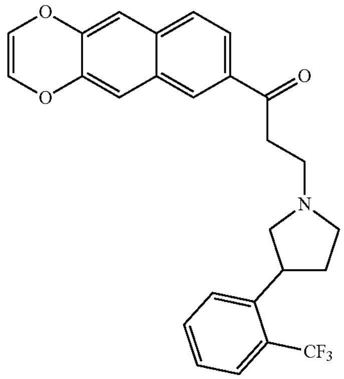 [SMILES: O=C(CCN1CCC(c2ccccc2C(F)(F)F)C1)c1ccc2cc3c(cc2c1)OC=CO3] 271) |
| 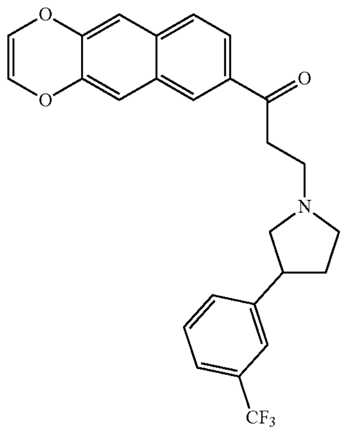 [SMILES: O=C(CCN1CCC(c2cccc(C(F)(F)F)c2)C1)c1ccc2cc3c(cc2c1)OC=CO3] 272) |
TABLE 11-continued
| Structure |
| --- |
| 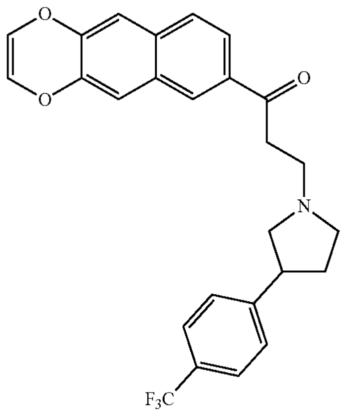 [SMILES: O=C(CCN1CCC(c2ccc(C(F)(F)F)cc2)C1)c1ccc2cc3c(cc2c1)OC=CO3] 273) |
| 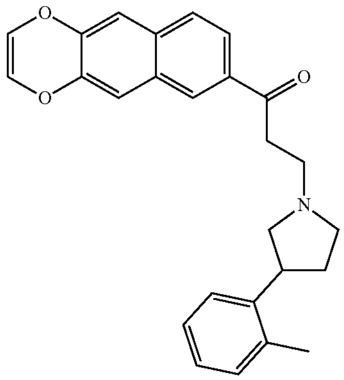 [SMILES: Cc1ccccc1C1CCN(CCC(=O)c2ccc3cc4c(cc3c2)OC=CO4)C1] 274) |
| 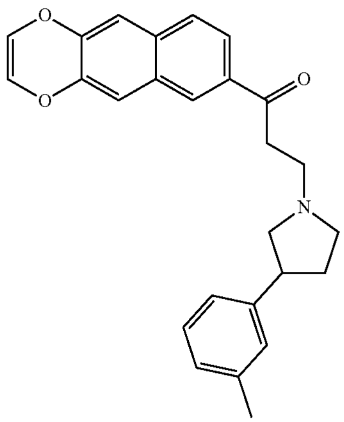 [SMILES: Cc1cccc(C2CCN(CCC(=O)c3ccc4cc5c(cc4c3)OC=CO5)C2)c1] 275) |

TABLE 11-continued
| Structure |
|---|
| 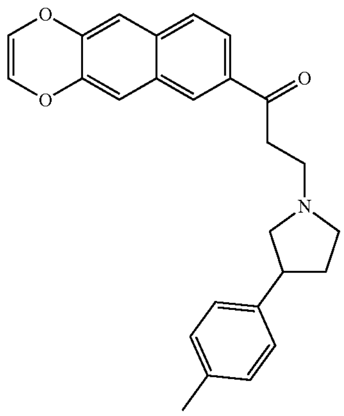 [SMILES: Cc1ccc(C2CCN(CCC(=O)c3ccc4cc5c(cc4c3)OC=CO5)C2)cc1] 276) |
| 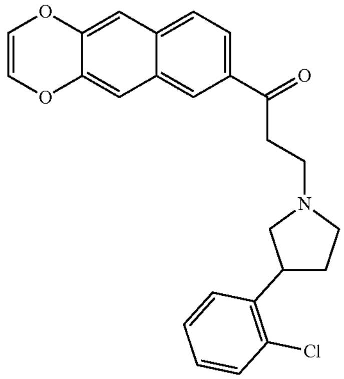 [SMILES: O=C(CCN1CCC(c2ccccc2Cl)C1)c1ccc2cc3c(cc2c1)OC=CO3] 277) |
| 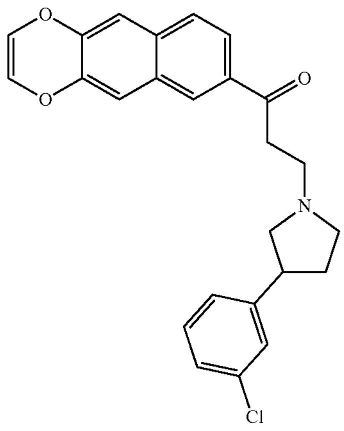 [SMILES: O=C(CCN1CCC(c2cccc(Cl)c2)C1)c1ccc2cc3c(cc2c1)OC=CO3] 278) |
TABLE 11-continued
| Structure |
|---|
| 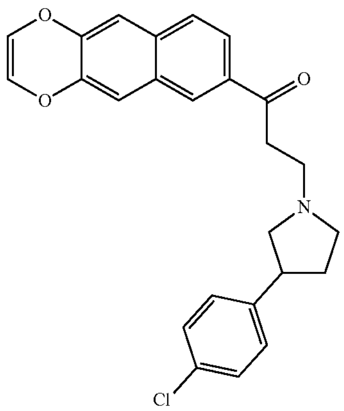 279) |
| 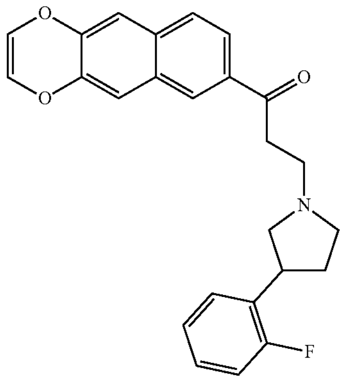 [SMILES: O=C(CCN1CCC(c2ccccc2F)C1)c1ccc2cc3c(cc2c1)OC=CO3] 280) |
| 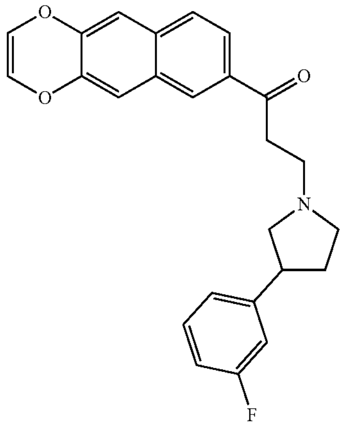 [SMILES: O=C(CCN1CCC(c2cccc(F)c2)C1)c1ccc2cc3c(cc2c1)OC=CO3] 281) |

TABLE 11-continued
| Structure | |
|---|---|
| 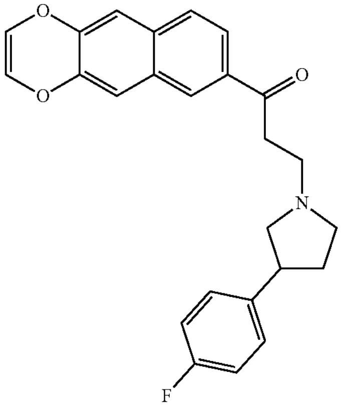 [SMILES: O=C(CCN1CCC(c2ccc(F)cc2)C1)c1ccc2cc3c(cc2c1)OC=CO3] | 282) |
| 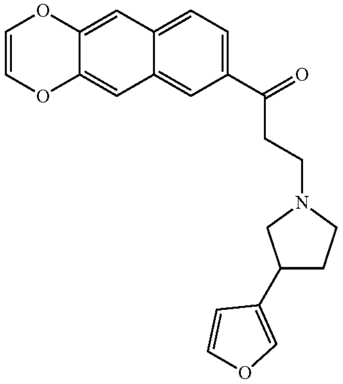 [SMILES: O=C(CCN1CCC(c2ccoc2)C1)c1ccc2cc3c(cc2c1)OC=CO3] | 283) |
| 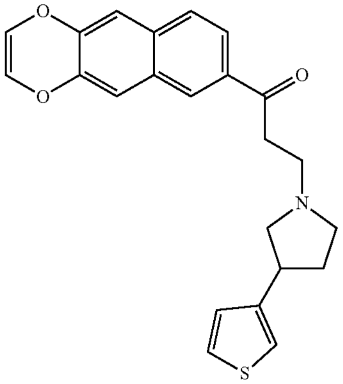 [SMILES: O=C(CCN1CCC(c2ccsc2)C1)c1ccc2cc3c(cc2c1)OC=CO3] | 284) |
| 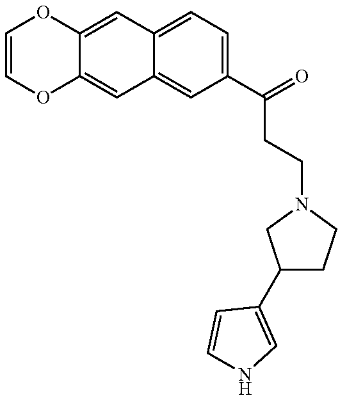 [SMILES: O=C(CCN1CCC(c2cc[nH]c2)C1)c1ccc2cc3c(cc2c1)OC=CO3] | 285) |
| 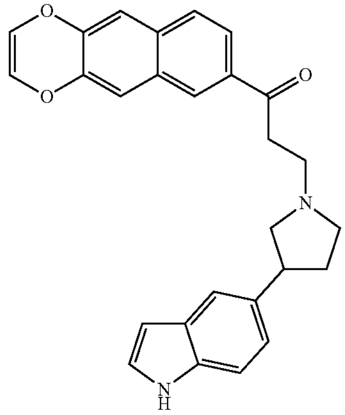 [SMILES: O=C(CCN1CCC(c2ccc3[nH]ccc3c2)C1)c1ccc2cc3c(cc2c1)OC=CO3] | 286) |
| 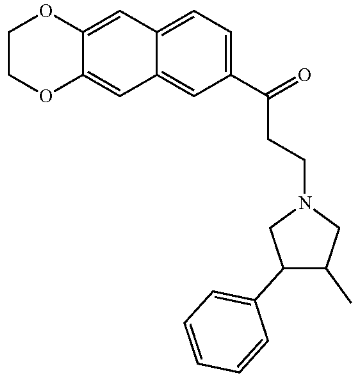 | 287) |
| 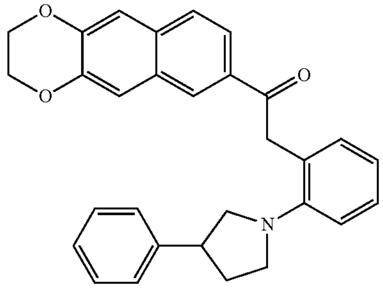 [SMILES: O=C(Cc1ccccc1N1CCC(c2ccccc2)C1)c1ccc2cc3c(cc2c1)OCCO3] | 288) |
TABLE 12
| Structure | |
|---|---|
| 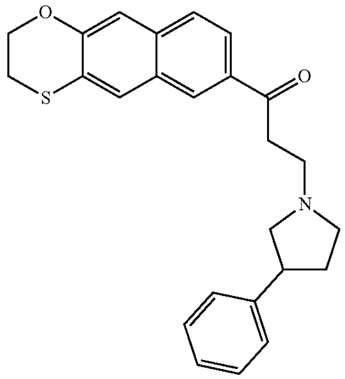 | 289) |

TABLE 12-continued
| Structure |
|---|
| 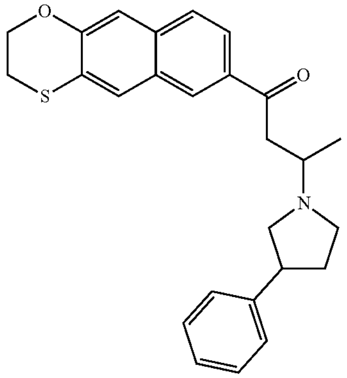 [SMILES: CC(CC(=O)c1ccc2cc3c(cc2c1)SCCO3)N1CCC(c2ccccc2)C1] 290) |
| 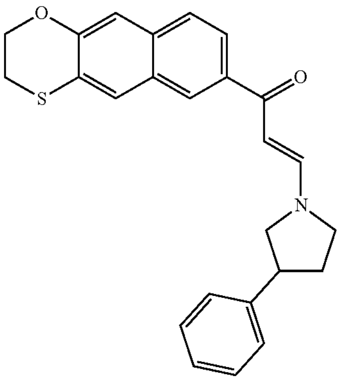 [SMILES: O=C(/C=C/N1CCC(c2ccccc2)C1)c1ccc2cc3c(cc2c1)SCCO3] 291) |
| 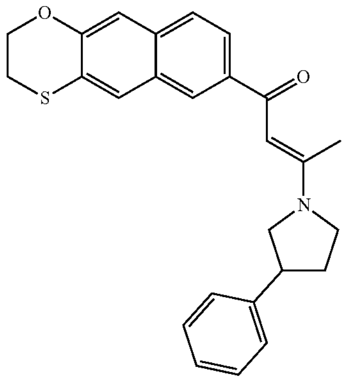 [SMILES: C/C(=C\C(=O)c1ccc2cc3c(cc2c1)SCCO3)N1CCC(c2ccccc2)C1] 292) |
| 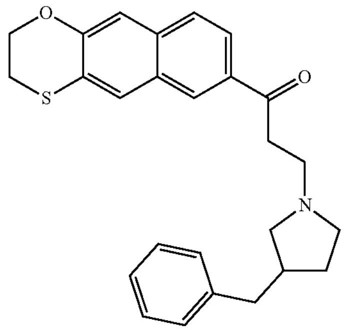 [SMILES: O=C(CCN1CCC(Cc2ccccc2)C1)c1ccc2cc3c(cc2c1)SCCO3] 293) |
TABLE 12-continued
| Structure |
|---|
| 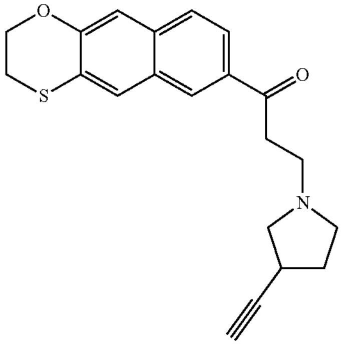 294) |
| 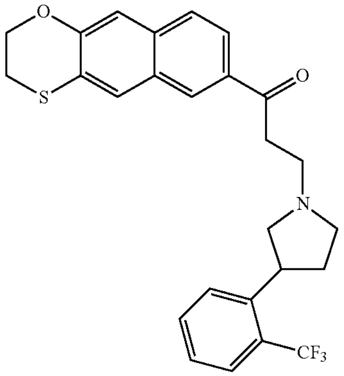 [SMILES: O=C(CCN1CCC(c2ccccc2C(F)(F)F)C1)c1ccc2cc3c(cc2c1)SCCO3] 295) |
| 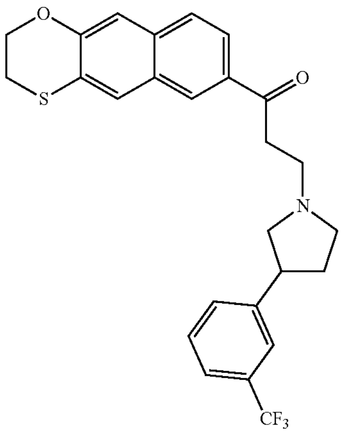 [SMILES: O=C(CCN1CCC(c2cccc(C(F)(F)F)c2)C1)c1ccc2cc3c(cc2c1)SCCO3] 296) |
| 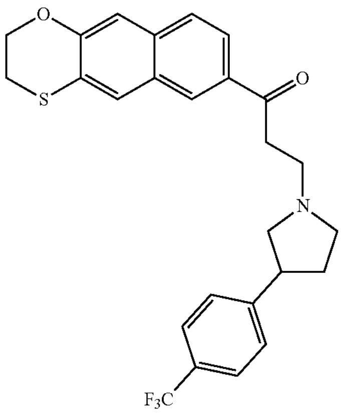 [SMILES: O=C(CCN1CCC(c2ccc(C(F)(F)F)cc2)C1)c1ccc2cc3c(cc2c1)SCCO3] 297) |

TABLE 12-continued
| Structure |
|---|
| 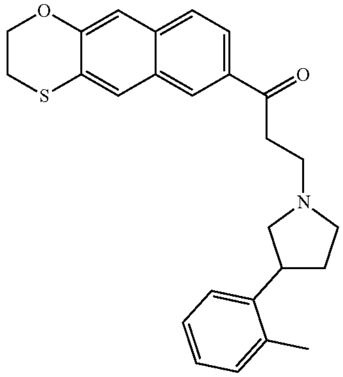 [SMILES: Cc1ccccc1C1CCN(CCC(=O)c2ccc3cc4c(cc3c2)SCCO4)C1] 298) |
| 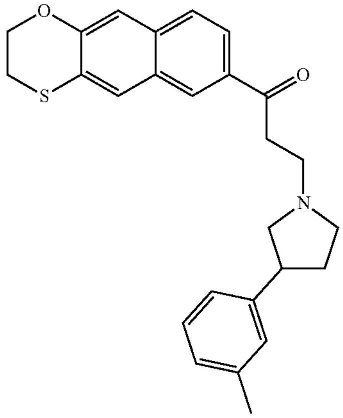 [SMILES: Cc1cccc(C2CCN(CCC(=O)c3ccc4cc5c(cc4c3)SCCO5)C2)c1] 299) |
| 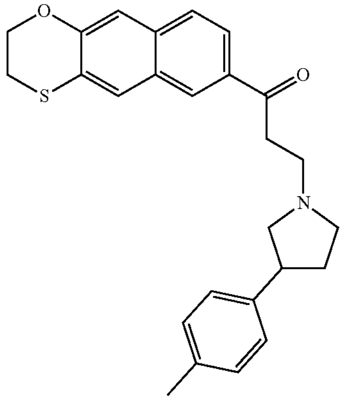 [SMILES: Cc1ccc(C2CCN(CCC(=O)c3ccc4cc5c(cc4c3)SCCO5)C2)cc1] 300) |
| 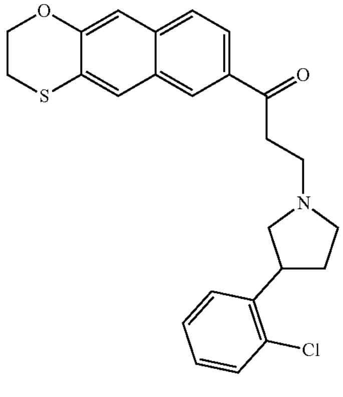 [SMILES: O=C(CCN1CCC(c2ccccc2Cl)C1)c1ccc2cc3c(cc2c1)SCCO3] 301) |
TABLE 12-continued
| Structure |
|---|
| 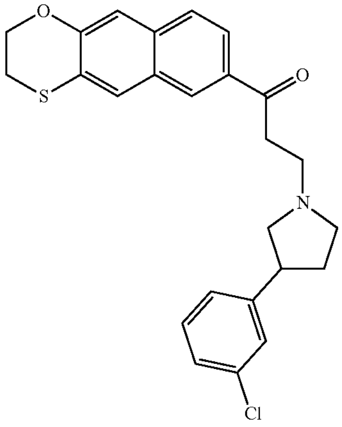 [SMILES: O=C(CCN1CCC(c2cccc(Cl)c2)C1)c1ccc2cc3c(cc2c1)SCCO3] 302) |
| 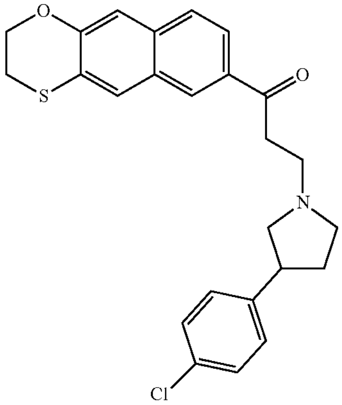 [SMILES: O=C(CCN1CCC(c2ccc(Cl)cc2)C1)c1ccc2cc3c(cc2c1)SCCO3] 303) |
| 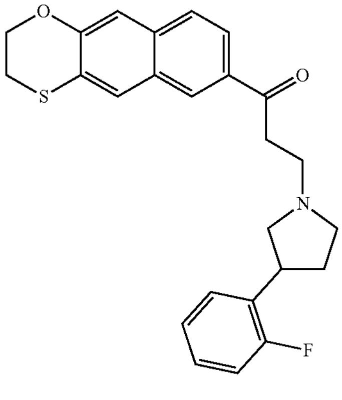 [SMILES: O=C(CCN1CCC(c2ccccc2F)C1)c1ccc2cc3c(cc2c1)SCCO3] 304) |

TABLE 12-continued
| Structure |
|---|
| 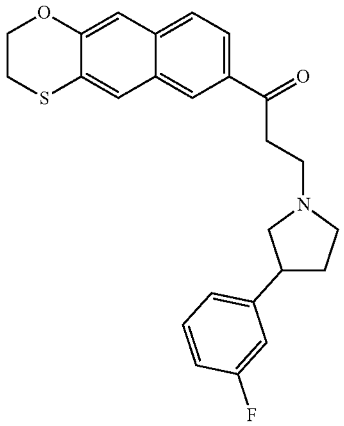 305) |
| 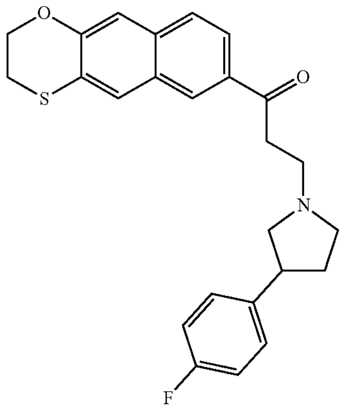 306) |
| 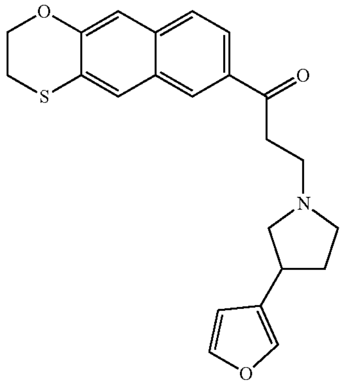 307) |
| 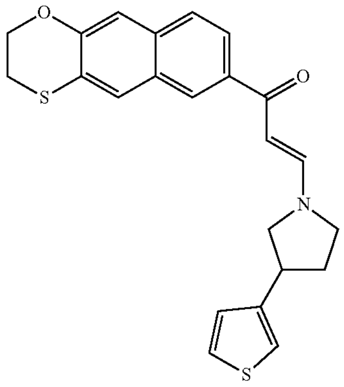 [SMILES: O=C(/C=C/N1CCC(c2ccsc2)C1)c1ccc2cc3c(cc2c1)SCCO3] 308) |
TABLE 12-continued
| Structure |
|---|
| 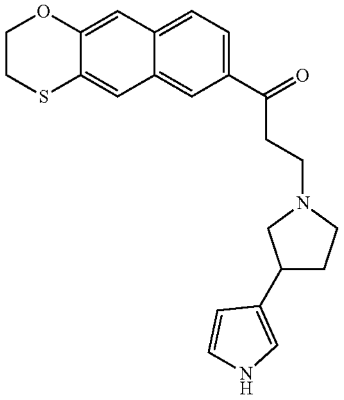 [SMILES: O=C(CCN1CCC(c2cc[nH]c2)C1)c1ccc2cc3c(cc2c1)SCCO3] 309) |
| 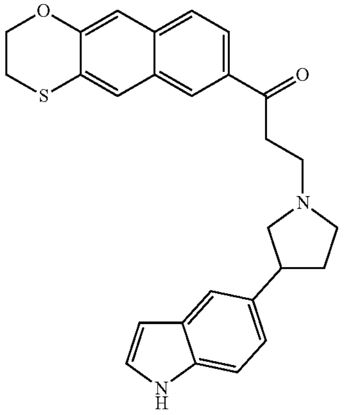 [SMILES: O=C(CCN1CCC(c2ccc3[nH]ccc3c2)C1)c1ccc2cc3c(cc2c1)SCCO3] 310) |
| 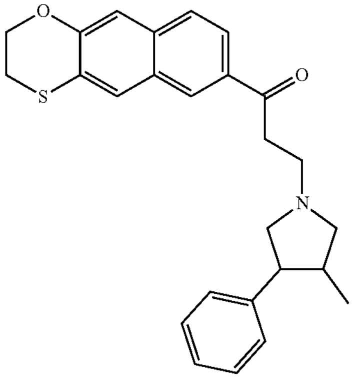 311) |
| 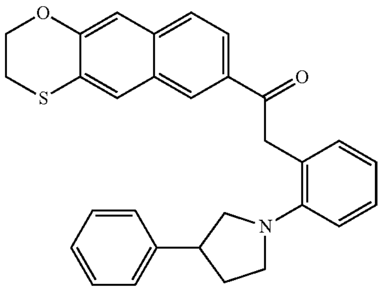 [SMILES: O=C(Cc1ccccc1N1CCC(c2ccccc2)C1)c1ccc2cc3c(cc2c1)SCCO3] 312) |

TABLE 13
| Structure | |
|---|---|
| 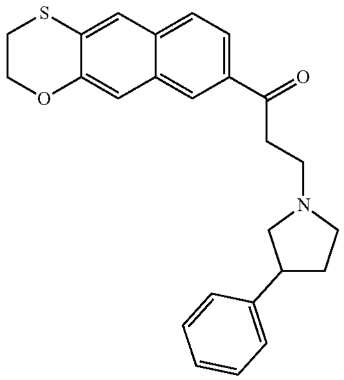 [SMILES: O=C(CCN1CCC(c2ccccc2)C1)c1ccc2cc3c(cc2c1)OCCS3] | 313) |
| 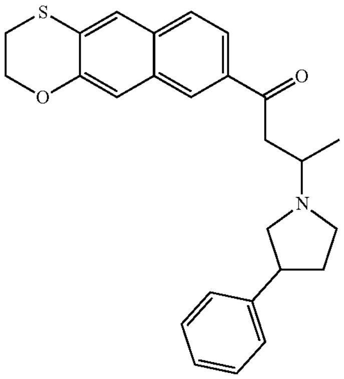 | 314) |
| 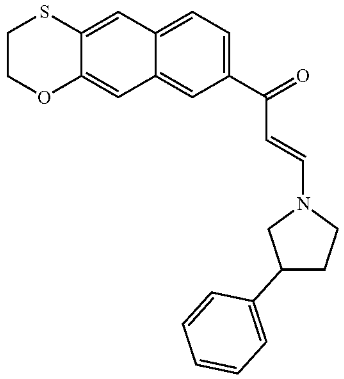 | 315) |
| 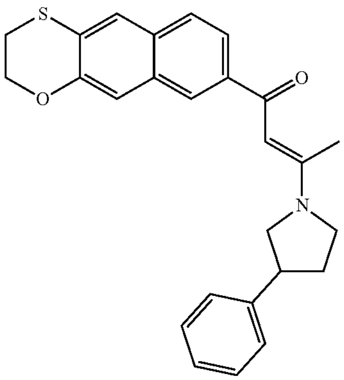 | 316) |
TABLE 13-continued
| Structure | |
|---|---|
| 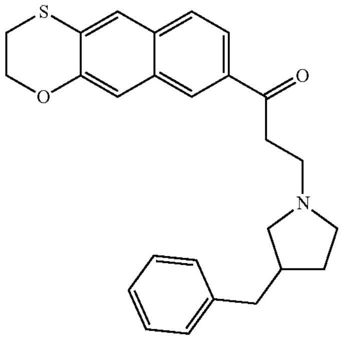 [SMILES: O=C(CCN1CCC(Cc2ccccc2)C1)c1ccc2cc3c(cc2c1)OCCS3] | 317) |
| 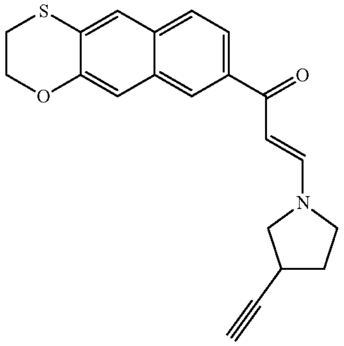 [SMILES: C#CC1CCN(/C=C/C(=O)c2ccc3cc4c(cc3c2)OCCS4)C1] | 318) |
| 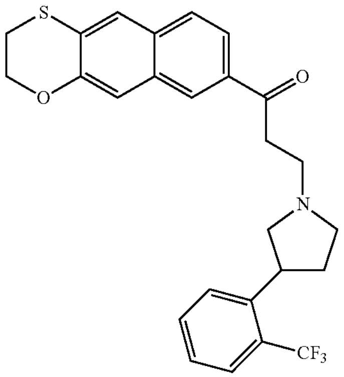 [SMILES: O=C(CCN1CCC(c2ccccc2C(F)(F)F)C1)c1ccc2cc3c(cc2c1)OCCS3] | 319) |
| 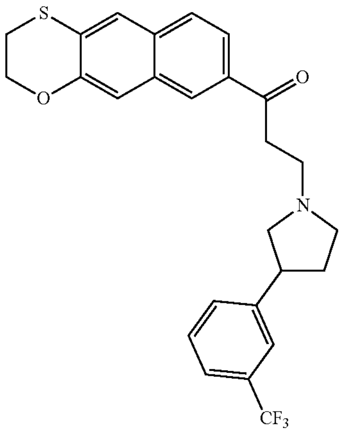 [SMILES: O=C(CCN1CCC(c2cccc(C(F)(F)F)c2)C1)c1ccc2cc3c(cc2c1)OCCS3] | 320) |

TABLE 13-continued
| Structure | |
|---|---|
| 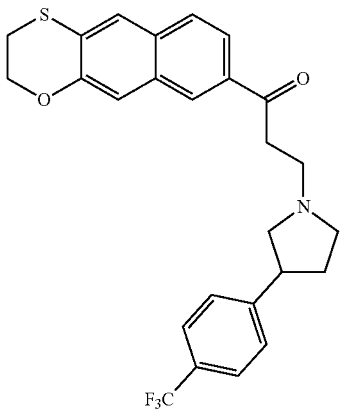 [SMILES: O=C(CCN1CCC(c2ccc(C(F)(F)F)cc2)C1)c1ccc2cc3c(cc2c1)OCCS3] | 321) |
| 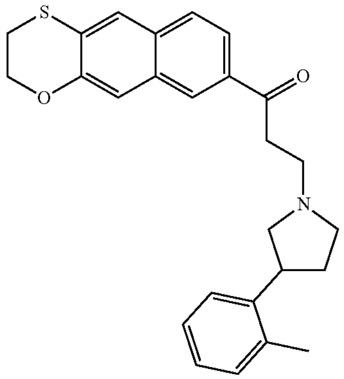 | 322) |
| 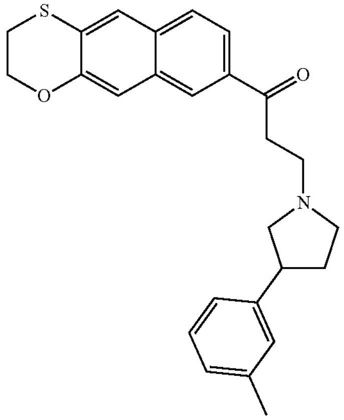 [SMILES: Cc1cccc(C2CCN(CCC(=O)c3ccc4cc5c(cc4c3)OCCS5)C2)c1] | 323) |
| 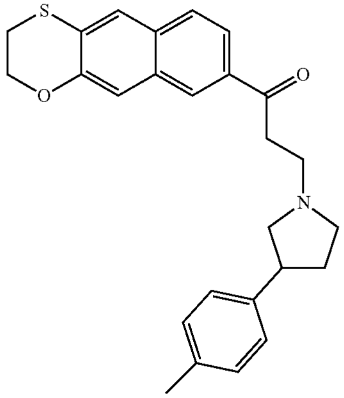 [SMILES: Cc1ccc(C2CCN(CCC(=O)c3ccc4cc5c(cc4c3)OCCS5)C2)cc1] | 324) |
| 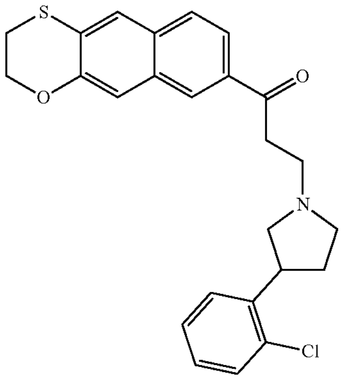 [SMILES: O=C(CCN1CCC(c2ccccc2Cl)C1)c1ccc2cc3c(cc2c1)OCCS3] | 325) |
| 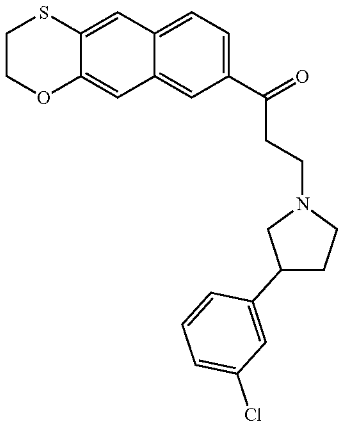 [SMILES: O=C(CCN1CCC(c2cccc(Cl)c2)C1)c1ccc2cc3c(cc2c1)OCCS3] | 326) |
| 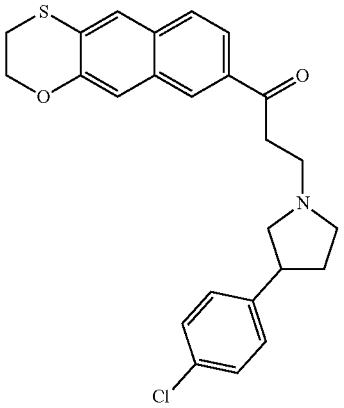 [SMILES: O=C(CCN1CCC(c2ccc(Cl)cc2)C1)c1ccc2cc3c(cc2c1)OCCS3] | 327) |
| 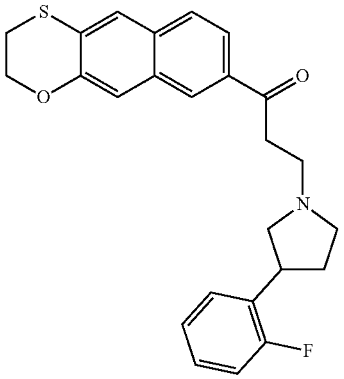 | 328) |

TABLE 13-continued
| Structure |
| --- |
| 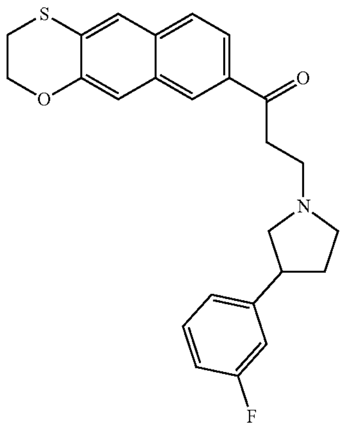 [SMILES: O=C(CCN1CCC(c2cccc(F)c2)C1)c1ccc2cc3c(cc2c1)OCCS3] 329) |
| 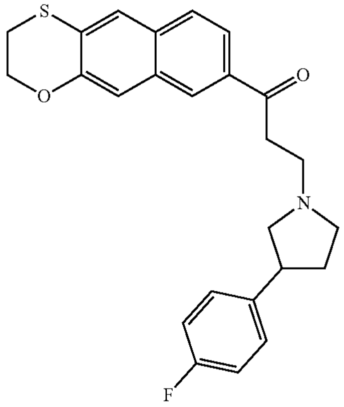 [SMILES: O=C(CCN1CCC(c2ccc(F)cc2)C1)c1ccc2cc3c(cc2c1)OCCS3] 330) |
| 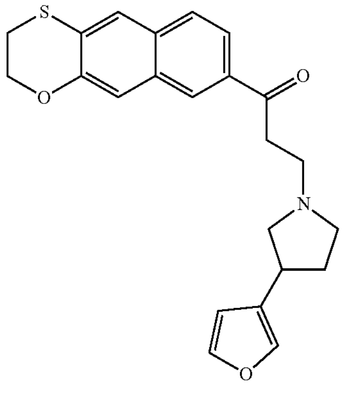 331) |
TABLE 13-continued
| Structure |
| --- |
| 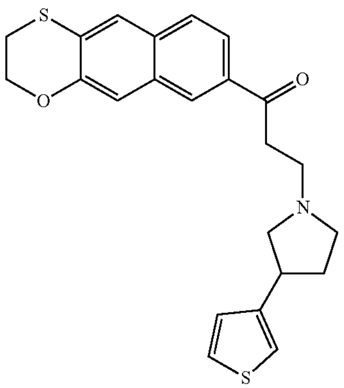 [SMILES: O=C(CCN1CCC(c2ccoc2)C1)c1ccc2cc3c(cc2c1)OCCS3] 332) |
| 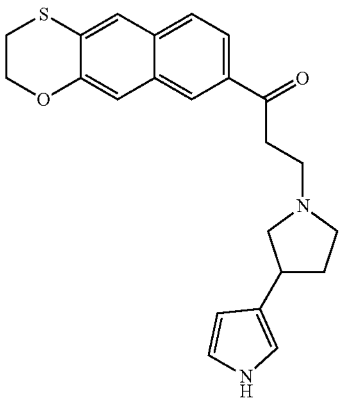 [SMILES: O=C(CCN1CCC(c2cc[nH]c2)C1)c1ccc2cc3c(cc2c1)OCCS3] 333) |
| 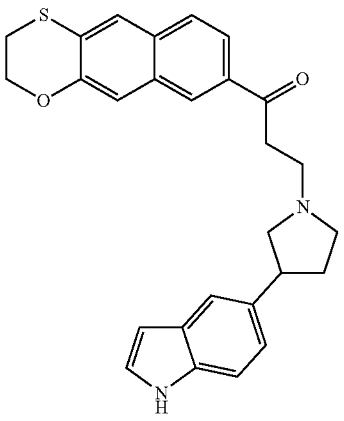 [SMILES: O=C(CCN1CCC(c2ccc3[nH]ccc3c2)C1)c1ccc2cc3c(cc2c1)OCCS3] 334) |
| 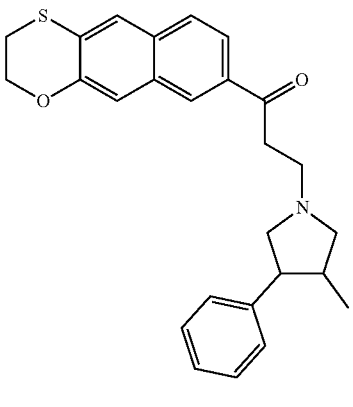 [SMILES: CC1CN(CCC(=O)c2ccc3cc4c(cc3c2)OCCS4)CC1c1ccccc1] 335) |

TABLE 13-continued
| Structure | |
|---|---|
| 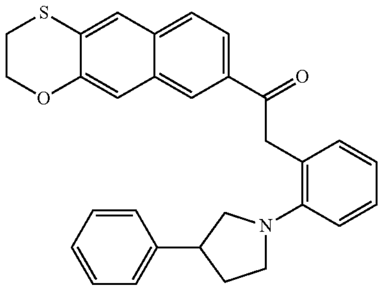 | 336) |
TABLE 14
| Structure | |
|---|---|
| 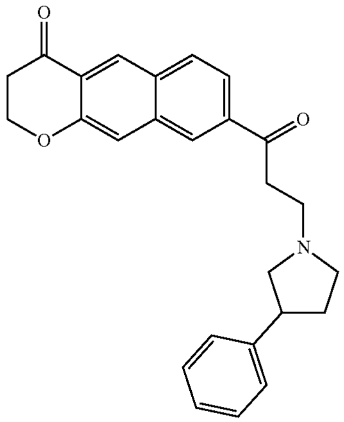 [SMILES: O=C(CCN1CCC(c2ccccc2)C1)c1ccc2cc3c(cc2c1)OCCC3=O] | 337) |
| 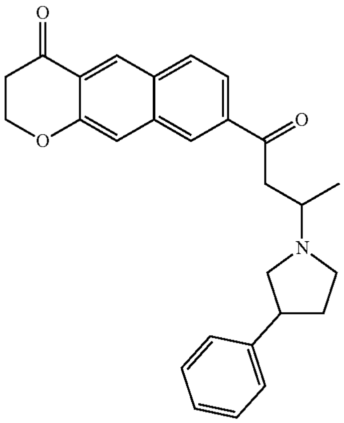 [SMILES: CC(CC(=O)c1ccc2cc3c(cc2c1)OCCC3=O)N1CCC(c2ccccc2)C1] | 338) |
TABLE 14-continued
| Structure | |
|---|---|
| 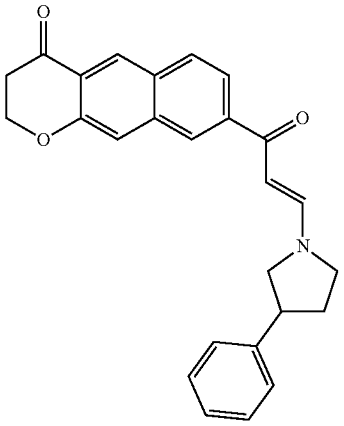 [SMILES: O=C(/C=C/N1CCC(c2ccccc2)C1)c1ccc2cc3c(cc2c1)OCCC3=O] | 339) |
| 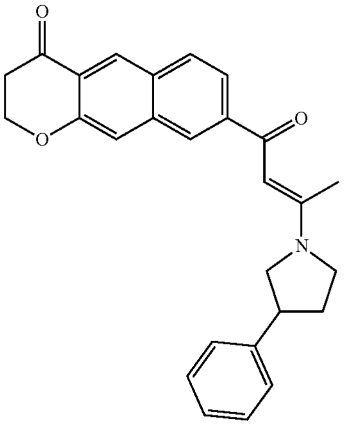 [SMILES: C/C(=C\C(=O)c1ccc2cc3c(cc2c1)OCCC3=O)N1CCC(c2ccccc2)C1] | 340) |
| 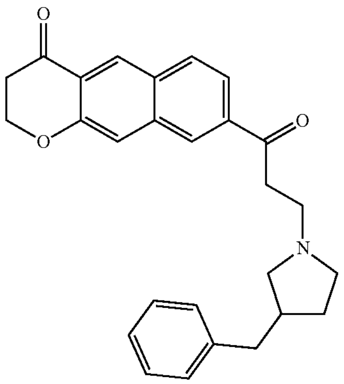 [SMILES: O=C(CCN1CCC(Cc2ccccc2)C1)c1ccc2cc3c(cc2c1)OCCC3=O] | 341) |

TABLE 14-continued
| Structure |
|---|
| 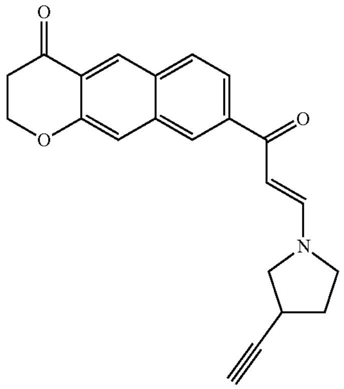 [SMILES: C#CC1CCN(/C=C/C(=O)c2ccc3cc4c(cc3c2)OCCC4=O)C1] 342) |
| 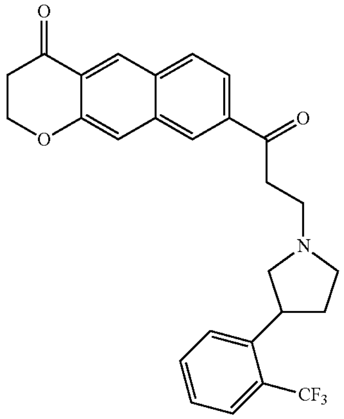 [SMILES: O=C(CCN1CCC(c2ccccc2C(F)(F)F)C1)c1ccc2cc3c(cc2c1)OCCC3=O] 343) |
| 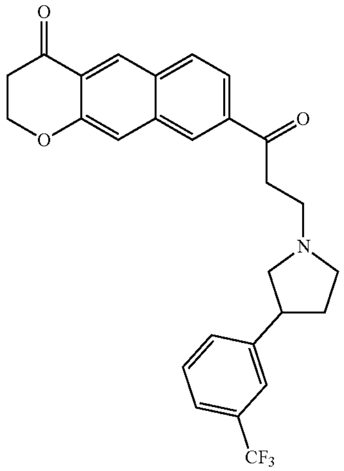 [SMILES: O=C(CCN1CCC(c2cccc(C(F)(F)F)c2)C1)c1ccc2cc3c(cc2c1)OCCC3=O] 344) |
TABLE 14-continued
| Structure |
|---|
| 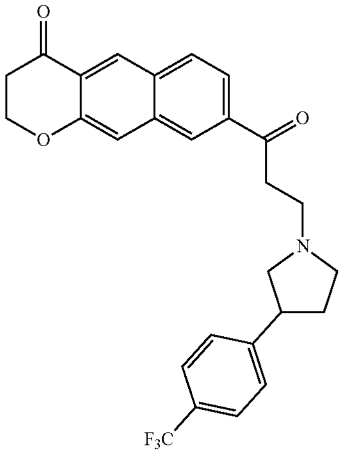 [SMILES: O=C(CCN1CCC(c2ccc(C(F)(F)F)cc2)C1)c1ccc2cc3c(cc2c1)OCCC3=O] 345) |
| 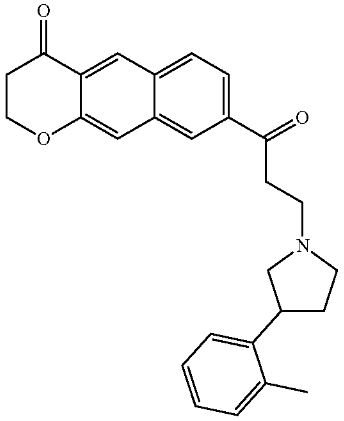 [SMILES: Cc1ccccc1C1CCN(CCC(=O)c2ccc3cc4c(cc3c2)OCCC4=O)C1] 346) |
| 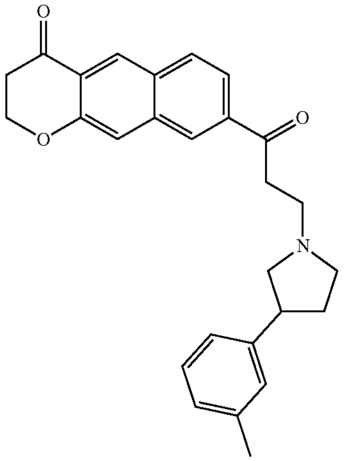 [SMILES: Cc1cccc(C2CCN(CCC(=O)c3ccc4cc5c(cc4c3)OCCC5=O)C2)c1] 347) |

TABLE 14-continued
| Structure | |
| --- | --- |
| 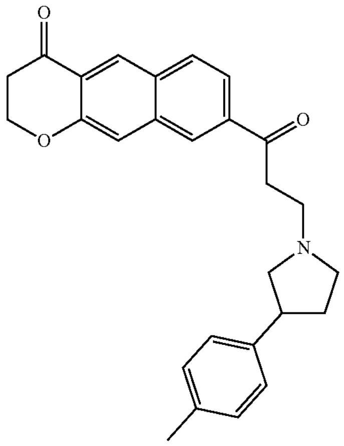 [SMILES: Cc1ccc(C2CCN(CCC(=O)c3ccc4cc5c(cc4c3)OCCC5=O)C2)cc1] | 348) |
| 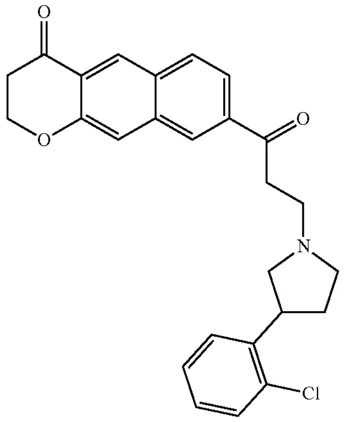 [SMILES: O=C(CCN1CCC(c2ccccc2Cl)C1)c1ccc2cc3c(cc2c1)OCCC3=O] | 349) |
| 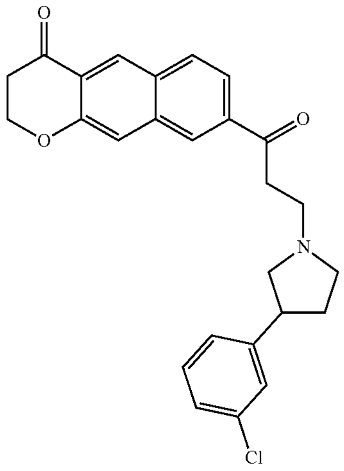 [SMILES: O=C(CCN1CCC(c2cccc(Cl)c2)C1)c1ccc2cc3c(cc2c1)OCCC3=O] | 350) |
TABLE 14-continued
| Structure | |
| --- | --- |
| 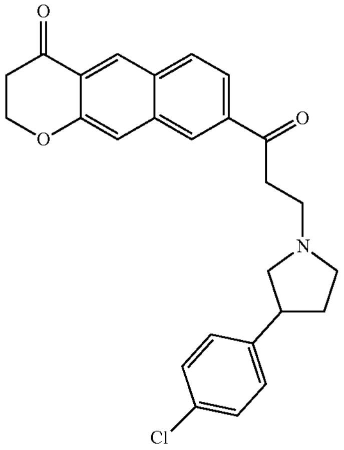 [SMILES: O=C(CCN1CCC(c2ccc(Cl)cc2)C1)c1ccc2cc3c(cc2c1)OCCC3=O] | 351) |
| 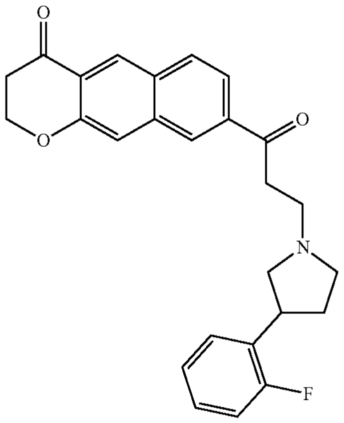 [SMILES: O=C(CCN1CCC(c2ccccc2F)C1)c1ccc2cc3c(cc2c1)OCCC3=O] | 352) |
| 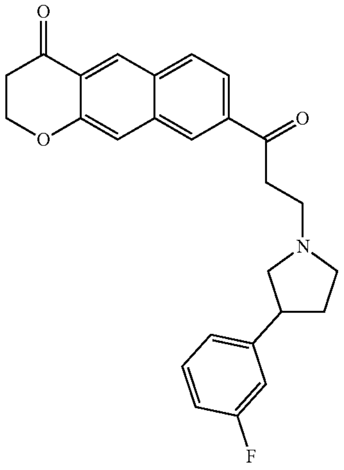 [SMILES: O=C(CCN1CCC(c2cccc(F)c2)C1)c1ccc2cc3c(cc2c1)OCCC3=O] | 353) |

TABLE 14-continued
| Structure |
|---|
| 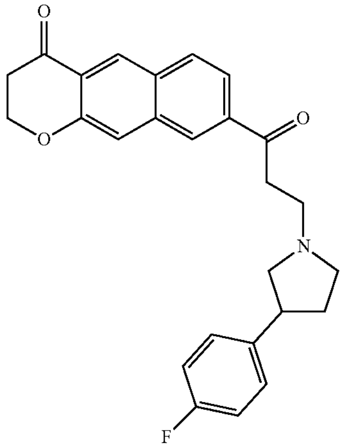 [SMILES: O=C(CCN1CCC(c2ccc(F)cc2)C1)c1ccc2cc3c(cc2c1)OCCC3=O] 354) |
| 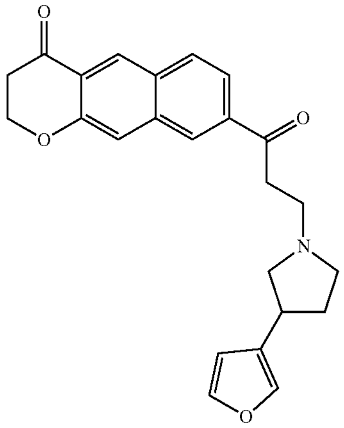 [SMILES: O=C(CCN1CCC(c2ccoc2)C1)c1ccc2cc3c(cc2c1)OCCC3=O] 355) |
| 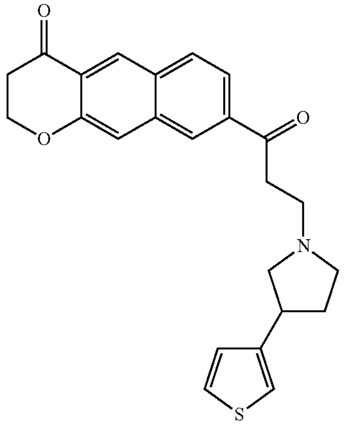 [SMILES: O=C(CCN1CCC(c2ccsc2)C1)c1ccc2cc3c(cc2c1)OCCC3=O] 356) |
TABLE 14-continued
| Structure |
|---|
| 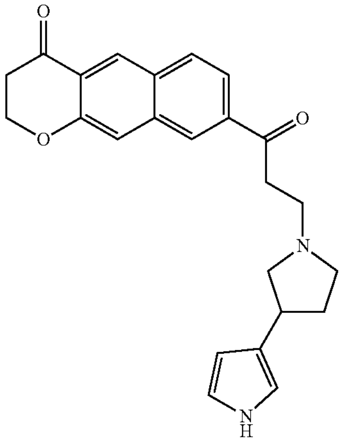 [SMILES: O=C(CCN1CCC(c2cc[nH]c2)C1)c1ccc2cc3c(cc2c1)OCCC3=O] 357) |
| 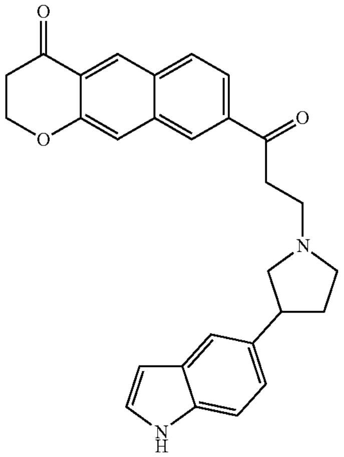 [SMILES: O=C(CCN1CCC(c2ccc3[nH]ccc3c2)C1)c1ccc2cc3c(cc2c1)OCCC3=O] 358) |
| 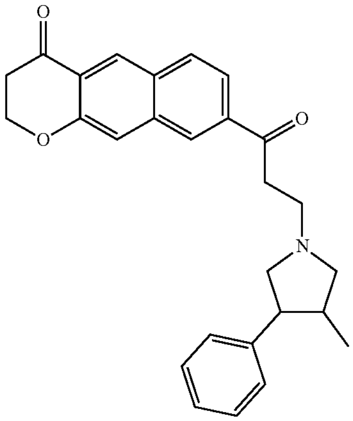 [SMILES: CC1CN(CCC(=O)c2ccc3cc4c(cc3c2)OCCC4=O)CC1c1ccccc1] 359) |

TABLE 14-continued
| Structure | |
|---|---|
| 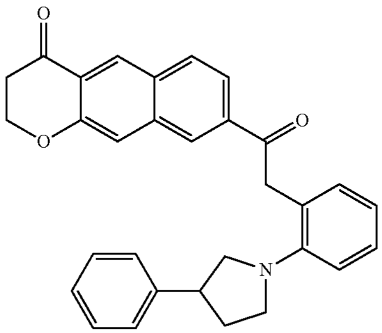 [SMILES: O=C(Cc1ccccc1N1CCC(c2ccccc2)C1)c1ccc2cc3c(cc2c1)OCCC3=O] | 360) |
TABLE 15
| Structure | |
|---|---|
| 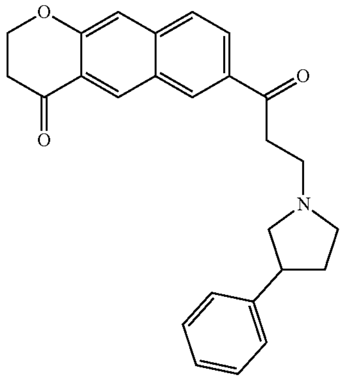 [SMILES: O=C(CCN1CCC(c2ccccc2)C1)c1ccc2cc3c(cc2c1)C(=O)CCO3] | 361) |
| 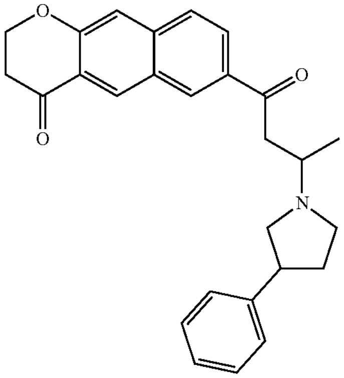 [SMILES: CC(CC(=O)c1ccc2cc3c(cc2c1)C(=O)CCO3)N1CCC(c2ccccc2)C1] | 362) |
| 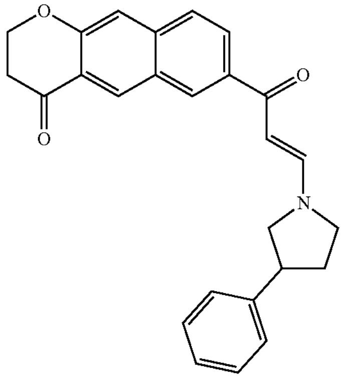 [SMILES: O=C(/C=C/N1CCC(c2ccccc2)C1)c1ccc2cc3c(cc2c1)C(=O)CCO3] | 363) |
TABLE 15-continued
| Structure | |
|---|---|
| 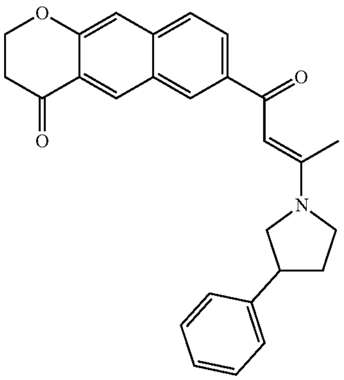 [SMILES: C/C(=C\C(=O)c1ccc2cc3c(cc2c1)C(=O)CCO3)N1CCC(c2ccccc2)C1] | 364) |
| 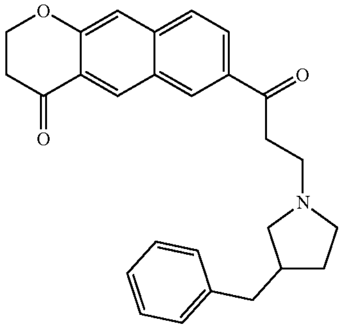 [SMILES: O=C(CCN1CCC(Cc2ccccc2)C1)c1ccc2cc3c(cc2c1)C(=O)CCO3] | 365) |
| 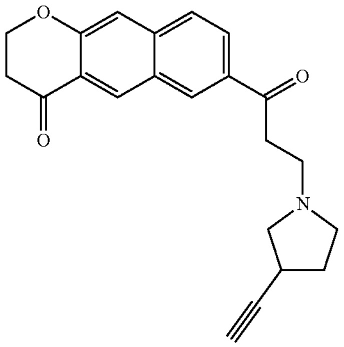 [SMILES: C#CC1CCN(CCC(=O)c2ccc3cc4c(cc3c2)C(=O)CCO4)C1] | 366) |
| 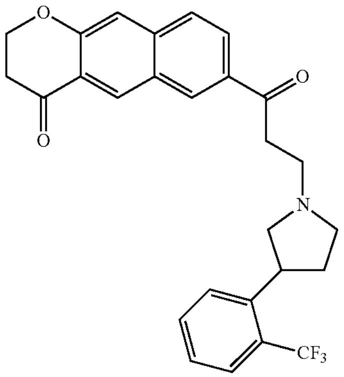 [SMILES: O=C(CCN1CCC(c2ccccc2C(F)(F)F)C1)c1ccc2cc3c(cc2c1)C(=O)CCO3] | 367) |

TABLE 15-continued
| Structure |
| --- |
| 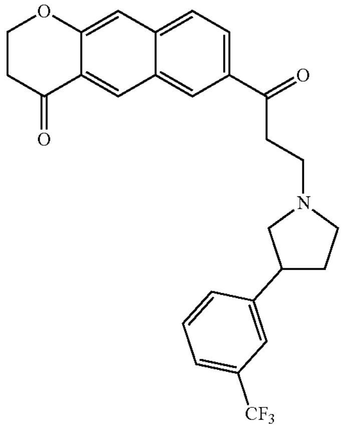 [SMILES: O=C(CCN1CCC(c2cccc(C(F)(F)F)c2)C1)c1ccc2cc3c(cc2c1)C(=O)CCO3] 368) |
| 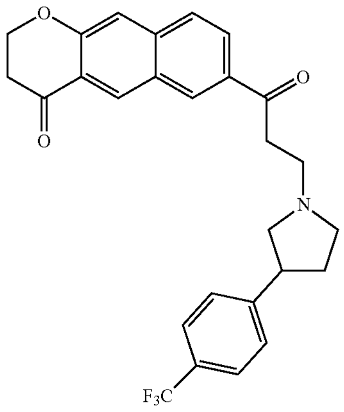 [SMILES: O=C(CCN1CCC(c2ccc(C(F)(F)F)cc2)C1)c1ccc2cc3c(cc2c1)C(=O)CCO3] 369) |
| 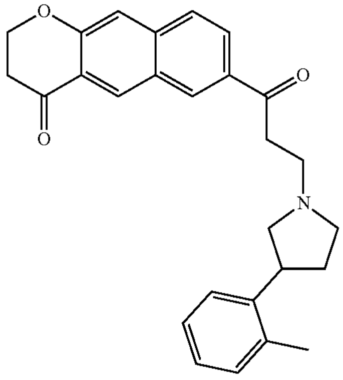 [SMILES: Cc1ccccc1C1CCN(CCC(=O)c2ccc3cc4c(cc3c2)C(=O)CCO4)C1] 370) |
TABLE 15-continued
| Structure |
| --- |
| 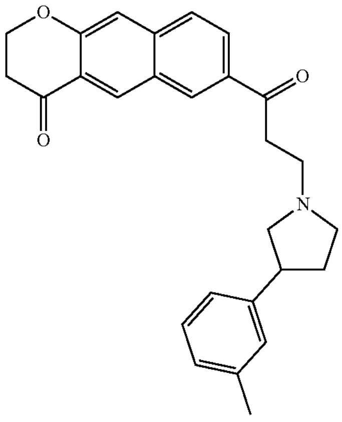 [SMILES: Cc1cccc(C2CCN(CCC(=O)c3ccc4cc5c(cc4c3)C(=O)CCO5)C2)c1] 371) |
| 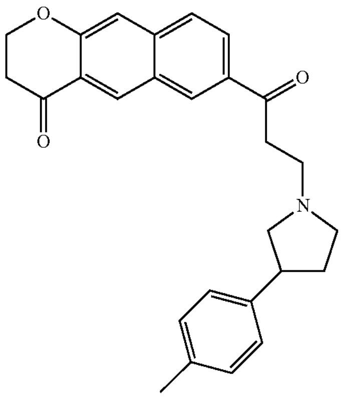 [SMILES: Cc1ccc(C2CCN(CCC(=O)c3ccc4cc5c(cc4c3)C(=O)CCO5)C2)cc1] 372) |
| 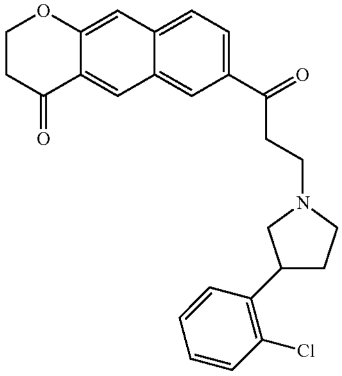 [SMILES: O=C(CCN1CCC(c2ccccc2Cl)C1)c1ccc2cc3c(cc2c1)C(=O)CCO3] 373) |

TABLE 15-continued
| Structure |
| --- |
| 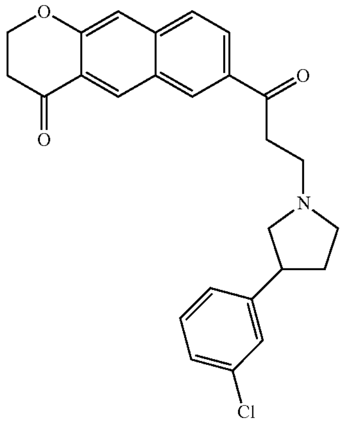 [SMILES: O=C(CCN1CCC(c2cccc(Cl)c2)C1)c1ccc2cc3c(cc2c1)C(=O)CCO3] 374) |
| 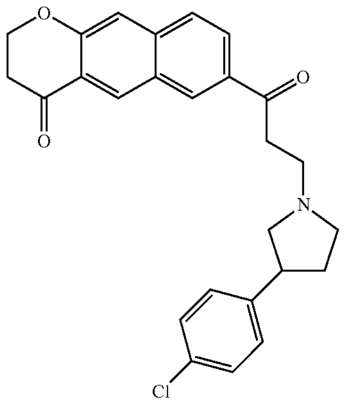 [SMILES: O=C(CCN1CCC(c2ccc(Cl)cc2)C1)c1ccc2cc3c(cc2c1)C(=O)CCO3] 375) |
| 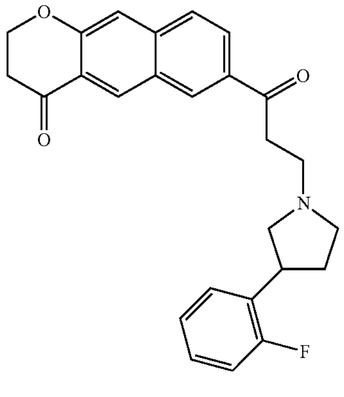 [SMILES: O=C(CCN1CCC(c2ccccc2F)C1)c1ccc2cc3c(cc2c1)C(=O)CCO3] 376) |
TABLE 15-continued
| Structure |
| --- |
| 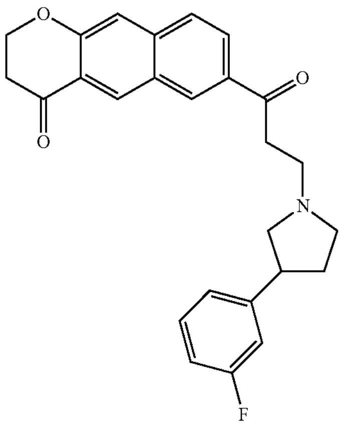 [SMILES: O=C(CCN1CCC(c2cccc(F)c2)C1)c1ccc2cc3c(cc2c1)C(=O)CCO3] 377) |
| 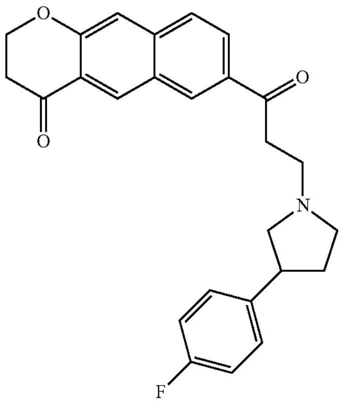 [SMILES: O=C(CCN1CCC(c2ccc(F)cc2)C1)c1ccc2cc3c(cc2c1)C(=O)CCO3] 378) |
| 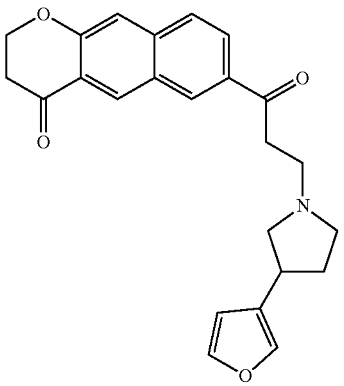 [SMILES: O=C(CCN1CCC(c2ccoc2)C1)c1ccc2cc3c(cc2c1)C(=O)CCO3] 379) |
| 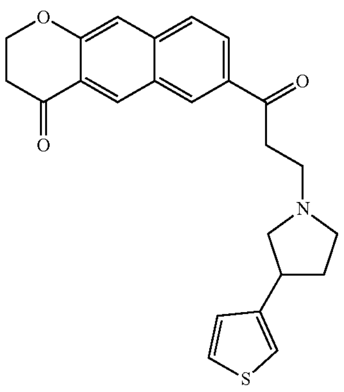 [SMILES: O=C(CCN1CCC(c2ccsc2)C1)c1ccc2cc3c(cc2c1)C(=O)CCO3] 380) |

TABLE 15-continued
| Structure | |
|---|---|
| 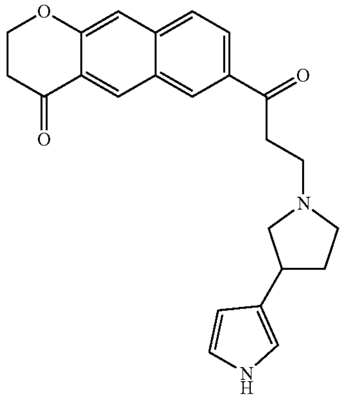 | 381) |
| 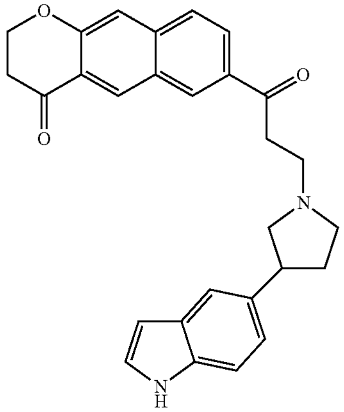 [SMILES: O=C(CCN1CCC(c2ccc3[nH]ccc3c2)C1)c1ccc2cc3c(cc2c1)C(=O)CCO3] | 382) |
| 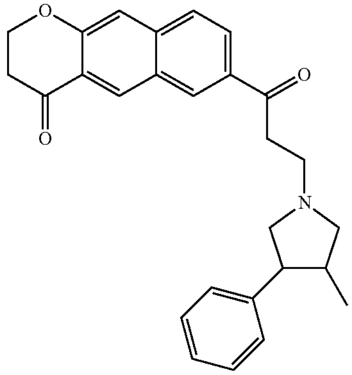 [SMILES: CC1CN(CCC(=O)c2ccc3cc4c(cc3c2)C(=O)CCO4)CC1c1ccccc1] | 383) |
| 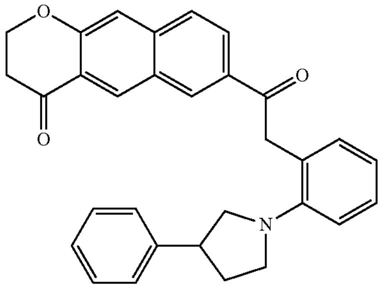 [SMILES: O=C(Cc1ccccc1N1CCC(c2ccccc2)C1)c1ccc2cc3c(cc2c1)C(=O)CCO3] | 384) |
TABLE 16
| Structure | |
|---|---|
| 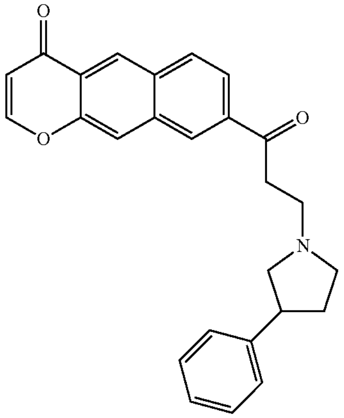 [SMILES: O=C(CCN1CCC(c2ccccc2)C1)c1ccc2cc3c(=O)ccoc3cc2c1] | 385) |
| 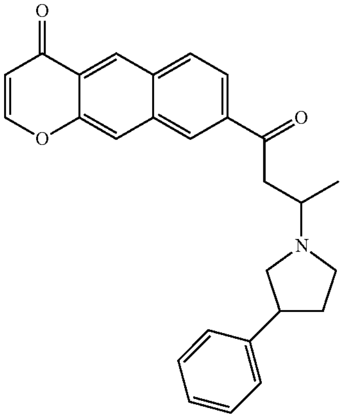 [SMILES: CC(CC(=O)c1ccc2cc3c(=O)ccoc3cc2c1)N1CCC(c2ccccc2)C1] | 386) |
| 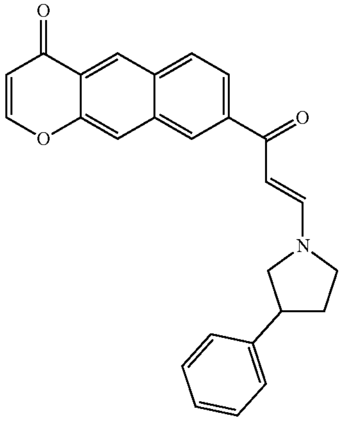 [SMILES: O=C(/C=C/N1CCC(c2ccccc2)C1)c1ccc2cc3c(=O)ccoc3cc2c1] | 387) |

TABLE 16-continued
| Structure |
| --- |
| 388) 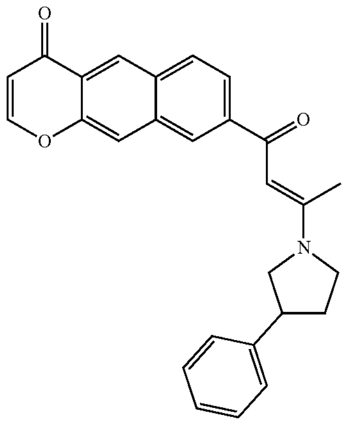 [SMILES: C/C(=C\C(=O)c1ccc2cc3c(=O)ccoc3cc2c1)N1CCC(c2ccccc2)C1] |
| 389) 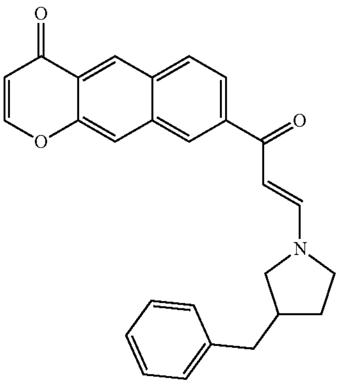 [SMILES: O=C(/C=C/N1CCC(Cc2ccccc2)C1)c1ccc2cc3c(=O)ccoc3cc2c1] |
| 390) 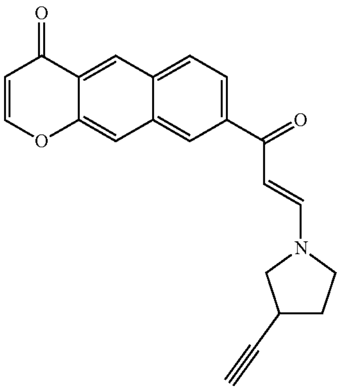 [SMILES: C#CC1CCN(/C=C/C(=O)c2ccc3cc4c(=O)ccoc4cc3c2)C1] |
TABLE 16-continued
| Structure |
| --- |
| 391) 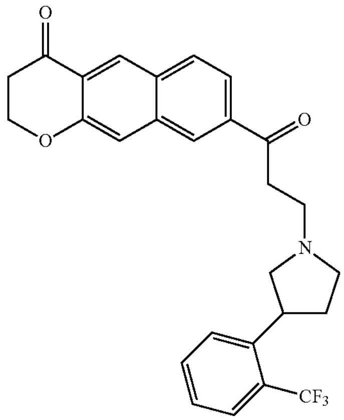 [SMILES: O=C(CCN1CCC(c2ccccc2C(F)(F)F)C1)c1ccc2cc3c(cc2c1)OCCC3=O] |
| 392) 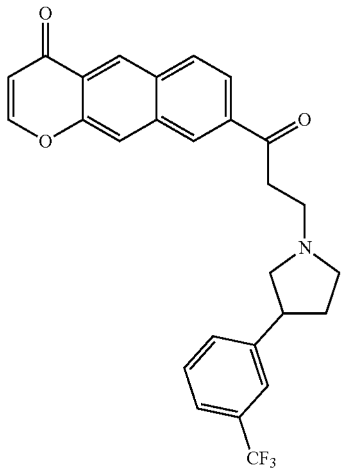 [SMILES: O=C(CCN1CCC(c2cccc(C(F)(F)F)c2)C1)c1ccc2cc3c(=O)ccoc3cc2c1] |
| 393) 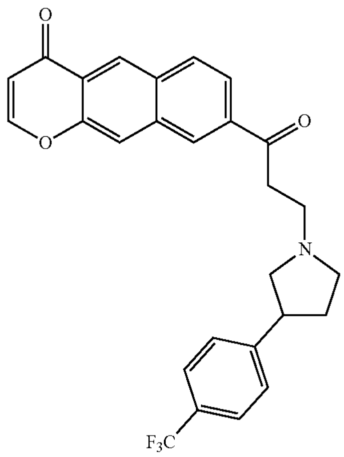 [SMILES: O=C(CCN1CCC(c2ccc(C(F)(F)F)cc2)C1)c1ccc2cc3c(=O)ccoc3cc2c1] |

TABLE 16-continued
| Structure | |
|---|---|
| 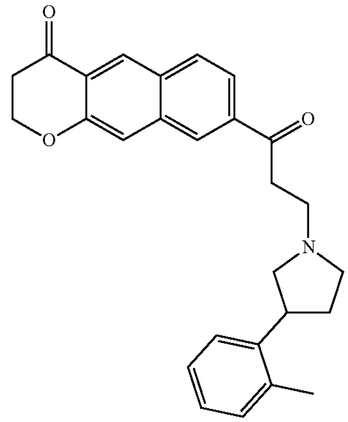 [SMILES: Cc1ccccc1C1CCN(CCC(=O)c2ccc3cc4c(cc3c2)OCCC4=O)C1] | 394) |
| 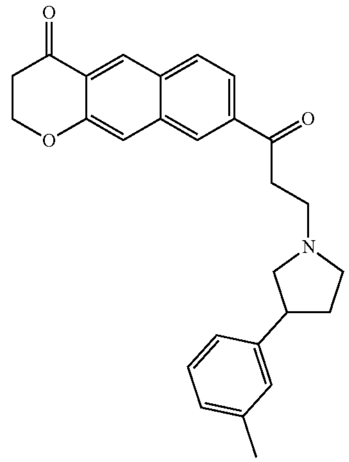 [SMILES: Cc1cccc(C2CCN(CCC(=O)c3ccc4cc5c(cc4c3)OCCC5=O)C2)c1] | 395) |
| 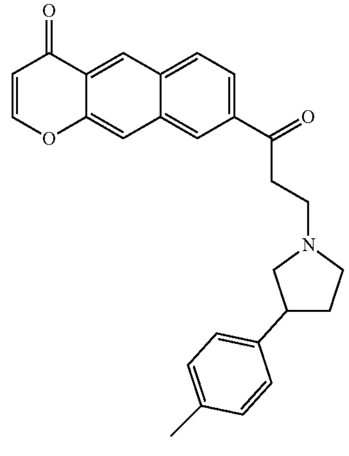 [SMILES: Cc1ccc(C2CCN(CCC(=O)c3ccc4cc5c(=O)ccoc5cc4c3)C2)cc1] | 396) |
| 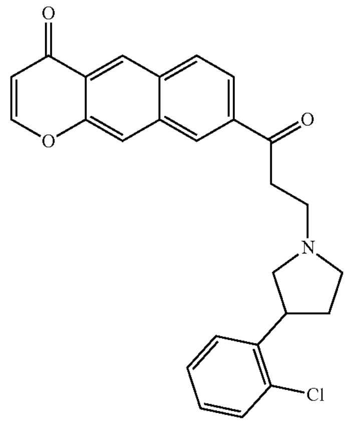 [SMILES: O=C(CCN1CCC(c2ccccc2Cl)C1)c1ccc2cc3c(=O)ccoc3cc2c1] | 397) |
| 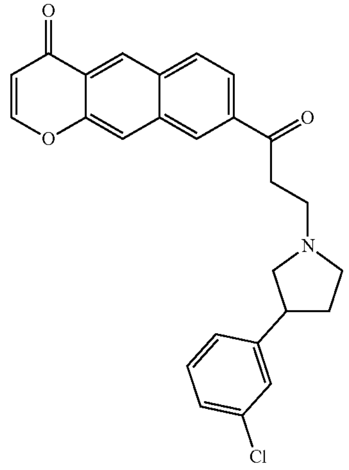 [SMILES: O=C(CCN1CCC(c2cccc(Cl)c2)C1)c1ccc2cc3c(=O)ccoc3cc2c1] | 398) |
| 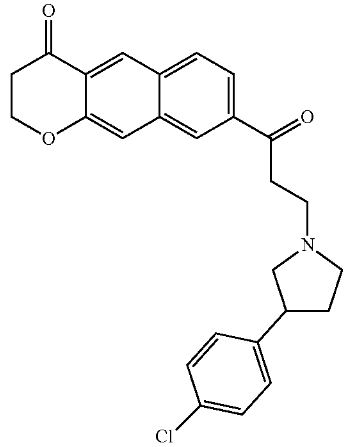 [SMILES: O=C(CCN1CCC(c2ccc(Cl)cc2)C1)c1ccc2cc3c(cc2c1)OCCC3=O] | 399) |

TABLE 16-continued
| Structure |
|---|
| 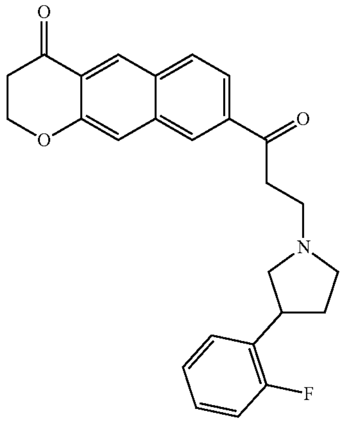 [SMILES: O=C(CCN1CCC(c2ccccc2F)C1)c1ccc2cc3c(cc2c1)OCCC3=O] 400) |
| 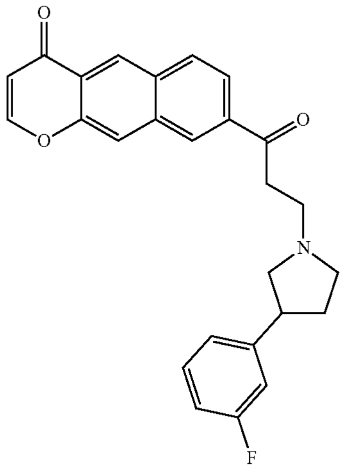 [SMILES: O=C(CCN1CCC(c2cccc(F)c2)C1)c1ccc2cc3c(=O)ccoc3cc2c1] 401) |
| 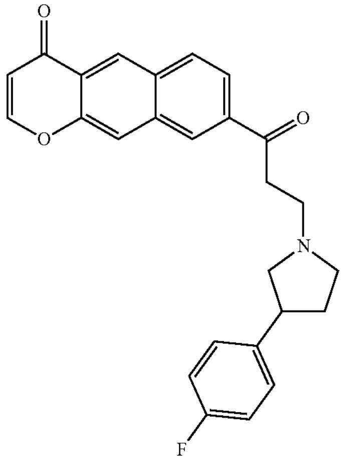 [SMILES: O=C(CCN1CCC(c2ccc(F)cc2)C1)c1ccc2cc3c(=O)ccoc3cc2c1] 402) |
TABLE 16-continued
| Structure |
|---|
| 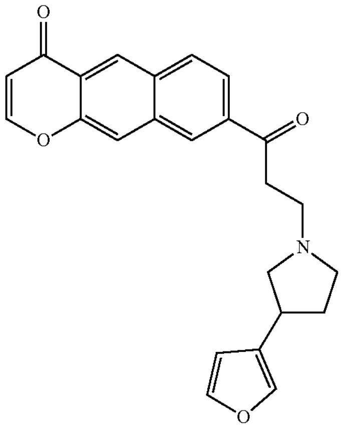 [SMILES: O=C(CCN1CCC(c2ccoc2)C1)c1ccc2cc3c(=O)ccoc3cc2c1] 403) |
| 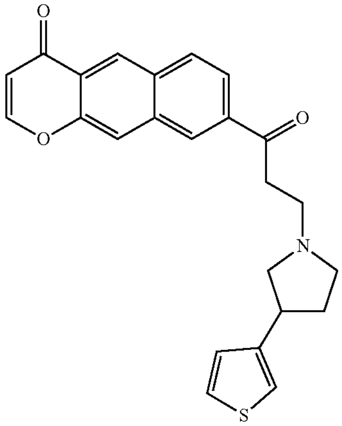 [SMILES: O=C(CCN1CCC(c2ccsc2)C1)c1ccc2cc3c(=O)ccoc3cc2c1] 404) |
| 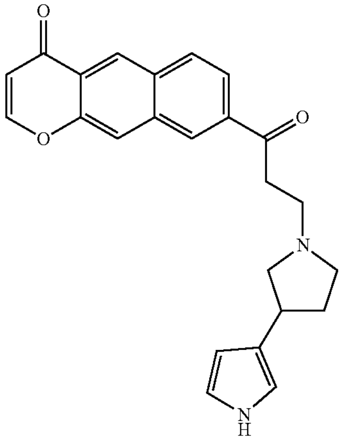 [SMILES: O=C(CCN1CCC(c2cc[nH]c2)C1)c1ccc2cc3c(=O)ccoc3cc2c1] 405) |

TABLE 16-continued
| Structure |
|---|
| 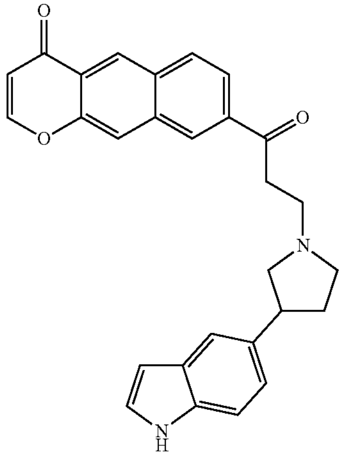 [SMILES: O=C(CCN1CCC(c2ccc3[nH]ccc3c2)C1)c1ccc2cc3c(=O)ccoc3cc2c1] 406) |
| 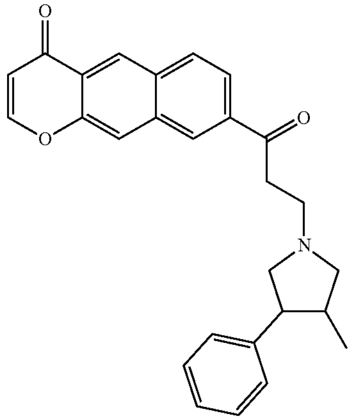 [SMILES: CC1CN(CCC(=O)c2ccc3cc4c(=O)ccoc4cc3c2)CC1c1ccccc1] 407) |
| 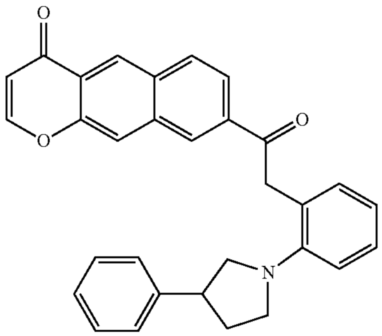 [SMILES: O=C(Cc1ccccc1N1CCC(c2ccccc2)C1)c1ccc2cc3c(=O)ccoc3cc2c1] 408) |
TABLE 17
| Structure |
|---|
| 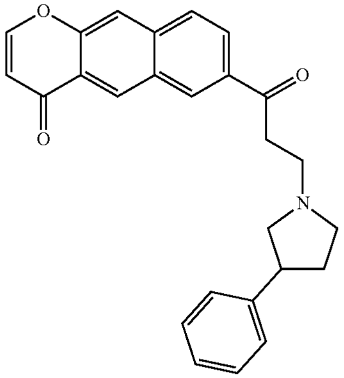 [SMILES: O=C(CCN1CCC(c2ccccc2)C1)c1ccc2cc3occc(=O)c3cc2c1] 409) |
| 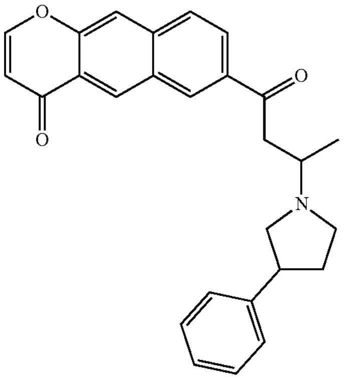 [SMILES: CC(CC(=O)c1ccc2cc3occc(=O)c3cc2c1)N1CCC(c2ccccc2)C1] 410) |
| 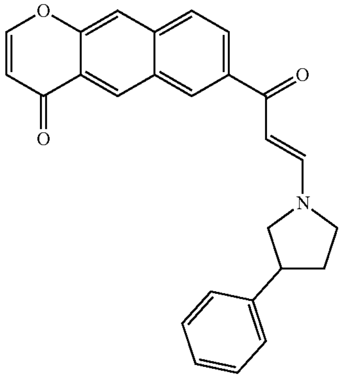 [SMILES: O=C(/C=C/N1CCC(c2ccccc2)C1)c1ccc2cc3occc(=O)c3cc2c1] 411) |
| 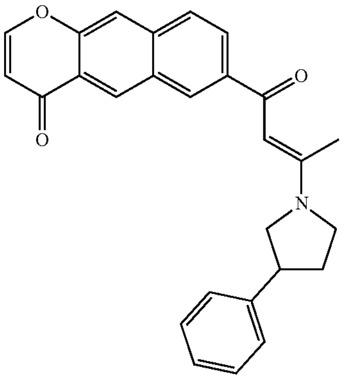 [SMILES: C/C(=C\C(=O)c1ccc2cc3occc(=O)c3cc2c1)N1CCC(c2ccccc2)C1] 412) |

TABLE 17-continued
| Structure |
|---|
| 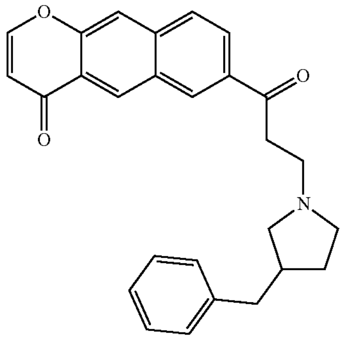 [SMILES: O=C(CCN1CCC(Cc2ccccc2)C1)c1ccc2cc3occc(=O)c3cc2c1] 413) |
| 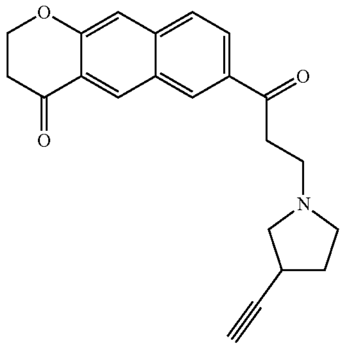 [SMILES: C#CC1CCN(CCC(=O)c2ccc3cc4c(cc3c2)C(=O)CCO4)C1] 414) |
| 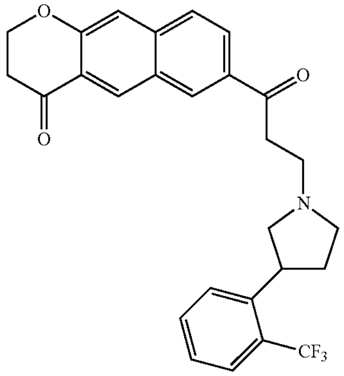 [SMILES: O=C(CCN1CCC(c2ccccc2C(F)(F)F)C1)c1ccc2cc3c(cc2c1)C(=O)CCO3] 415) |
| 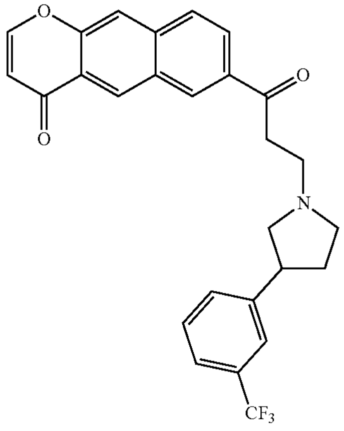 [SMILES: O=C(CCN1CCC(c2cccc(C(F)(F)F)c2)C1)c1ccc2cc3occc(=O)c3cc2c1] 416) |
TABLE 17-continued
| Structure |
|---|
| 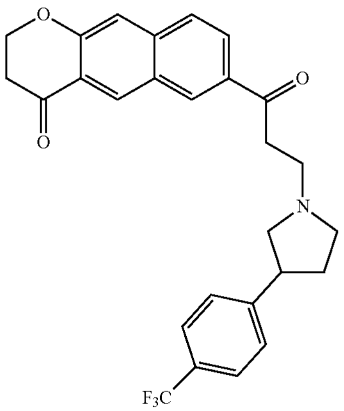 [SMILES: O=C(CCN1CCC(c2ccc(C(F)(F)F)cc2)C1)c1ccc2cc3c(cc2c1)C(=O)CCO3] 417) |
| 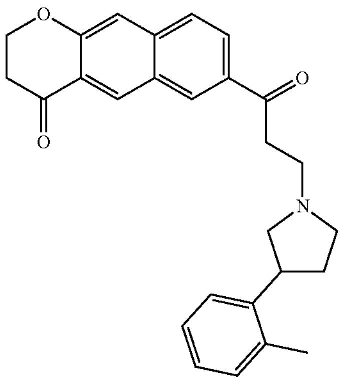 [SMILES: Cc1ccccc1C1CCN(CCC(=O)c2ccc3cc4c(cc3c2)C(=O)CCO4)C1] 418) |
| 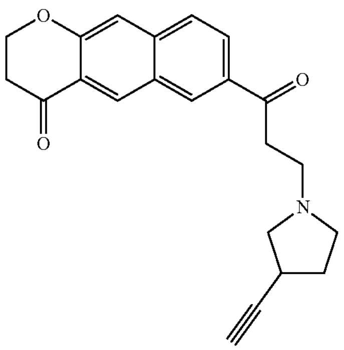 [SMILES: C#CC1CCN(CCC(=O)c2ccc3cc4c(cc3c2)C(=O)CCO4)C1] 419) |
| 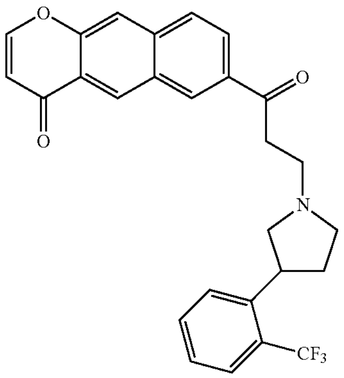 [SMILES: O=C(CCN1CCC(c2ccccc2C(F)(F)F)C1)c1ccc2cc3occc(=O)c3cc2c1] 420) |

TABLE 17-continued
| Structure |
|---|
| 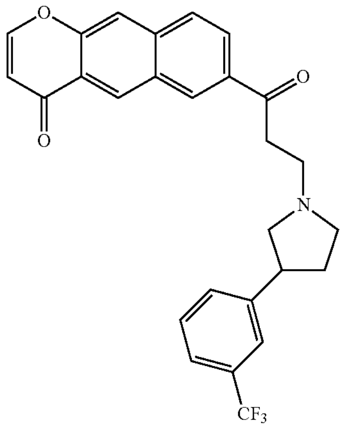 [SMILES: O=C(CCN1CCC(c2cccc(C(F)(F)F)c2)C1)c1ccc2cc3occc(=O)c3cc2c1] 421) |
| 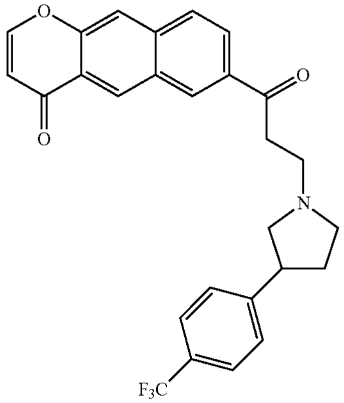 [SMILES: O=C(CCN1CCC(c2ccc(C(F)(F)F)cc2)C1)c1ccc2cc3occc(=O)c3cc2c1] 422) |
| 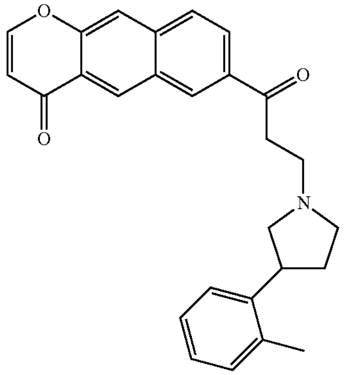 [SMILES: Cc1ccccc1C1CCN(CCC(=O)c2ccc3cc4occc(=O)c4cc3c2)C1] 423) |
TABLE 17-continued
| Structure |
|---|
| 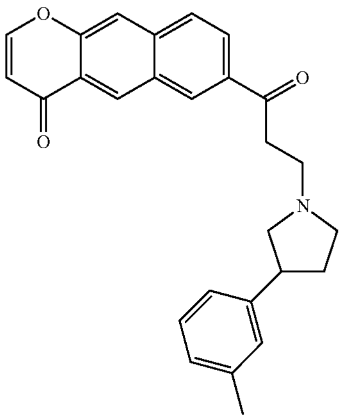 [SMILES: Cc1cccc(C2CCN(CCC(=O)c3ccc4cc5occc(=O)c5cc4c3)C2)c1] 424) |
| 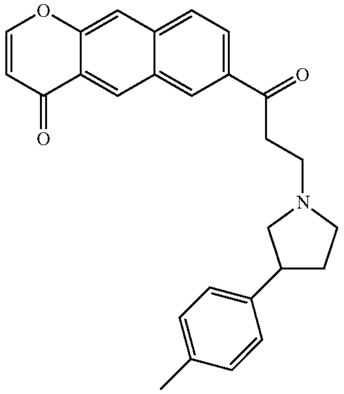 [SMILES: Cc1ccc(C2CCN(CCC(=O)c3ccc4cc5occc(=O)c5cc4c3)C2)cc1] 425) |
| 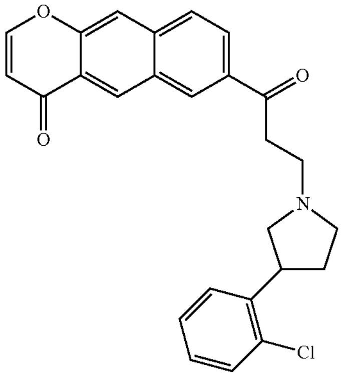 [SMILES: O=C(CCN1CCC(c2ccccc2Cl)C1)c1ccc2cc3occc(=O)c3cc2c1] 426) |
| 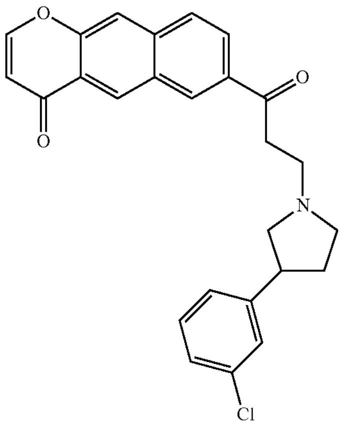 [SMILES: O=C(CCN1CCC(c2cccc(Cl)c2)C1)c1ccc2cc3occc(=O)c3cc2c1] 427) |

TABLE 17-continued
| Structure |
|---|
| 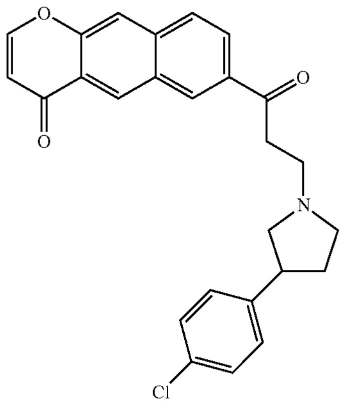 [SMILES: O=C(CCN1CCC(c2ccc(Cl)cc2)C1)c1ccc2cc3occc(=O)c3cc2c1] 428) |
| 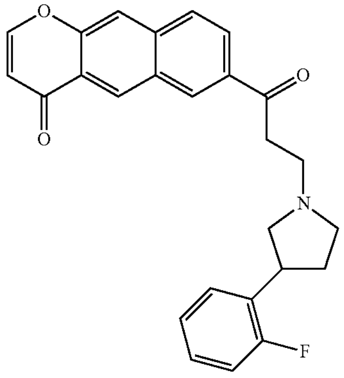 [SMILES: O=C(CCN1CCC(c2ccccc2F)C1)c1ccc2cc3occc(=O)c3cc2c1] 429) |
| 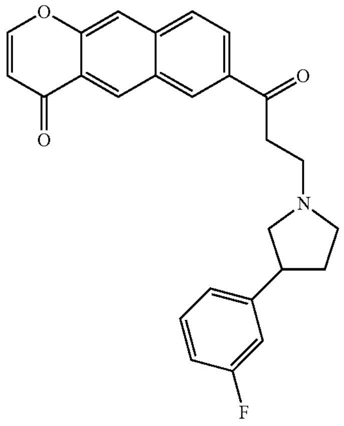 [SMILES: O=C(CCN1CCC(c2cccc(F)c2)C1)c1ccc2cc3occc(=O)c3cc2c1] 430) |
TABLE 17-continued
| Structure |
|---|
| 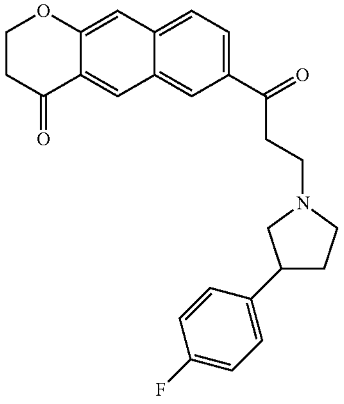 [SMILES: O=C(CCN1CCC(c2ccc(F)cc2)C1)c1ccc2cc3c(cc2c1)C(=O)CCO3] 431) |
| 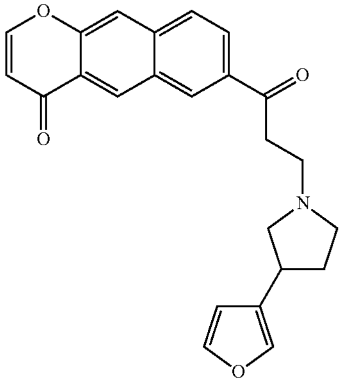 432) |
| 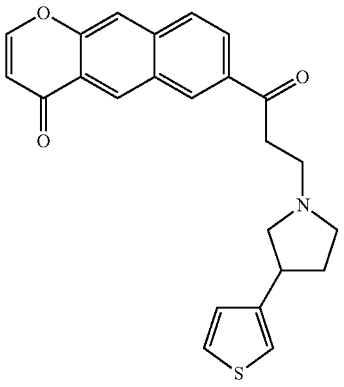 [SMILES: O=C(CCN1CCC(c2ccoc2)C1)c1ccc2cc3occc(=O)c3cc2c1] 433) |
| 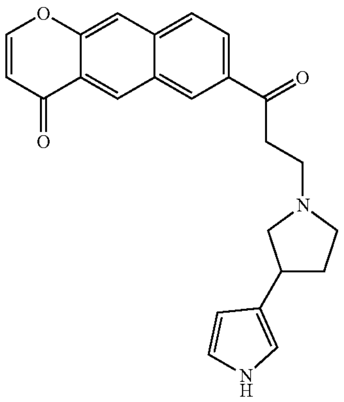 [SMILES: O=C(CCN1CCC(c2cc[nH]c2)C1)c1ccc2cc3occc(=O)c3cc2c1] 434) |

TABLE 17-continued
| Structure | |
|---|---|
| 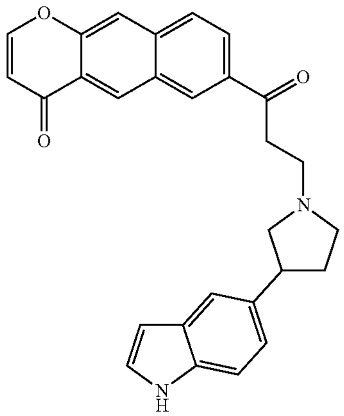 [SMILES: O=C(CCN1CCC(c2ccc3[nH]ccc3c2)C1)c1ccc2cc3occc(=O)c3cc2c1] | 435) |
| 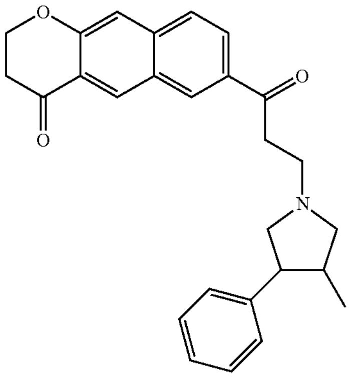 [SMILES: CC1CN(CCC(=O)c2ccc3cc4c(cc3c2)C(=O)CCO4)CC1c1ccccc1] | 436) |
| 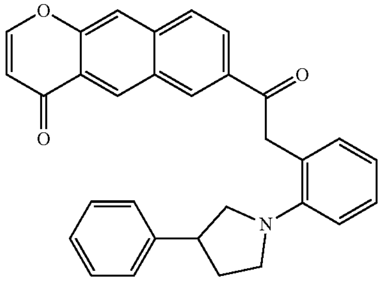 [SMILES: O=C(Cc1ccccc1N1CCC(c2ccccc2)C1)c1ccc2cc3occc(=O)c3cc2c1] | 437) |
TABLE 18
| Structure | |
|---|---|
| 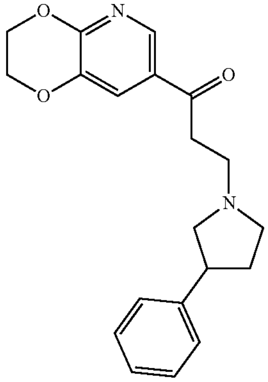 [SMILES: O=C(CCN1CCC(c2ccccc2)C1)c1cnc2c(c1)OCCO2] | 438) |
TABLE 18-continued
| Structure | |
|---|---|
| 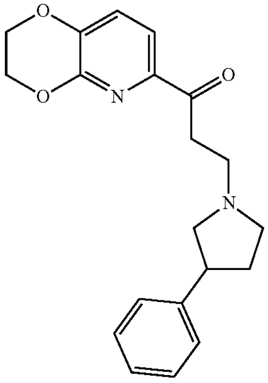 [SMILES: O=C(CCN1CCC(c2ccccc2)C1)c1ccc2c(n1)OCCO2] | 439) |
| 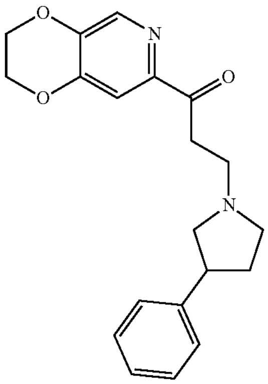 [SMILES: O=C(CCN1CCC(c2ccccc2)C1)c1cc2c(cn1)OCCO2] | 440) |
| 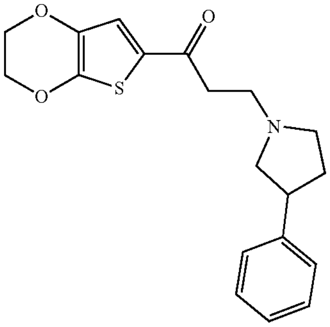 [SMILES: O=C(CCN1CCC(c2ccccc2)C1)c1cc2c(s1)OCCO2] | 441) |
| 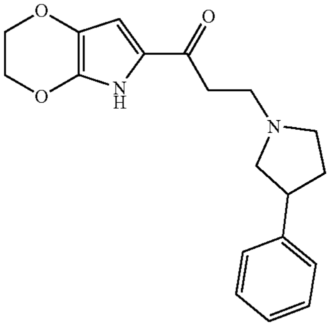 [SMILES: O=C(CCN1CCC(c2ccccc2)C1)c1cc2c([nH]1)OCCO2] | 442) |

TABLE 18-continued
| Structure |
|---|
| 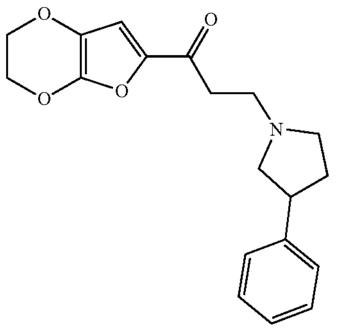 [SMILES: O=C(CCN1CCC(c2ccccc2)C1)c1cc2c(o1)OCCO2] 443) |
| 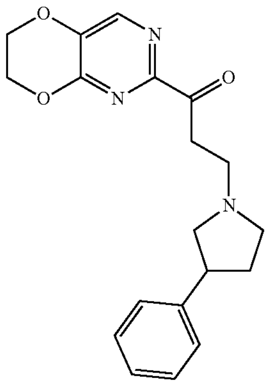 [SMILES: O=C(CCN1CCC(c2ccccc2)C1)c1ncc2c(n1)OCCO2] 444) |
| 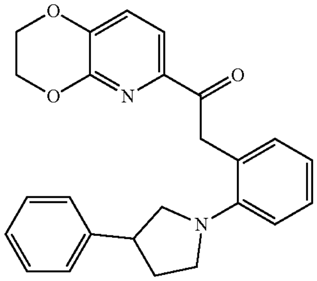 [SMILES: O=C(Cc1ccccc1N1CCC(c2ccccc2)C1)c1ccc2c(n1)OCCO2] 445) |
| 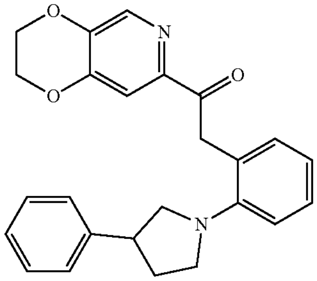 [SMILES: O=C(Cc1ccccc1N1CCC(c2ccccc2)C1)c1cc2c(cn1)OCCO2] 446) |
| 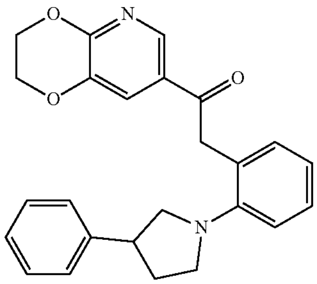 [SMILES: O=C(Cc1ccccc1N1CCC(c2ccccc2)C1)c1cnc2c(c1)OCCO2] 447) |
TABLE 18-continued
| Structure |
|---|
| 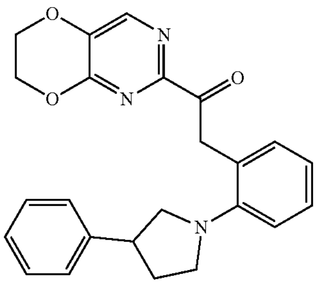 448) |
| 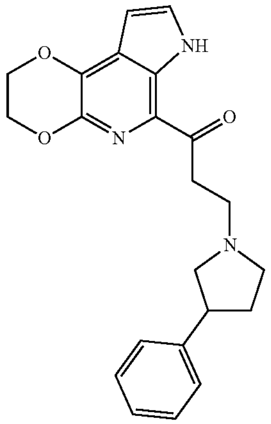 [SMILES: O=C(CCN1CCC(c2ccccc2)C1)c1nc2c(c3cc[nH]c13)OCCO2] 449) |
| 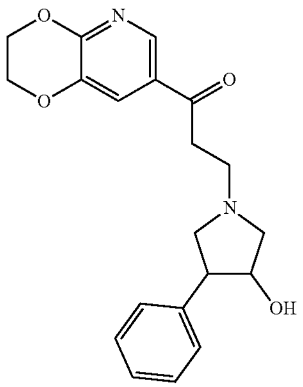 [SMILES: O=C(CCN1CC(O)C(c2ccccc2)C1)c1cnc2c(c1)OCCO2] 450) |
| 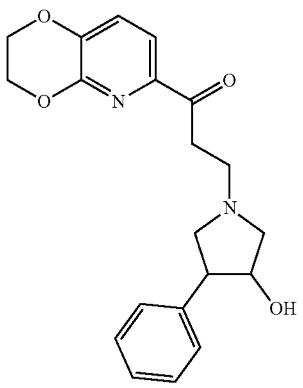 [SMILES: O=C(CCN1CC(O)C(c2ccccc2)C1)c1ccc2c(n1)OCCO2] 451) |

TABLE 18-continued
| Structure |
|---|
| 452) 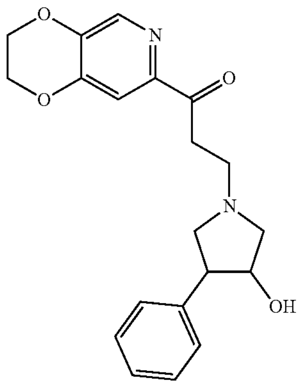 [SMILES: O=C(CCN1CC(O)C(c2ccccc2)C1)c1cc2c(cn1)OCCO2] |
| 453) 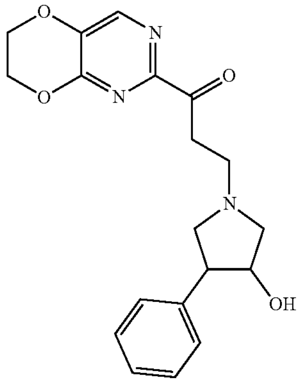 [SMILES: O=C(CCN1CC(O)C(c2ccccc2)C1)c1ncc2c(n1)OCCO2] |
| 454) 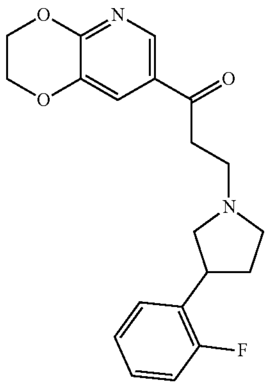 [SMILES: O=C(CCN1CCC(c2ccccc2F)C1)c1cnc2c(c1)OCCO2] |
| 455) 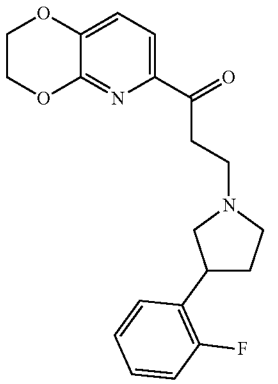 [SMILES: O=C(CCN1CCC(c2ccccc2F)C1)c1ccc2c(n1)OCCO2] |
TABLE 18-continued
| Structure |
|---|
| 456) 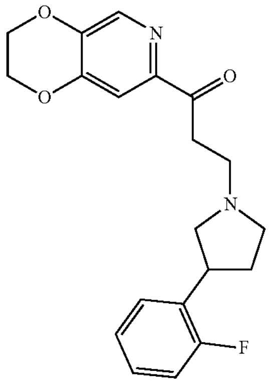 [SMILES: O=C(CCN1CCC(c2ccccc2F)C1)c1cc2c(cn1)OCCO2] |
| 457) 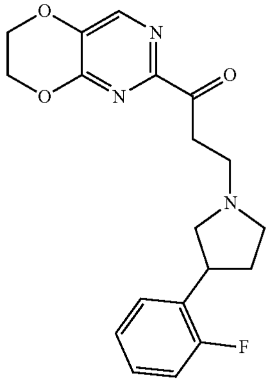 [SMILES: O=C(CCN1CCC(c2ccccc2F)C1)c1ncc2c(n1)OCCO2] |
| 458) 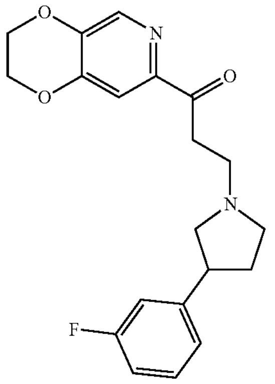 [SMILES: O=C(CCN1CCC(c2cccc(F)c2)C1)c1cc2c(cn1)OCCO2] |
| 459) 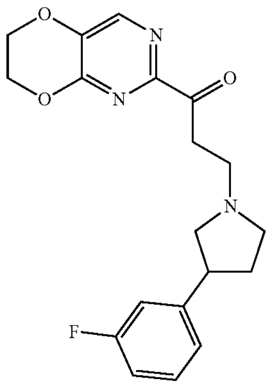 |

TABLE 18-continued
| Structure | |
|---|---|
| 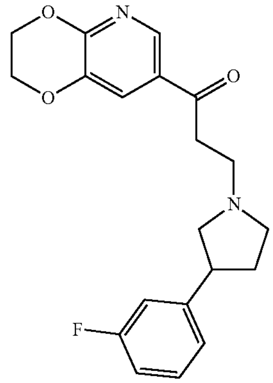 [SMILES: O=C(CCN1CCC(c2cccc(F)c2)C1)c1cnc2c(c1)OCCO2] | 560) |
| 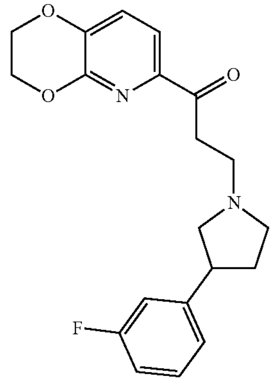 [SMILES: O=C(CCN1CCC(c2cccc(F)c2)C1)c1ccc2c(n1)OCCO2] | 461) |
| 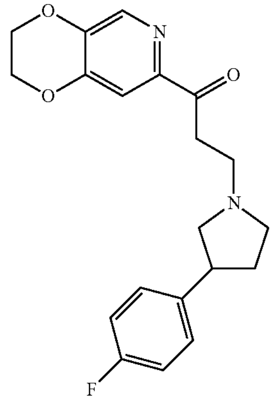 [SMILES: O=C(CCN1CCC(c2ccc(F)cc2)C1)c1cc2c(cn1)OCCO2] | 462) |
| 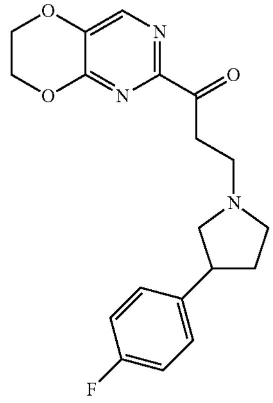 [SMILES: O=C(CCN1CCC(c2ccc(F)cc2)C1)c1ncc2c(n1)OCCO2] | 463) |
TABLE 18-continued
| Structure | |
|---|---|
| 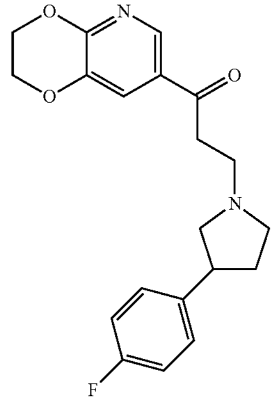 [SMILES: O=C(CCN1CCC(c2ccc(F)cc2)C1)c1cnc2c(c1)OCCO2] | 464) |
| 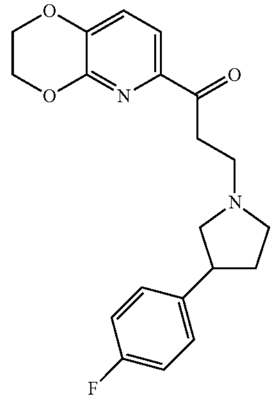 [SMILES: O=C(CCN1CCC(c2ccc(F)cc2)C1)c1ccc2c(n1)OCCO2] | 465) |
TABLE 19
| Structure | |
|---|---|
| 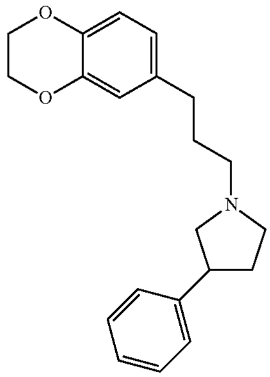 [SMILES: c1ccc(C2CCN(CCCc3ccc4c(c3)OCCO4)C2)cc1] | 466) |

TABLE 19-continued
| Structure |
| --- |
| 467) 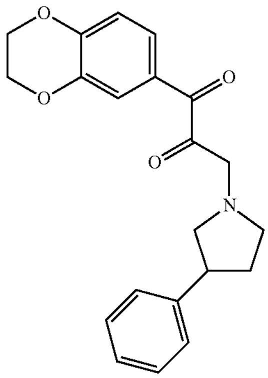 [SMILES: O=C(CN1CCC(c2ccccc2)C1)C(=O)c1ccc2c(c1)OCCO2] |
| 468) 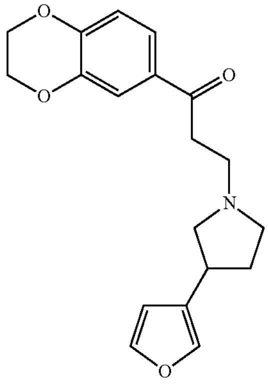 |
| 469) 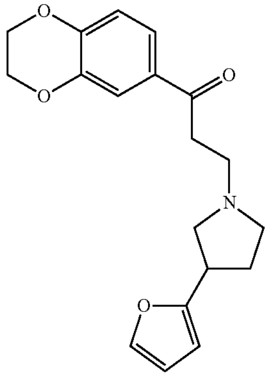 [SMILES: O=C(CCN1CCC(c2ccco2)C1)c1ccc2c(c1)OCCO2] |
| 470) 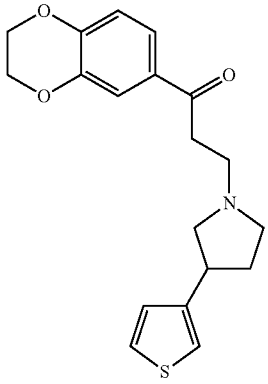 [SMILES: O=C(CCN1CCC(c2ccsc2)C1)c1ccc2c(c1)OCCO2] |
TABLE 19-continued
| Structure |
| --- |
| 471) 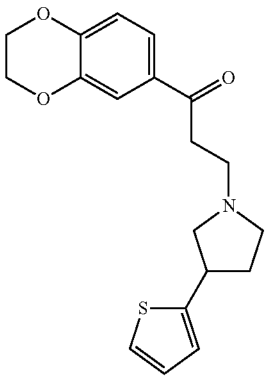 |
| 472) 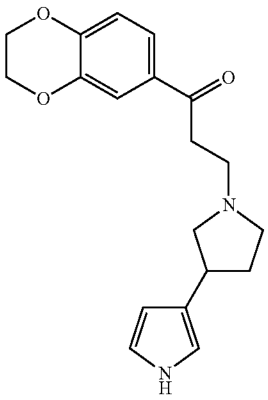 [SMILES: O=C(CCN1CCC(c2cc[nH]c2)C1)c1ccc2c(c1)OCCO2] |
| 473) 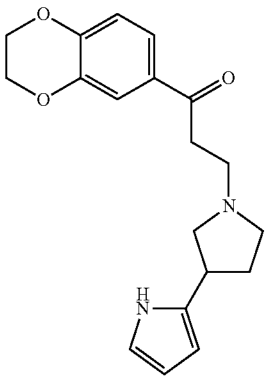 [SMILES: O=C(CCN1CCC(c2ccc[nH]2)C1)c1ccc2c(c1)OCCO2] |
| 474) 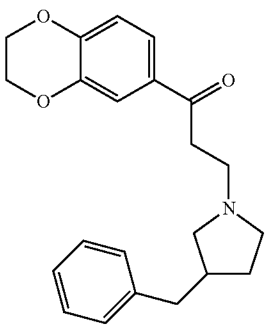 [SMILES: O=C(CCN1CCC(Cc2ccccc2)C1)c1ccc2c(c1)OCCO2] |

TABLE 19-continued
| Structure |
|---|
| 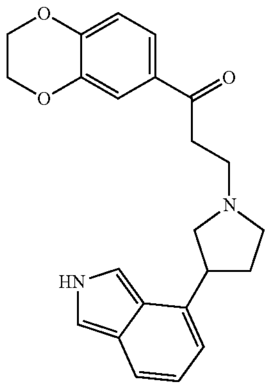 [SMILES: O=C(CCN1CCC(c2cccc3c[nH]cc23)C1)c1ccc2c(c1)OCCO2] 475) |
| 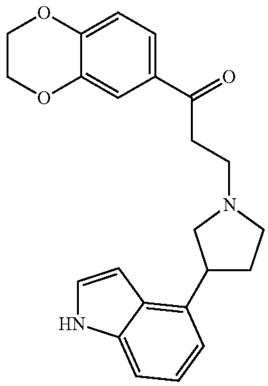 [SMILES: O=C(CCN1CCC(c2cccc3[nH]ccc23)C1)c1ccc2c(c1)OCCO2] 476) |
| 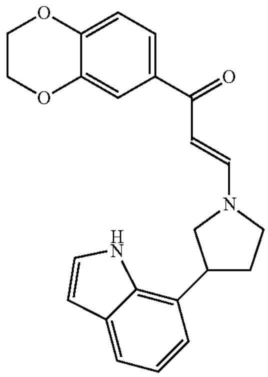 [SMILES: O=C(/C=C/N1CCC(c2cccc3cc[nH]c23)C1)c1ccc2c(c1)OCCO2] 477) |
| 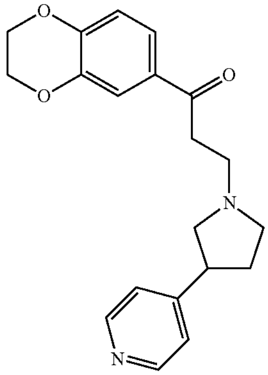 [SMILES: O=C(CCN1CCC(c2ccncc2)C1)c1ccc2c(c1)OCCO2] 478) |
TABLE 19-continued
| Structure |
|---|
| 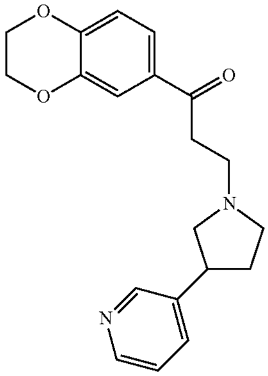 [SMILES: O=C(CCN1CCC(c2cccnc2)C1)c1ccc2c(c1)OCCO2] 479) |
| 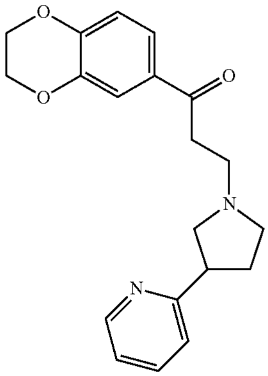 [SMILES: O=C(CCN1CCC(c2ccccn2)C1)c1ccc2c(c1)OCCO2] 480) |
| 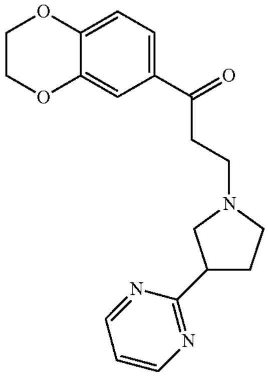 [SMILES: O=C(CCN1CCC(c2ncccn2)C1)c1ccc2c(c1)OCCO2] 481) |
| 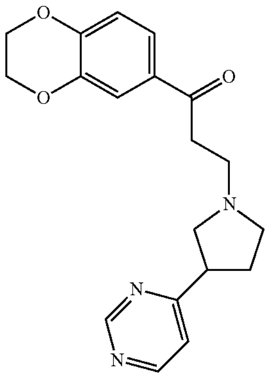 [SMILES: O=C(CCN1CCC(c2ccncn2)C1)c1ccc2c(c1)OCCO2] 482) |

TABLE 19-continued
| Structure | |
|---|---|
| 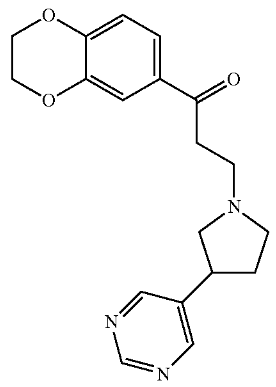 [SMILES: O=C(CCN1CCC(c2cncnc2)C1)c1ccc2c(c1)OCCO2] | 483) |
| 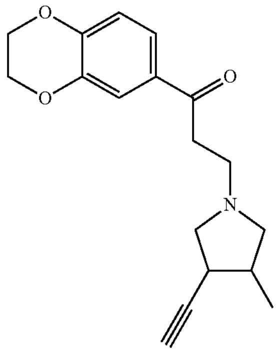 [SMILES: C#CC1CN(CCC(=O)c2ccc3c(c2)OCCO3)CC1C] | 484) |
| 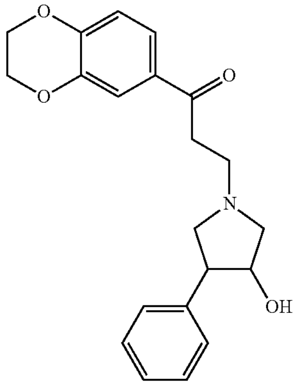 [SMILES: O=C(CCN1CC(O)C(c2ccccc2)C1)c1ccc2c(c1)OCCO2] | 485) |
| 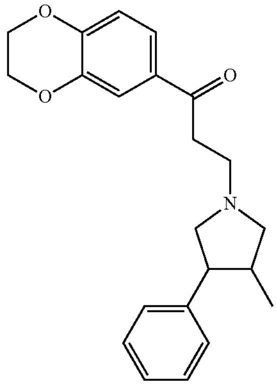 [SMILES: CC1CN(CCC(=O)c2ccc3c(c2)OCCO3)CC1c1ccccc1] | 486) |
TABLE 19-continued
| Structure | |
|---|---|
| 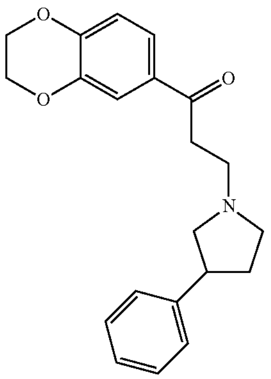 [SMILES: O=C(CCN1CCC(c2ccccc2)C1)c1ccc2c(c1)OCCO2] | 487) |
| 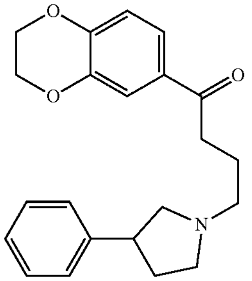 [SMILES: O=C(CCCN1CCC(c2ccccc2)C1)c1ccc2c(c1)OCCO2] | 488) |
| 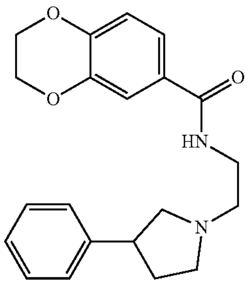 [SMILES: O=C(NCCN1CCC(c2ccccc2)C1)c1ccc2c(c1)OCCO2] | 489) |
| 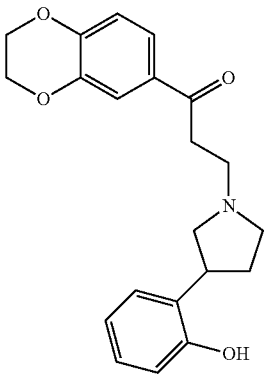 [SMILES: O=C(CCN1CCC(c2ccccc2O)C1)c1ccc2c(c1)OCCO2] | 490) |

TABLE 19-continued
| Structure | |
|---|---|
| 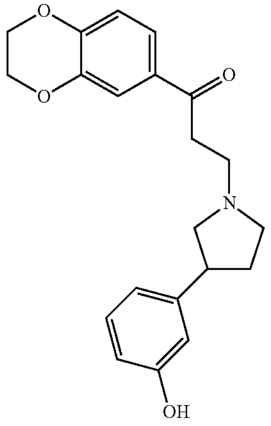 [SMILES: O=C(CCN1CCC(c2cccc(O)c2)C1)c1ccc2c(c1)OCCO2] | 491) |
| 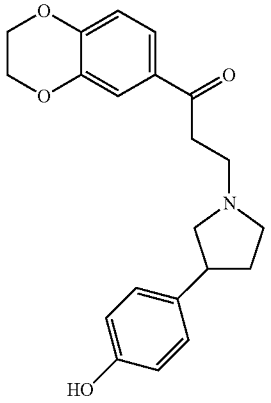 [SMILES: O=C(CCN1CCC(c2ccc(O)cc2)C1)c1ccc2c(c1)OCCO2] | 492) |
| 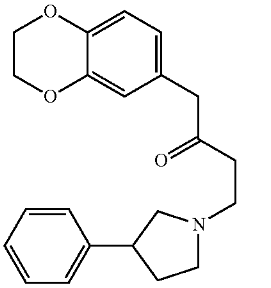 [SMILES: O=C(CCN1CCC(c2ccccc2)C1)Cc1ccc2c(c1)OCCO2] | 493) |
| 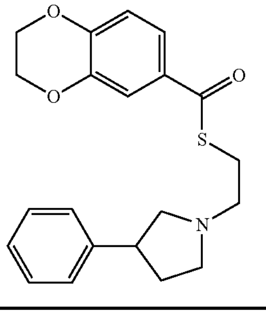 | 494) |
TABLE 20
| Structure | |
|---|---|
| 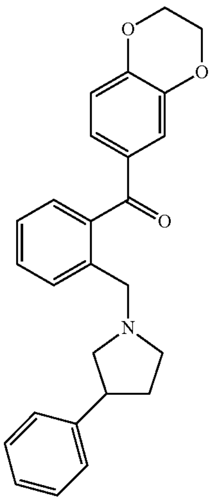 [SMILES: O=C(c1ccc2c(c1)OCCO2)c1ccccc1CN1CCC(c2ccccc2)C1] | 495) |
| 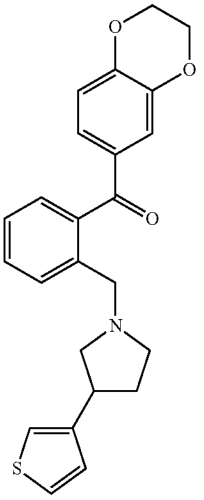 | 496) |
| 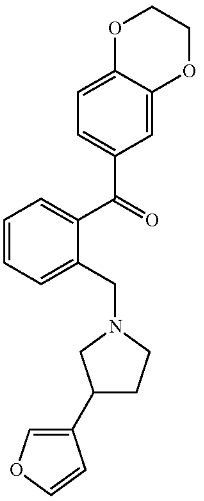 [SMILES: O=C(c1ccc2c(c1)OCCO2)c1ccccc1CN1CCC(c2ccoc2)C1] | 497) |

TABLE 20-continued
| Structure |
| --- |
| 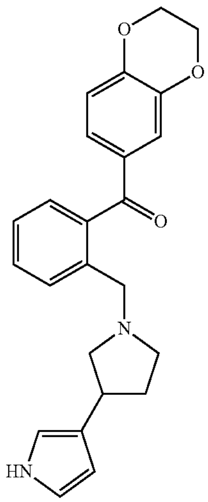 [SMILES: O=C(c1ccc2c(c1)OCCO2)c1ccccc1CN1CCC(c2cc[nH]c2)C1] 498) |
| 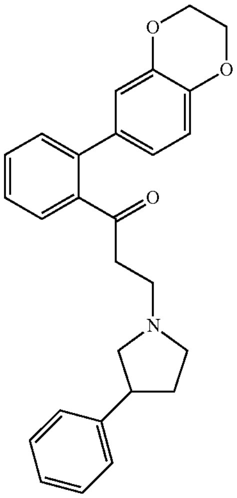 [SMILES: O=C(CCN1CCC(c2ccccc2)C1)c1ccccc1-c1ccc2c(c1)OCCO2] 499) |
| 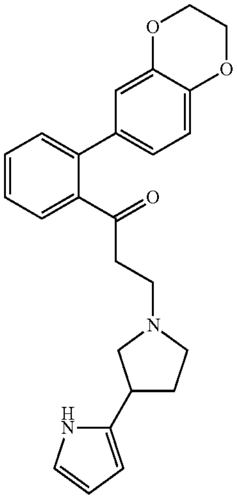 500) |
TABLE 20-continued
| Structure |
| --- |
| 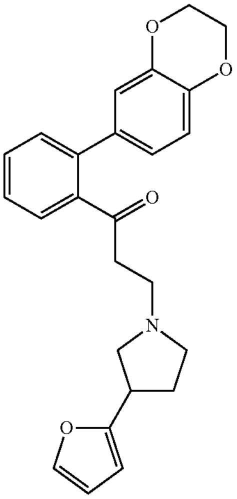 [SMILES: O=C(CCN1CCC(c2ccco2)C1)c1ccccc1-c1ccc2c(c1)OCCO2] 501) |
| 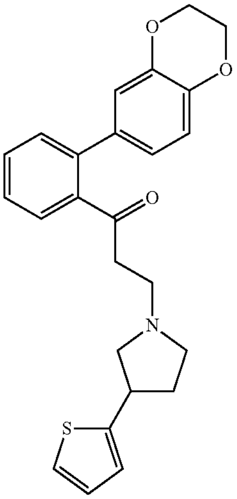 [SMILES: O=C(CCN1CCC(c2cccs2)C1)c1ccccc1-c1ccc2c(c1)OCCO2] 502) |
| 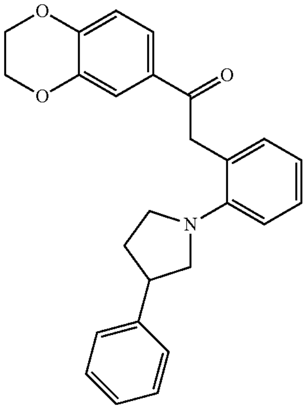 [SMILES: O=C(Cc1ccccc1N1CCC(c2ccccc2)C1)c1ccc2c(c1)OCCO2] 503) |

TABLE 20-continued
| Structure | |
|---|---|
| 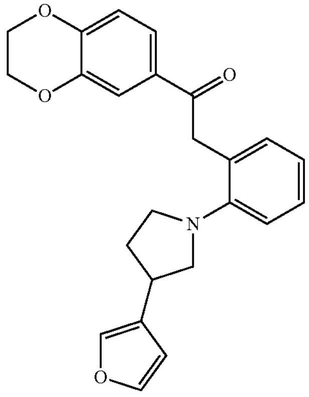 [SMILES: O=C(Cc1ccccc1N1CCC(c2ccoc2)C1)c1ccc2c(c1)OCCO2] | 504) |
| 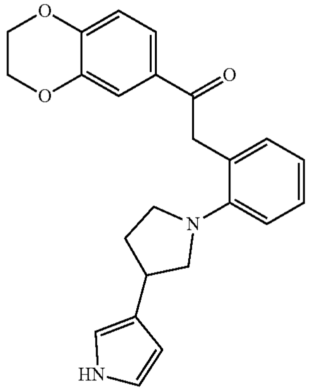 [SMILES: O=C(Cc1ccccc1N1CCC(c2cc[nH]c2)C1)c1ccc2c(c1)OCCO2] | 505) |
| 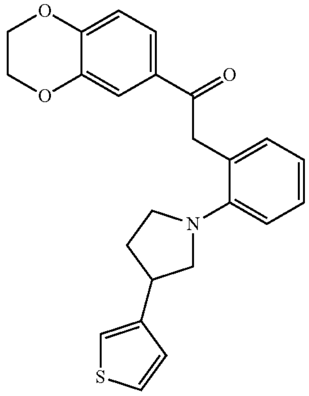 [SMILES: O=C(Cc1ccccc1N1CCC(c2ccsc2)C1)c1ccc2c(c1)OCCO2] | 506) |
| 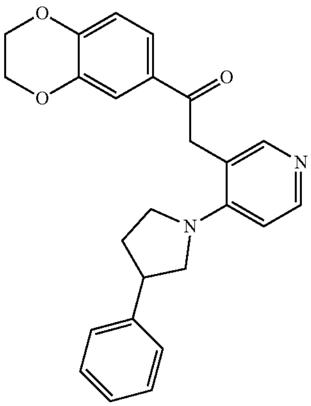 [SMILES: O=C(Cc1cnccc1N1CCC(c2ccccc2)C1)c1ccc2c(c1)OCCO2] | 507) |
TABLE 20-continued
| Structure | |
|---|---|
| 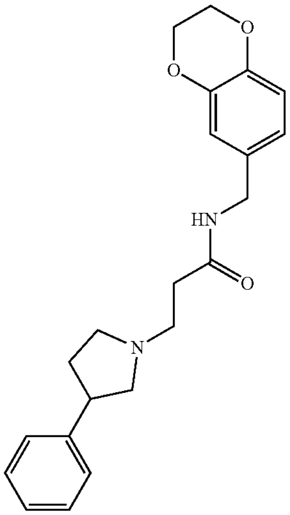 [SMILES: O=C(CCN1CCC(c2ccccc2)C1)NCc1ccc2c(c1)OCCO2] | 508) |
| 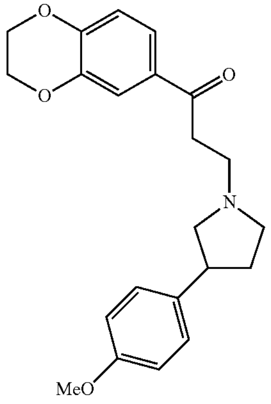 [SMILES: COc1ccc(C2CCN(CCC(=O)c3ccc4c(c3)OCCO4)C2)cc1] | 509) |
| 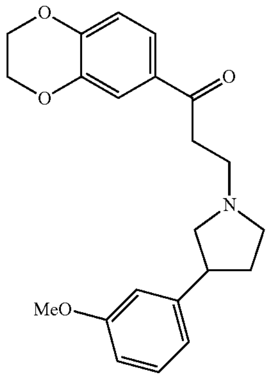 [SMILES: COc1cccc(C2CCN(CCC(=O)c3ccc4c(c3)OCCO4)C2)c1] | 510) |

TABLE 20-continued
| Structure | |
|---|---|
| 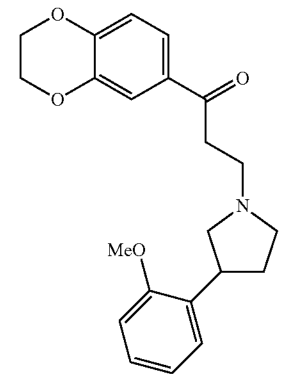 [SMILES: COc1ccccc1C1CCN(CCC(=O)c2ccc3c(c2)OCCO3)C1] | 511) |
| 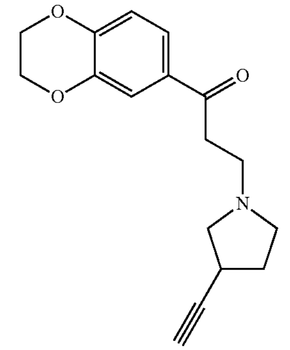 [SMILES: C#CC1CCN(CCC(=O)c2ccc3c(c2)OCCO3)C1] | 512) |
| 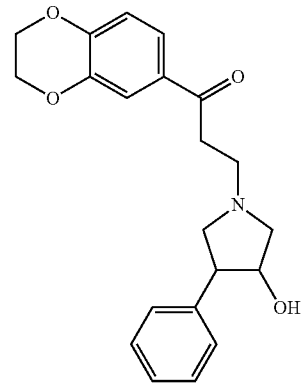 [SMILES: O=C(CCN1CC(O)C(c2ccccc2)C1)c1ccc2c(c1)OCCO2] | 513) |
| 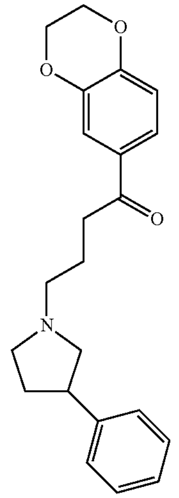 [SMILES: O=C(CCCN1CCC(c2ccccc2)C1)c1ccc2c(c1)OCCO2] | 514) |
TABLE 20-continued
| Structure | |
|---|---|
| 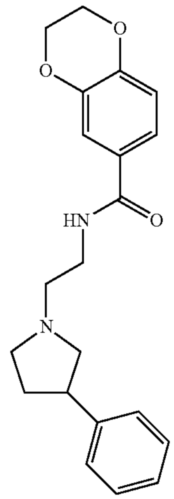 [SMILES: O=C(NCCN1CCC(c2ccccc2)C1)c1ccc2c(c1)OCCO2] | 515) |
| 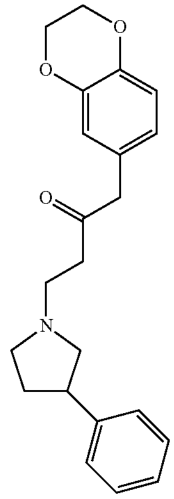 [SMILES: O=C(CCN1CCC(c2ccccc2)C1)Cc1ccc2c(c1)OCCO2] | 516) |
| 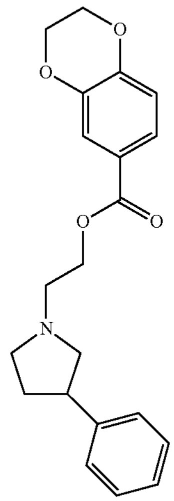 [SMILES: O=C(OCCN1CCC(c2ccccc2)C1)c1ccc2c(c1)OCCO2] | 517) |

TABLE 20-continued

| Structure |
|---|
| 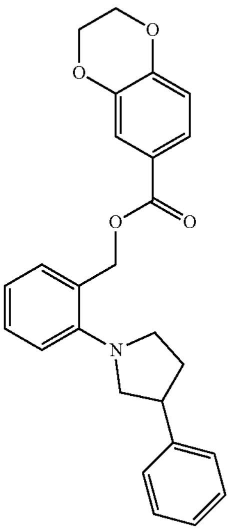 [SMILES: O=C(OCc1ccccc1N1CCC(c2ccccc2)C1)c1ccc2c(c1)OCCO2] 518) |
| 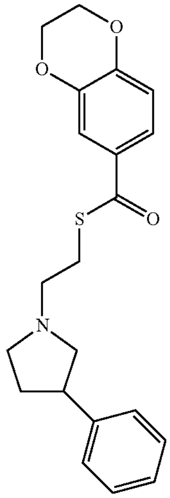 [SMILES: O=C(SCCN1CCC(c2ccccc2)C1)c1ccc2c(c1)OCCO2] 519) |
| 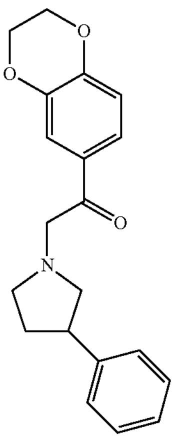 [SMILES: O=C(CN1CCC(c2ccccc2)C1)c1ccc2c(c1)OCCO2] 520) |

TABLE 20-continued

| Structure |
|---|
| 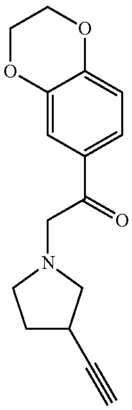 521) |

II. METHODS OF INHIBITION OF GLIAL CELL ACTIVATION

The compounds according to formula 1 and compositions described herein inhibit the activation of glial cells by various types of glial cells present in the nervous systems of mammals including humans. Non-limiting examples are inhibition of activation of glial cells by the compounds according to formula 1 including, but not limited to glial cell such as: Astrocytes, Bergmann glia, Ependymal cells, Oligodendrocytes, Microglia, Müller cells, Radial glia, Satellite cells, and Schwann cells under conditions known to activate glial cells as can be measured by various assays of activation induced biomarkers including increases in RNA levels and protein production. In addition, the decrease of other biomarkers produced by normal non-activated glial cells can be measured and are indicative of glial cell activation and transformation to pathogenic glial cells.

Glia cells in their non-activated or resting state release biologically active factors, such as, but not limited to brain-derived neurotrophic factor (BDNF), glial-derived glutamate (GDNF), glycine, and L-serine; these can affect basal neurotransmission, synaptic plasticity, and neuronal cell viability via direct action on neurons or can act on other non-neuronal cells including other glial cell types. Activated glial cells cease to produce many of the factors noted herein as well as others to induce such things as, but not limited to; neuronal cell dysfunction, loss of synaptic plasticity, abnormal neurotransmission, and cell death. The compounds according to formula 1 of the present invention have been found to inhibit the loss of production by glial cells of factors supporting normal neuronal cells when the glial cells are treated with compounds known to cause glial cell activation.

Glial cells in their activated state are characterized and defined by the production of several biologically active factors, such as but not limited to; C—C motif ligand 2 (CCL2), C—C motif ligand 5 (CCL5), C—X—C motif chemokine ligand 10 (CXCL10), Interleukin 1 beta (IL-1beta), Interleukin 6 (IL-6), Interferon beta-la (INF-Beta), Tumor necrosis factor alpha (TNF-alpha), and Vascular endothelial cell growth factor (VEGF) that can damage other cell types and/or the surrounding tissue. These bio-markers are not produced in any clinically significant level by resting, non-activated glial cells.

The compounds according to formula 1 of the present invention have been found to inhibit activation of glial cells and thus, simultaneously inhibit the production of multiple biomarkers produced by activated glial cells, including but not limited to; CCL2, CCL5, CXCL10, IL-1beta, IL-6, INF-Beta, TNF-alpha, and VEGF while not affecting glial cell viability, or the production of factors associated with normal non-activated glial cells.

III. METHODS OF TREATMENT

The compounds according to formula 1 and compositions described herein have utility in the treatment of disorders associated with glial cell activation in human subjects. Activated glial cells are directly contributory to the pathogenesis of disorders of the central and peripheral nervous systems, such as but not limited to: Acquired Immunodeficiency Syndrome, Alexander disease, Alzheimer Disease, Amyotrophic lateral sclerosis, Attention Deficit Hyperactivity disorder, Autism, Bipolar disorder, Central serous retinopathy, Chronic inflammatory demyelinating polyradiculoneuropathy, Depression, Diabetic macular edema, Diabetic retinopathy, Diabetic neuropathy, Encephalitis, Epilepsy, Fragile X syndrome, Glioblastoma, Gliosis, Guillain-Barre syndrome, Huntington's disease, Hypertensive retinopathy, Lymphocytic Choriomeningitis, Macular Degeneration, Multiple Sclerosis, Myasthenia Gravis, Neuromyelitis Optica spectrum disorder, Parkinson Disease, Polyradiculoneuropathy, Prion diseases, Retinopathy, Retinopathy of Prematurity, Schizophrenia, Spinal muscle atrophy, Spondylitis, or Traumatic brain injury syndrome. In some human subjects the disorders noted herein may co-occur simultaneously or sequentially. Thus, inhibition of glial activation has implications for treatment of many disorders with diverse primary etiologies.

As used in this application, the terms "co-administered" or "co-administration" refer to a dosing regimen where the compound of Formula 1 is administered with a second therapeutic agent and/or adjuvant, typically having a differing mechanism of action, to promote a desired result. It should be understood that "co-administration" is not limited by the route(s) of administration and can refer to simultaneous dosing, dosing at different times during a single day, or even dosing on different days. The compounds of this invention according to Formula 1 can be administered separately or can be combined into a single formulation (i.e. fixed combination) to inhibit glial cell activation and to treat disorders in human associated with glial cell activation.

In an embodiment of the present invention the compounds according to Formula 1 may be used either simultaneously or sequentially in combination with a second compound and/or adjuvant such as, but not limited to, those listed below to inhibit activation of glial cells as we as to treat disorders in humans associated with activation of glial cells.

Non-steroidal anti-inflammatory drugs, such as but not limited to: aspirin, choline salicylate, celecoxib, acetaminophen, diclofenac, flurbiprofen, ibuprofen, indomethacin, ketoprofen, meclofenamate, mefenamic acid, nabumetone, naproxen, piroxicam, rofecoxib, salicylates, sulindac, tolmetin, and valdecoxib.

Immunomodulatory agents, such as but not limited to: peginterferon beta-la, methotrexate, azathioprine, thalidomide, mitoxantrone, cladribin, apremilast, cyclophosphamide, anti-CTLA-4 antibodies, tacrorimus, methotrexate, anti-programmed cell death protein 1 antibodies, teriflunomide, cyclosporine, and hydroxychloroquine.

Antimalarials, such as but not limited to: chloroquine, quinine, amodiaquine, pyrimethamine, proguanil, mefloquine, atovaquone, primaquine, artemisinin, and halofantrine.

Antibiotics, such as but not limited to: sulfonamides, clindamycin, members of the tetracycline family (including minocycline and doxycycline), erythromycin, and dapsone.

Anti-TNF alpha agents, such as but not limited to: infliximab, adalimumab, certolizumab pegol, golimumab, thalidomide, lenalidomide, pomalidomide, and etanercept.

Anti-CD20 agents, such as but not limited to: rituximab, obinutuzumab, Ibritumomab tiuxetan, and tositumomab.

Anti-compliment factor agents, such as but not limited to: avacincaptad pegol.

Anti-diarrhea agents, such as but not limited to: lidamidine, diphenoxylate, loperamide, and quercetin.

Anti-depressants, such as but not limited to: amitriptyline, clomipramine, doxepin nortriptyline, and trimipramine.

Anti-psychotics, such as but not limited to: droperidol, pimozide, chlorpromazine, thiothixene, loxapine, molindone, quetiapine, risperidone, sertindole, and zotepine.

Anti-fungals, such as but not limited to: clotimazole, flucisoconazole, abafungin, micafugin, terbinafine, ciclopirox, and tolnaftate.

Anti-helminthics, such as but not limited to: mebendazole, levamisole, abamectin, and suramine T lymphocyte activation inhibitors, such as but not limited to: voclosporin, peroxynitrite, and dasatinib.

Anti-IL-1 agents, such as but not limited to: anakinra and IL-1Ra.

Glucocorticoids, such as but not limited to: methyl prednisolone, prednisolone, dexamethasone, betamethasone, fluticasone propionate, budesonide, flunisolide, mometasone furoate, triamcinolone acetonide, rofleponide, ciclesonide, and butixocort propionate.

Anti-cytokine/chemokine antibodies, such as but not limited to: basiliximab, daclizumab, ranibizumab, bevacizumab and secukinumab.

Anti-cytokine/chemokine/nucleic acid or peptide aptamers, such as but not limited to: pegaptanib sodium.

Sex steroids and receptor modulators, such as but not limited to: progesterone, progestins, androgen, estrogen, mifepristone, and misoprostol.

Anti-cellular surface receptor antibodies directed against cell surface receptors such as but not limited: CCR1, CCR3, CCL3L1, CCL4, CCR5, CX3CR1, IL7Ra, and TSLPR.

Anti-cellular surface receptor nucleic acid or peptide aptamers directed against cell surface receptors such as but not limited: CCR1, CCR3, CCL3L1, CCL4, CX3CL1, CCR5, IL7Ra, and TSLPR.

Aminosalicylic acid derivatives such as but not limited to: sulfasalazine and mesalazine.

Anticholinergic agents, such as but not limited to: ipratropium, oxitropium, tiotropium, dextromethorphan, revatropate, pirenzepine, darifenacin, oxybutynin, mecamylamine, terodiline, tolterodine, otilonium, trospium chloride, and solifenacin.

Adrenergic agonists, such as but not limited to: salmeterol, salbutamol, clonidine, oxymetazoline, and dolbutamine.

Cholineric agonists, such as but not limited to: carbachol, epibatidine, galantamine, nicotine, and varenicline, Corticosteroids, such as but not limited to: cortisone and hydrocortisone.

Antineoplastic chemotherapeutic agents, such as but not limited to: cisplatin cyclophosphamide, bleomycin, doxorubicin, etoposide, folinic acid, and vincristine.

Phosphodiesterase inhibitors, such as but not limited to: mesembrenone, rolipram, Ibudilast, piclamilast, luteolin, drotaverine, roflumilast, cilomilast, apremilast, and crisaborole.

Leukotriene pathway modulators, such as but not limited to: 3-[3-butylsulfanyl-1-[(4-chlorophenyl)methyl]-5-propan-2-yl-indol-2-yl]-2,2-dimethyl-propanoic acid, baicalein, caffeic acid, curcumin, hyperforin, and zileuton.

Monoclonal antibodies directed against human immunoglobulins, such as but not limited to: omalizumab.

Adrenergic antagonists, such as but not limited to: alfluosin, idazoxan, labetalol, phentolamine, trazadone, propranolol, and atenolol.

Calcium channel antagonists, such as but not limited to: amelodipine, nifedapine, verapamil, diltiazem, and mibefradil.

Dopamine agonists, such as but not limited to: aripiprazole, bromocriptine, bupropion, cabergoline, lisuride, apomorphine, and roxindole.

Serotonin agonists, such as but not limited to: cabergoline, cisapride, gepirone, lorcaserin, tryptamines, psilocybin, and naratriptan.

Dopamine antagonists, such as but not limited to: amoxipine, bromopride, butaclamol, eticlopride, olanzapine, tiapride, and ziprasidone.

Serotonin antagonists, such as but not limited to: cyproheptadine, ketanserin, metergoline, methdilazine, oxetorone, and tropisetron.

Monoamine reuptake inhibitors, such as but limited to: amineptine, amphetamine, citalopram, edivoxetine, hyperforin, mazindol, mescaline, and viloxazine.

Protease inhibitors, such as but not limited to: amastatin, bestatin, and gabexate.

Histamine receptor antagonists, such as but not limited to: acrivastine, brompheniramine, cetirizine, cimetidine, ciproxifan, clobenprobit, cyclizine, carebastine, cyproheptadine, ebastine, epinastine, efletirizine, fexofenadine, and thioperamide.

Proton pump inhibitors, such as but not limited to; omeprazole, lansoprazole, pantoprazole, and rabeprazole.

HMG-COA reductase inhibitors, such as but not limited to: atorvastatin, fluastatin, lovastatin, and simvastatin.

Retinoids such as, but not limited to, etretinate, tretinoin, retinol, retinyl palmitate, adapalene, tazarotene, and alitretinoin.

Histone deacetylase inhibitors, such as but not limited to; benzamides, hydroxamates, phenylbutyrate, valproic acid, vorinostat, belinostat, resminostat, abexinostat, givinostat, and romidespin.

Janus kinase/signal transducer and activator of transcription (JAK/STAT) inhibitors, such as but not limited to; tofacitinib, abrocitinib, baricitinib, fedratinib, momelotinib, and ruxolitinib.

Cannabinoids, such as but not limited to; tetrahydrocannabinol, cannabidiol, dronabinol, and nabilone.

Angiotensin antagonists, such as not limited to; azilsartan, candesartan, losartan, and telmisartan.

Anti-hyperlipidemics, such as but not limited to; atorvastatin, simvastatin, alirocumab, gemfibrozil, fenofibric acid, nicotinic acid, niacin, omega-3 fatty acids, fatty acid esters, and bempedoic acid.

Anti-hyperglycemic agents such as but limited to; insulin, metformin, glyburide, ciglitazone, pioglitazone, englitazone, tesaglitazar, saroglitazar, bexagliflоxin, canagliflozin, and dapagliflozin.

Weight loss agents, such as but not limited to; tirzepatide, semaglutide, naltrexone, orlistat, topiramate, and mazindol.

Anti-parkinsonism medications, such as but not limited to; apomorphine, levodopa, carbidopa, amantadine, benztropine, safinamide, selegiline, rasagiline, entacapone, and tolcapone.

Monoamine oxidase inhibitors, such as but not limited to; hydrazine, moclobemide, pirlindole, safinamide and bifemelane.

Neurosteroids, such as but not limited to; brexanolone, ganaxolone, posovolone, dehydroepiandrosterone, and anicequol.

Pattern recognition receptor antagonists and inhibitors, such as but not limited to; chloroquine, hydroxychloroquine, evolocumab, poseltinib, carbenoxolone and fosfenopril.

Purinergic receptor antagonists and inhibitors, such as but not limited to; enprofylline, suramin, elinogrel, ivermectin, allopurinol, ticlopidine, clopidogrel and diquafosol.

Administration of the therapeutic agent may be by any suitable means. In some embodiments, the one or more therapeutic agents are administered by oral administration. In some embodiments, the one or more therapeutic agents are administered by transdermal administration. In some embodiments, the one or more therapeutic agents are administered by injection or intravenous infusion. In one embodiment, the one or more therapeutic agents are administered topically to an epithelial, epidermal tissue such as, but not limited to; ocular epithelium, nasal epithelium, epithelium of the oral cavity, or epidermis.

If combinations of agents are administered as separate compositions, they may be administered by the same route or by different routes. If combinations of agents are administered in a single composition, are administered by any suitable route. In some embodiments, combinations of agents are administered as a single composition by routes such as but not limited to; oral administration, intravenous administration or transmucosal administration. In some embodiments, combinations of agents are administered as a single composition by transdermal administration. In some embodiments, the combinations of agent are administered as a single composition by injection directly into the nervous system. In some embodiments, the combinations of agent are administered as a single composition in combination with other pharmacological compounds or biologic agents.

In one embodiment of the present invention the compounds of Formula 1 may formulated with or without non-pharmacologically active excipients such as but not limited to; stabilizers, bulking agents, wetting agents, solubilizers, penetration enhancers, wetting agents, binding agents, flavoring agents, taste masking agents, agents that control drug release from the specific dosage form, or agents that promote immediate release or the compounds of Formula 1 and the like, into various dosage forms well known to those skilled in the art, such as but limited to; dosage forms for tablets, mini tablets, capsules, granules, powders, gels, caplets, troches, sachets, cachets, pouches, gums, sprinkles, liquid solutions, suspensions, and buccal and gastro-retentive preparations. The tablets may be osmotic tablets, matrix tablets, bi- and multilayer tablets, fast disintegrating tablets, or other types of dose forms known to those skilled in the art.

In one embodiment of the present invention the compounds of Formula 1 may formulated with or without non-pharmacologically active excipients into micro-sized or nano-sized macromolecular structures that may improve the pharmacologic characteristics of the medicament such as but not limited to; biological activity, solubility, stability, tissue distribution or cell-type specificity.

In one embodiment of the present invention the compounds of Formula 1 may contain asymmetric or chiral centers and, therefore, exist in different stereoisomeric forms. For example, 7-[3-(3-phenylpyrrolidin-1-yl)butanoyl]chroman-4-one, is a compound according to Formula 1 that possesses two chiral centers at carbon atom number 14 and 20 and thus has four stereoisomer forms. It is intended that all stereoisomeric forms of the compounds of Formula 1 form part of the present invention, including but not limited to: diastereomers, enantiomers, and atropisomers as well as mixtures thereof, such as racemic mixtures. In addition, the present invention embraces all geometric and positional isomers. For example, if a compound of Formula 1 incorporates a double bond or a fused ring, both the cis- and trans-forms, as well as mixtures, are embraced within the scope of the invention. Both the single positional isomers and mixture of positional isomers are also within the scope of the present invention.

In one embodiment of the present invention, compounds of Formula 1 may exist in different tautomeric forms, and all such forms are embraced within the scope of the invention, as defined by the claims.

The dose and dosing regimens of the compound of Formula 1 present in the invention may be adjusted to provide the optimum desired response in accordance with methods and practices well known in the therapeutic arts. For example, a single bolus dose may be administered, or several divided doses may be administered over time. The dose may also be proportionally reduced or increased as indicated by the exigencies of the therapeutic situation. The appropriate dosing regimen, the amount of each dose administered and/or the intervals between doses will depend upon a number of factors, including: the compound, the type of pharmaceutical composition, the characteristics of the subject in need of treatment and the severity of the condition being treated. Adjustment of dosing regimens is commonly used and well known to those skilled in the art.

The dose of the compounds will vary, but as a general guideline for administration, the compounds of Formula 1 will be present in a therapeutically acceptable formulation in a therapeutically effective dose in an amount of from about 0.001 mg/kg to about 1000 mg/kg/body weight per day of a compound provided herein. The pharmaceutical compositions therefore should provide a dosage of from about 0.001 mg/kg/body weight to about 1000 mg/kg/body weight of the compound for some conditions. In another embodiment of the present invention the pharmaceutical dosage unit forms are prepared to provide a preparation for topical application containing 0.001 to 80 w/w %, and more typically from about 0.1 to 10 w/w %. In yet other embodiments the pharmaceutical dosage unit forms are prepared to provide a preparation for injectable application containing from 0.01% to 90% (w/v) of the compounds. The exact dose as a function of factors such as but not limited to; subject's body weight, specific condition being treated, route of administration and subjects physiologic state are well known to those skilled in the art therapeutics and can be determined therein by those skilled in the art.

The skilled artisan can also be expected to readily determine the maximum tolerable dose, the therapeutically effective amount which provides a detectable therapeutic benefit to a patient, and the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

In another embodiment, the medicinal formulations containing the compounds of Formula 1 and any additional therapeutic agents may be administered to a human subject or mammalian species in need on a continuous or intermittent basis. Non-limiting examples include; hourly, daily, or monthly or less frequent; injections, infusions, oral ingestion, and topical applications to various areas of the subject's body. For some subjects in need the compounds of Formula 1 can be continuously administered to achieve the therapeutic effect. The skilled artisan can also be expected to readily determine the route, frequency, and site of administration to achieve the therapeutic effect.

In another embodiment, the medicinal formulations containing the compounds of Formula 1 and any additional therapeutic agents will typically be packaged for retail distribution (i.e. an article of manufacture or a kit). Such articles will be labeled and packaged in a manner to instruct the patient how to use the product. Such instructions will include the condition to be treated, duration of treatment, dosing schedule, etc. The compounds of Formula 1 may also be admixed with any inert carrier and utilized in laboratory assays in order determine the concentration of the compounds within the serum, urine, etc., of the patient as is known in the art. The compounds of Formula 1 may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention belongs. The following examples and biological data are being presented in order to further illustrate the invention. This disclosure should not be construed as limiting the invention in any manner.

For all of the foregoing embodiments, each embodiment disclosed herein is contemplated as being applicable to each of the other disclosed embodiments. Those skilled in the art will readily appreciate that the specific Experimental Details which follow are only illustrative of the invention as described more fully in the claims which follow thereafter.

IV. EXAMPLES

Example 1 Inhibition of Microglia Cell Activation

Figure 1B:
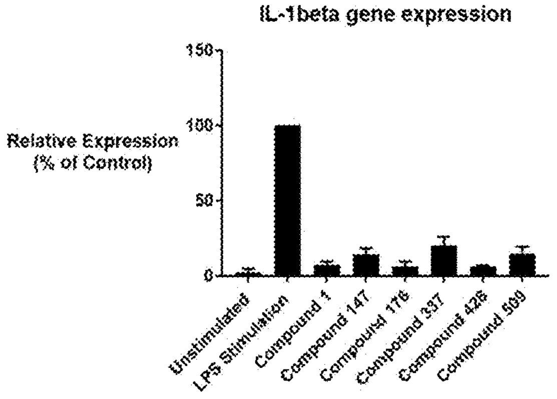
Figure 1C:
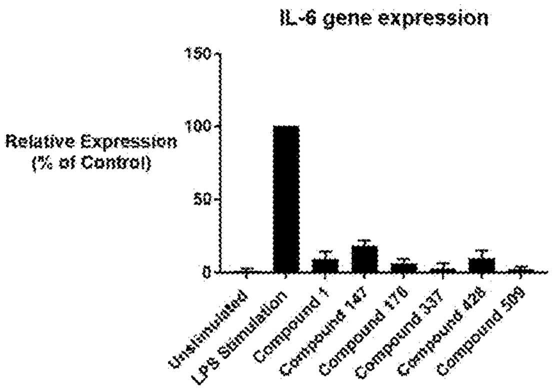
Figure 1D:
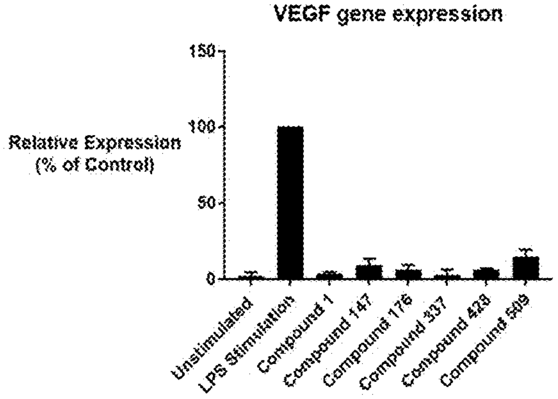
Figure 1E:
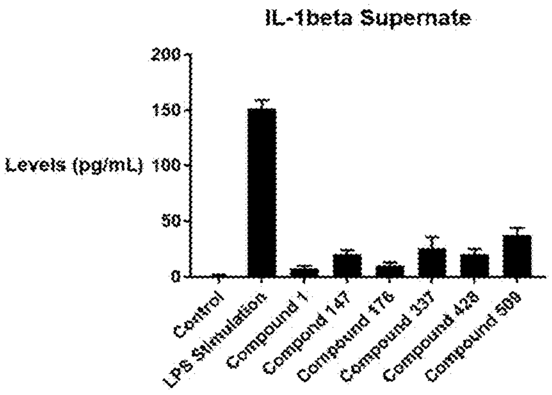
Figure 1F:
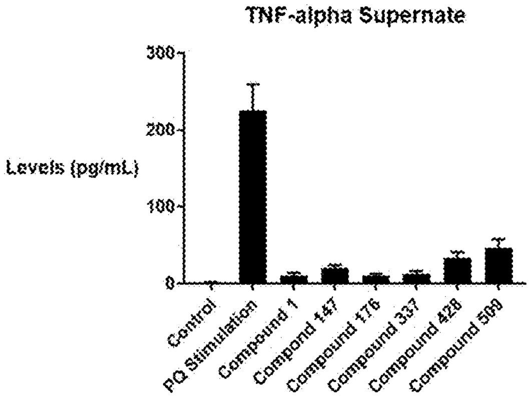

To determine the ability of compounds according to Formula 1 to inhibit microglia cell activation, cultivated human HMC3 microglia cells were used to analyze compounds according to Formula 1 for their ability to inhibit activation in the presence of known glial cell activators after pre-incubation for 24 hrs., with the compounds (10 μM) according to Formula 1 for 24 hrs. Cells were cultured in minimum essential medium (MEM) supplemented with 100 IU/ml penicillin, 10 μg/ml streptomycin, and 10% fetal bovine serum (FBS) (Thermo-Fisher Scientific, Waltham, MA, USA) and were maintained in a humidified incubator at 37° C. with 95% air/5% CO2. To induce activation the cells were treated with lipopolysaccharide (LPS) at 100 ng/mL in culture media or paraquat dichloride hydrate (PQ) at 40 uM (Sigma-Aldrich, St Louis MO) in culture media for 24 hours. Negative controls were untreated cells and positive controls were cells treated with activation inducers but without pre-treatment with compounds according to Formula 1. Measurement of gene expression was determined from total RNA extracted from cell pellets after incubation by RNAseq relative quantitation method standardized using expression of housekeeping genes (GAPDH) as reference standard. Protein production was measured in the cell culture supernatants after incubation using ELISA kits (R&D Systems, Minneapolis, MN). Activation biomarkers measured were CCL2, IL-1beta, IL-6, TNF-alpha and VEGF. The viability of HCM3 cells during treatment was measured by the standard MTT assay. Compounds according to Formula 1 tested had no effect on cell viability at concentration of; 0.1 uM, 1 uM, or 10 uM. Examples of the results of these experiments are seen in FIG. 1 and demonstrate that compounds according to formula 1, inhibited the activation of microglia as determined by inhibition of the production of bio-markers associated with glial cell activation and preserved glial cell viability and normal non-activated microglial cell characteristics.

Example 2 Inhibition of Astrocyte Cell Activation

Figure 2A:
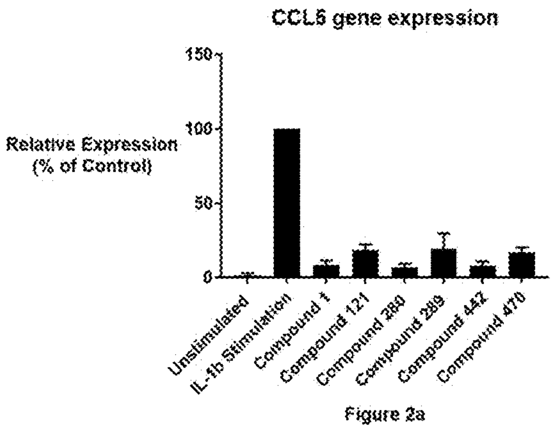
FIGS. 2*a-e*: Biomarkers induced by activation of cultivated human astrocyte cells exposure to a known astrocyte activator after pre-treatment with compounds of Formula 1. Cells were stimulated with recombinant interleukin 1 beta (IL-1b) at 10 ng/ml in culture media and the relative gene expression of; CCL5, CXL10, INF-beta, and TNF-alpha (FIG. 2*a-d*) and corresponding induced production and secretion of and TNF-alpha, (FIG. 2*e*) were measured relative to control human astrocyte cells not treated with the compounds of Formula 1 prior to induction of activation. Human astrocyte cells not induced to activation by IL-1b (unstimulated) were normal controls. The compounds of Formula 1 simultaneously inhibited the production and/or release of these biomarkers, while not affecting astrocyte viability.
Figure 2B:
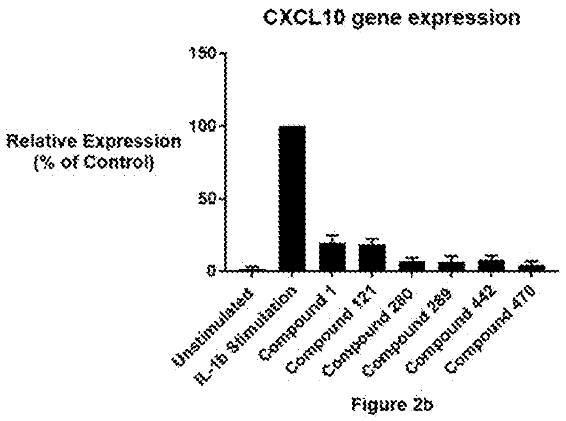
Figure 2C:
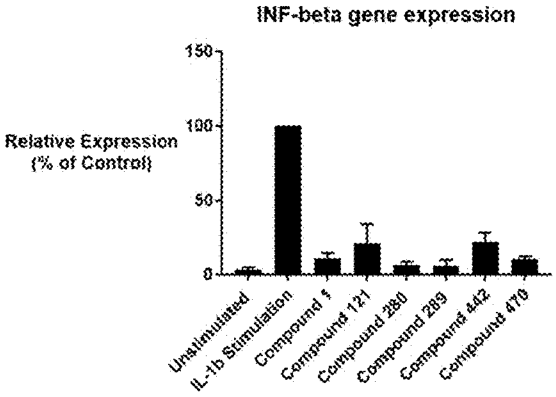
Figure 2D:
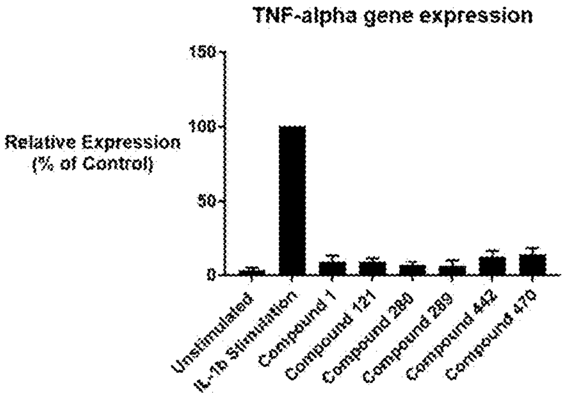
Figure 2E:
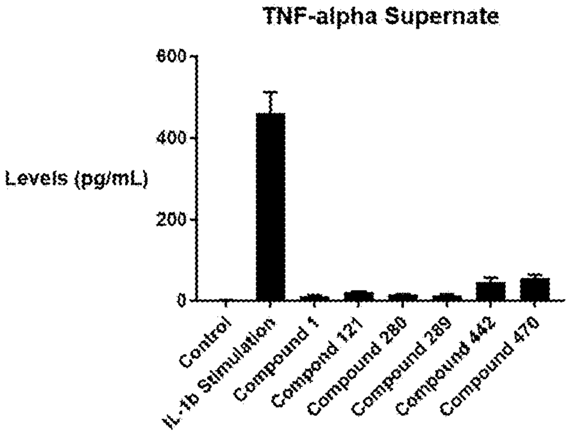

To determine the ability of compounds according to Formula 1 to inhibit astrocyte cell activation, cultivated human astrocyte cells (ixCells, San Diego, CA) were used to analyze compounds according to Formula 1 for their ability to inhibit activation in the presence of known astrocyte cell activators after pre-incubation for 24 hrs., with the compounds (10 μM) according to Formula 1 for 24 hrs. The cells were cultured in Astrocyte Medium supplemented with fetal bovine serum, growth factors without antibiotic (ixCells, San Deigo, CA) and maintained in a humidified incubator at 37° C. with 95% air/5% CO2. To induce activation cells were treated with recombinant IL-1beta in culture media for 18 hours. Negative controls were untreated cells and positive controls were cells treated with activation inducers but without pre-treatment with compounds according to Formula 1. Measurement of gene expression was determined from total RNA extracted from cell pellets after incubation by RNAseq relative quantitation method standardized using expression of housekeeping genes (GAPDH) as reference standard. Protein production was measured in the cell culture supernatants after incubation using ELISA kits (R&D Systems, Minneapolis, MN). Activation biomarkers measured were CCL5, CXCL10, INF-Beta and TNF-alpha. The viability of astrocyte cells during treatment was measured by the standard MTT assay. Compounds according to Formula 1 tested had no effect on cell viability at concentration of; 0.1 uM, 1 uM, or 10 uM. Examples of the results of these experiments are seen in FIG. 2 and demonstrate that compounds according to formula 1, inhibited the activation of astrocyte cells as determined by inhibition of the production of bio-markers associated with astrocyte cell activation and preserved astrocyte cell viability and normal non-activated astrocyte cell characteristics.

Example 3 Inhibition of Muller Cell Activation

Figure 3A:
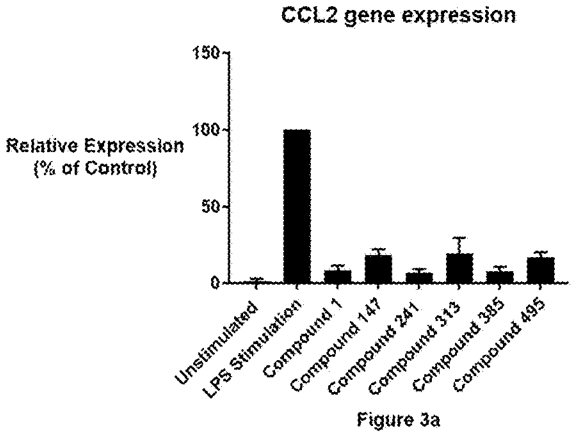
FIG. 3*a-d*: Biomarkers induced by activation of cultivated human retinal Müller cell line MIO-M1 by exposure to a known Muller cell activator after pre-treatment with compounds of Formula 1. Cells were stimulated with lipopolysaccharide (LPS) at 100 ng/mL in culture media and the relative gene expression of CCL2, IL-6 and TNF-alpha were measured (FIG. 3*a-c*) and the corresponding induced production and secretion of TNF-alpha (FIG. 3*d*) was measured relative to control MIO-M1 cells not treated with the compounds of Formula 1 prior to induction. MIO-M1 cells not induced to activation by LPS were (unstimulated) normal controls. The compounds of Formula 1 simultaneously inhibited the production and/or release of these biomarkers, while not affecting MIO-M1 cell viability.
Figure 3B:
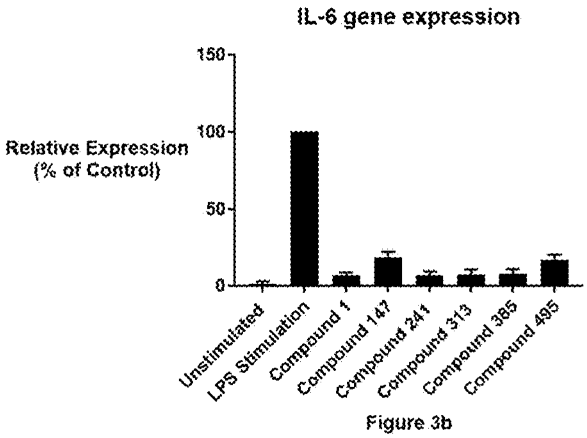
Figure 3C:
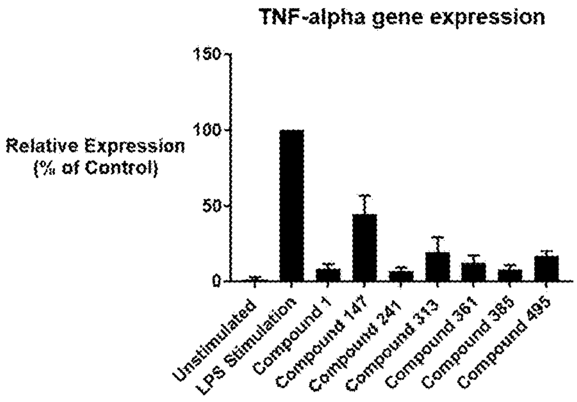
Figure 3D:
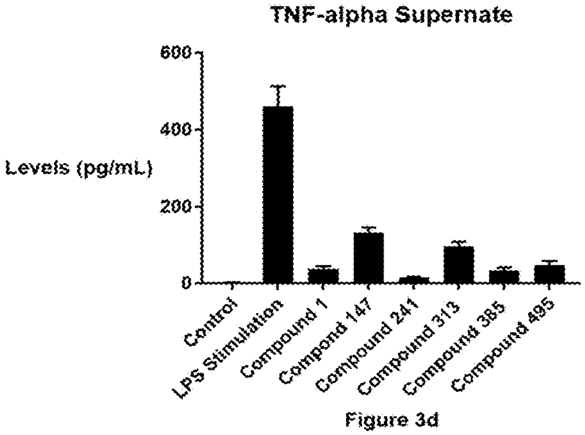

To determine the ability of compounds according to Formula 1 to inhibit Muller cell activation, MIO-M1, a human Müller glial cell line, was grown in Gluta-MAX DMEM medium supplemented with 50 U/mL penicillin, 50 g/mL streptomycin and 10% fetal bovine serum. The MIO-M1 cells were maintained at a temperature of 37° C., at 5% CO2 in a humidified incubator until the cells reached 80% confluency. To test compounds according to formula 1 for inhibition of Muller cell activation the cells were treated with the compounds (10 μM) for 24 hrs., prior to treatment with the glial cell activator; lipopolysaccharide (LPS) at 100 ng/mL. Negative controls were untreated cells and positive controls were cells treated with activation inducers but without pre-treatment with compounds according to Formula 1. Measurement of gene expression was determined from total RNA extracted from cell pellets after incubation by RNAseq relative quantitation method standardized using expression of housekeeping genes (GAPDH) as reference standard. Protein production was measured in the cell culture supernatants after incubation using ELISA kits (R&D Systems, Minneapolis, MN). The biomarkers used to verify the induction of Müller activation were CCL2, IL-6 and TNF-alpha. The viability of MIO-M1 cells during treatment was measured by the standard MTT assay. Compounds according to Formula 1 tested had no effect on cell viability at concentration of; 0.1 uM, 1 uM, or 10 uM. Examples of the results of these experiments are seen in FIG. 3 and demonstrate that compounds according to formula 1, inhibited the activation of MIO-M1 cells as determined by inhibition of the production of bio-markers associated with Muller cell activation and preserved MIO-M1 cell viability and normal non-activated Muller cell characteristics.

LIST OF REFERENCES

1. Purves D, Augustine G J, Fitzpatrick D, et al., editors. Neuroscience. 2nd edition. Sunderland (MA): Sinauer Associates; 2001. Neuroglial Cells.
2. Allen N J, Lyons D A. Glia as architects of central nervous system formation and function. Science. 2018 Oct. 12; 362 (6411): 181-185.
3. Lee K M, MacLean A G. New advances on glial activation in health and disease. World J Virol. 2015 May 12; 4 (2): 42-55.
4. Lan X, Han X, Li Q, et al. Modulators of microglial activation and polarization after intracerebral haemorrhage. Nat Rev Neurol. 2017 July; 13 (7): 420-433.
5. Timmerman R, Burm S M, Bajramovic J J. An Overview of in vitro Methods to Study Microglia. Front. Cell. Neurosci. 2018 Aug. 6; 12 (242): 1-12.
6. Salter M W, Stevens B. Microglia emerge as central players in brain disease. Nat Med. 2017 Sep. 8; 23 (9): 1018-1027XXX.
7. D. J. Abraham et al. (2010) "Burger's Medicinal Chemistry, Drug Discovery and Development" Wiley, 7th Edition.
8. T. L. Lemke et al. (2013) "Foye's Principles of Medicinal Chemistry" Wiley, 7th Edition.
9. M. B. Smith (2013) "March's Advanced Organic Chemistry: Reactions, Mechanisms, and Structure" Wiley, 7th Edition.
10. S. Hanessian et al. (2013) "Design and Strategy in Organic Synthesis" Wiley-VCH, 1st Edition.
11. P. G. M. Wuts et al. "Greene's Protective Groups in Organic Synthesis" Wiley-Interscience, 4th Edition.
12. T. L. Ho "Fiesers' Reagents for Organic Synthesis" Wiley, Volume 27 Edition.
13. Blicke, F. F. (2011). "The Mannich Reaction". Organic Reactions. 1 (10): 303-341.

What is claimed is:

1. A method for the inhibition of glial cell activation in a human subject in need thereof comprising administering an effective amount of a compound of Formula 1, or a pharmaceutically acceptable salt, or ester, thereof optionally in association with a pharmaceutically acceptable adjuvant, diluent, or carrier Formula 1

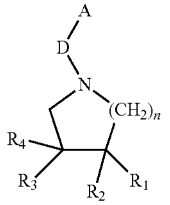

wherein:

A is selected from 2,3-dihydro-1,4-benzodioxin-6-yl, 1,4-benzodioxin-6-yl, 2,3-dihydro-1,4-benzoxathiin-6-yl, 2,3-dihydro-1,4-benzoxathiin-6-yl, 1,4-benzoxathiin-6-yl, 1,4-benzoxathiin-6-yl, 7-(yl)chroman-4-one, 6-(yl)chroman-4-one, 7-(yl)chromen-4-one, 7-(yl) chromen-4-one, 2,3-dihydrobenzo[g][1,4]benzodioxin-7-yl, benzo[g][1,4]benzodioxin-7-yl, 2,3-dihydrobenzo [g][1,4]benzoxathiin-7-yl, 2,3-dihydrobenzo[g][1,4] benzoxathiin-8-yl, benzo[g][1,4]benzoxathiin-7-yl, benzo[g][1,4]benzoxathiin-8-yl, 8-(yl)2,3-dihydrobenzo[g]chromen-4-one, 7-(yl)2,3-dihydrobenzo[g] chromen-4-one, 8-(yl)benzo[g]chromen-4-one, 7-(yl) benzo[g]chromen-4-one, each of which may be optionally substituted;

D is selected from $COCH_2$, $COCH_2CH_2$, $COCH_2CH_2CH_2$, $CH_2COCH_2CH_2$, $CHOHCH_2CH_2$, $COCHCH$, $COCH_2CH(CH_3)$, $COCHC(CH_3)$, $COCH_2CO$, $COSCH_2CH_2$, $COSCOCH_2$, $COOCH_2CH_2$, $CONHCH_2CH_2$, $COCH_2COCH_2$, $COCOCH_2$, $CHSCOCH_2$, $COCOCH_2CH_2$, $SO_2CH_2CH_2$, $SO_2CH_2CH_2CH_2$, $SO_2CH_2CH(CH_3)$, $SO_2CHC(CH_3)$, $SO_2CH_2COCH_2$, $CH_2COCH_2CH_2$, $COC_6H_4CH_2$, $C_6H_4COCH_2CH_2$, $C_6H_4COCH_2$, $COCH_2C_6H_4$, $COOCH_2C_6H_4$, $COSCH_2C_6H_4$, $COC_5NH_3CH_2$, $C_5NH_3COCH_2CH_2$, $C_5NH_3COCH_2$, $COCH_2C_5NH_3$, $COOCH_2C_5NH_3$, $COSCH_2C_5NH_3$, $CH_2NHCOCH_2CH_2$, $CH_2CH(OH)CH_2CH_2$;

n is 1;

$R_1$, $R_2$, $R_3$, and $R_4$ are independently selected from H, OH, F, Cl, Br, I, (halogen)alkyl, optionally substituted $C_1$ to $C_8$ straight chain or branched chain alkyl, optionally substituted $C_1$ to $C_8$ cycloalkyl, heterocycloalkyl, alkylheterocycloalkyl, optionally substituted $C_1$ to $C_8$ alkenyl, optionally substituted $C_1$ to $C_8$ alkynyl, optionally substituted aryl, optionally substituted alkylaryl, optionally substituted heteroaryl, optionally substituted alkylheteroaryl, O-alkyl, O-optionally substituted alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen)alkyl, wherein adjacent substituents $R_1$ and $R_3$, $R_2$ and $R_4$, when present, may form a saturated or unsaturated 5 membered or 6-membered or 7 membered carbocyclic or heterocyclic ring;

wherein alkenyl, if present, may refer to one or more double bond and each double bond may independently be cis or trans, E or Z, a cis/trans mixture or an E/Z mixture and wherein if an asymmetric center is present or asymmetric centers are present the compound may be in the form of a racemic mixture, a single enantiomer, a diastereoisomeric mixture, an enantiomeric diastereomer, a meso compound, a pure epimer, or a mixture of epimers thereof and wherein a hydrogen, several hydrogens or all hydrogens may be replaced with deuterium, wherein inhibition of glial cell activation treats a treatment of a disease or disorder selected from the group consisting of Alzheimer's disease, Amyotrophic lateral sclerosis, Frontotemporal lobar dementia, Parkinson's disease, Prion diseases, Ataxia, Multiple system atrophy, Corticobasal degeneration, Guillain-Barre syndrome, Lewy body dementia, Multiple sclerosis, Motor neuron disease, Retinopathy, Spinocerebellar ataxia, Huntington's disease, Autism Spectrum Disorder, Attention Deficit Hyperactivity disorder, Fragile X syndrome, Bipolar disorder, Post-Traumatic Stress disorder, Schizophrenia, Diabetic neuropathy, Neuropathic pain, Neuromyelitis Optica spectrum disorder, Post-Traumatic Brain Injury syndrome, and epilepsy.

2. The method according to claim 1 further comprising administering a second compound selected from the group consisting of Non-steroidal anti-inflammatory drugs, Immunomodulatory agents, Anti-malarial agents, Antibiotics, Anti-TNF alpha agents, Anti-CD20 agents, Anti-compliment factor agents, Anti-diarrheal agents, Anti-depressants, Antipsychotics, Anti-fungal agents, Anti-helminthics, T lymphocyte activation inhibitors, Anti-IL-1 agents, Glucocorticoids, Anti-cytokine/chemokine antibodies, Anti-cytokine/chemokine/nucleic acid or peptide aptamers, Sex steroids and receptor modulators, Anti-cellular surface receptor antibodies directed against cell surface receptors, Anti-cellular surface receptor nucleic acid or peptide aptamers, Aminosalicylic acid derivatives, Anticholinergic agents, Adrenergic agonists, Cholinergic agonists, Corticosteroids, Antineoplastic chemotherapeutic agents, Phosphodiesterase inhibitors, Leukotriene pathway modulators, Monoclonal antibodies directed against human immunoglobulins, Adrenergic antagonists, Calcium channel antagonists, Dopamine agonists, Serotonin agonists, Dopamine antagonists, Serotonin antagonists, Monoamine reuptake inhibitors, Protease inhibitors, Histamine receptor antagonists, Proton pump inhibitors, HMG-COA reductase inhibitors, Retinoids, Histone deacetylase inhibitors, Janus kinase/signal transducer and activator of transcription (JAK/STAT) inhibitors, Angiotensin antagonists, Anti-hyperlipidemics, Anti-hyperglycemic agents, Weight loss agents, Anti-parkinsonism agents, Monoamine oxidase inhibitors, Neurosteroids, Pattern recognition receptor antagonists and inhibitors, and Purinergic receptor antagonists and inhibitors.

3. A method to simultaneously inhibit the production by glial cells of at least two biomarkers selected from the group consisting of CCL2, CCL5, CXCL10, IL-1beta, IL-6, INF-beta, TNF-alpha, and VEGF, under conditions that produce activation of glial cells, comprising administering to a patient in need thereof an effective amount of a compound of Formula 1, or a pharmaceutically acceptable salt, or ester, thereof optionally in association with a pharmaceutically acceptable adjuvant, diluent, or carrier Formula 1

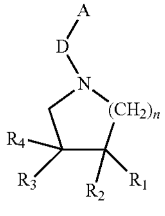

wherein:

A is selected from 2,3-dihydro-1,4-benzodioxin-6-yl, 1,4-benzodioxin-6-yl, 2,3-dihydro-1,4-benzoxathiin-6-yl, 2,3-dihydro-1,4-benzoxathiin-6-yl, 1,4-benzoxathiin-6-yl, 1,4-benzoxathiin-6-yl, 7-(yl)chroman-4-one, 6-(yl)chroman-4-one, 7-(yl)chromen-4-one, 7-(yl) chromen-4-one, 2,3-dihydrobenzo[g][1,4]benzodioxin-7-yl, benzo[g][1,4]benzodioxin-7-yl, 2,3-dihydrobenzo [g][1,4]benzoxathiin-7-yl, 2,3-dihydrobenzo[g][1,4] benzoxathiin-8-yl, benzo[g][1,4]benzoxathiin-7-yl, benzo[g][1,4]benzoxathiin-8-yl, 8-(yl)2,3-dihydrobenzo[g]chromen-4-one, 7-(yl)2,3-dihydrobenzo[g] chromen-4-one, 8-(yl)benzo[g]chromen-4-one, 7-(yl) benzo[g]chromen-4-one, each of which may be optionally substituted;

D is selected from $COCH_2$, $COCH_2CH_2$, $COCH_2CH_2CH_2$, $CH_2COCH_2CH_2$, $CHOHCH_2CH_2$, COCHCH, $COCH_2CH(CH_3)$, $COCHC(CH_3)$, $COCH_2CO$, $COSCH_2CH_2$, $COSCOCH_2$, $COOCH_2CH_2$, $CONHCH_2CH_2$, $COCH_2COCH_2$, $COCOCH_2$, $CHSCOCH_2$, $COCOCH_2CH_2$, $SO_2CH_2CH_2$, $SO_2CH_2CH_2CH_2$, $SO_2CH_2CH(CH_3)$, $SO_2CHC(CH_3)$, $SO_2CH_2COCH_2$, $CH_2COCH_2CH_2$, $COC_6H_4CH_2$, $C_6H_4COCH_2CH_2$, $C_6H_4COCH_2$, $COCH_2C_6H_4$, $COOCH_2C_6H_4$, $COSCH_2C_6H_4$, $COC_5NH_3CH_2$, $C_5NH_3COCH_2CH_2$, $C_5NH_3COCH_2$, $COCH_2C_5NH_3$, $COOCH_2C_5NH_3$, $COSCH_2C_5NH_3$, $CH_2NHCOCH_2CH_2$, $CH_2CH(OH)CH_2CH_2$;

n is 1;

$R_1$, $R_2$, $R_3$, and $R_4$ are independently selected from H, OH, F, Cl, Br, I, (halogen)alkyl, optionally substituted $C_1$ to $C_8$ straight chain or branched chain alkyl, optionally substituted $C_1$ to $C_8$ cycloalkyl, heterocycloalkyl, alkylheterocycloalkyl, optionally substituted $C_1$ to $C_8$ alkenyl, optionally substituted $C_1$ to $C_8$ alkynyl, optionally substituted aryl, optionally substituted alkylaryl, optionally substituted heteroaryl, optionally substituted alkylheteroaryl, O-alkyl, O-optionally substituted alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen)alkyl, wherein adjacent substituents $R_1$ and $R_3$, $R_2$ and $R_4$, when present, may form a saturated or unsaturated 5 membered or 6-membered or 7 membered carbocyclic or heterocyclic ring;

wherein alkenyl, if present, may refer to one or more double bond and each double bond may independently be cis or trans, E or Z, a cis/trans mixture or an E/Z mixture and wherein if an asymmetric center is present or asymmetric centers are present the compound may be in the form of a racemic mixture, a single enantiomer, a diastereoisomeric mixture, an enantiomeric diastereomer, a meso compound, a pure epimer, or a mixture of epimers thereof and wherein a hydrogen, several hydrogens or all hydrogens may be replaced with deuterium.

4. The method according to claim 3, wherein production of biomarkers CCL2, IL-1beta, IL-6, TNF-alpha and VEGF are simultaneously inhibited.

5. The method according to claim 3, wherein production of biomarkers CCL5, CXCL10, INF-beta, and TNF-alpha are simultaneously inhibited.

6. The method according to claim 3, wherein production of biomarkers CCL2, IL-6, and TNF-alpha are simultaneously inhibited.

7. The method according to claim 1, wherein the compound is selected from compounds 1-30, compounds 31-60, compounds 61-90, compounds 91-120, compounds 121-144, compounds 145-168, compounds 169-192, compounds 193-217, compounds 218-240, or compounds 241-264.

8. The method according to claim 1, wherein the compound is selected from compounds 265-288, compounds 289-312, compounds 313-336, compounds 337-360, compounds 361-384, compounds 385-408, compounds 409-437, compounds 438-465, compounds 466-494, or compounds 495-521.

9. A compound according to Formula 1

Formula I

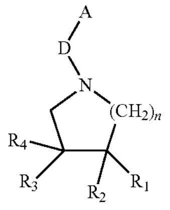

wherein:

A is selected from 2,3-dihydro-1,4-benzodioxin-6-yl, 1,4-benzodioxin-6-yl, 2,3-dihydro-1,4-benzoxathiin-6-yl, 2,3-dihydro-1,4-benzoxathiin-6-yl, 1,4-benzoxathiin-6-yl, 1,4-benzoxathiin-6-yl, 7-(yl) chroman-4-one, 6-(yl) chroman-4-one, 7-(yl) chromen-4-one, 7-(yl) chromen-4-one, 2,3-dihydrobenzo [g][1,4]benzodioxin-7-yl, benzo [g][1,4]benzodioxin-7-yl, 2,3-dihydrobenzo [g][1,4]benzoxathiin-7-yl, 2,3-dihydrobenzo [g][1,4]benzoxathiin-8-yl, benzo [g][1,4]benzoxathiin-7-yl, benzo [g][1,4]benzoxathiin-8-yl, 8-(yl) 2,3-dihydrobenzo [g]chromen-4-one, 7-(yl) 2,3-dihydrobenzo [g]chromen-4-one, 8-(yl) benzo [g]chromen-4-one, 7-(yl) benzo [g]chromen-4-one, each of which may be optionally substituted;

D is selected from $COCH_2$, $COCH_2CH_2$, $COCH_2CH_2CH_2$, $CH_2COCH_2CH_2$, $CHOHCH_2CH_2$, COCHCH, $COCH_2CH(CH_3)$, $COCHC(CH_3)$, $COCH_2CO$, $COSCH_2CH_2$, $COSCOCH_2$, $COOCH_2CH_2$, $CONHCH_2CH_2$, $COCH_2COCH_2$, $COCOCH_2$, $CHSCOCH_2$, $COCOCH_2CH_2$, $SO_2CH_2CH_2$, $SO_2CH_2CH_2CH_2$, $SO_2CH_2CH(CH_3)$, $SO_2CHC(CH_3)$, $SO_2CH_2COCH_2$, $CH_2COCH_2CH_2$, $COC_6H_4CH_2$, $C_6H_4COCH_2CH_2$, $C_6H_4COCH_2$, $COCH_2C_6H_4$, $COOCH_2C_6H_4$, $COSCH_2C_6H_4$, $COC_5NH_3CH_2$, $C_5NH_3COCH_2CH_2$, $C_5NH_3COCH_2$, $COCH_2C_5NH_3$, $COOCH_2C_5NH_3$, $COSCH_2C_5NH_3$, $CH_2NHCOCH_2CH_2$, $CH_2CH(OH)$ $CH_2CH_2$;

nis 1;

$R_1$, $R_2$, $R_3$, and $R_4$ are independently selected from H, OH, F, CI, Br, I, (halogen)alkyl, optionally substituted $C_1$ to $C_8$ straight chain or branched chain alkyl, optionally substituted $C_1$ to $C_8$ cycloalkyl, heterocycloalkyl, alkylheterocycloalkyl, optionally substituted $C_1$ to $C_8$ alkenyl, optionally substituted $C_1$ to $C_8$ alkynyl, optionally substituted aryl, optionally substituted alkylaryl, optionally substituted heteroaryl, optionally substituted alkylheteroaryl, O-alkyl, O-optionally substituted alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen) alkyl, wherein adjacent substituents $R_1$ and $R_3$, $R_2$ and $R_4$, when present, may form a saturated or unsaturated 5 membered or 6-membered or 7 membered carbocyclic or heterocyclic ring;

wherein alkenyl, if present, may refer to one or more double bond and each double bond may independently be cis or trans, E or Z, a cis/trans mixture or an E/Z mixture and wherein if an asymmetric center is present or asymmetric centers are present the compound may be in the form of a racemic mixture, a single enantiomer, a diastereoisomeric mixture, an enantiomeric diastereomer, a meso compound, a pure epimer, or a mixture of epimers thereof and wherein a hydrogen, several hydrogens or all hydrogens may be replaced with deuterium, wherein the compound is selected from compounds 2-521;

or a pharmaceutically acceptable salt, or ester thereof.

10. A pharmaceutical composition comprising a compound according to claim 9 and a pharmaceutically acceptable adjuvant, diluent, and/or carrier.

11. The pharmaceutical composition according to claim 10 in the form of a tablet, capsule, granule, powder, gel, caplet, troche, sachet, cachet, pouch, gum, sprinkle, liquid solution, suspension, or buccal and gastro-retentive preparation.

12. A pharmaceutical composition combination comprising a therapeutically effective amount of a composition comprising:

(a) a first compound according to claim 9; and (b) a second compound selected from the group consisting of Non-steroidal anti-inflammatory drugs, Immunomodulatory agents, Anti-malarial agents, Antibiotics, Anti-TNF alpha agents, Anti-CD20 agents, Anti-compliment factor agents, Anti-diarrheal agents, Anti-depressants, Antipsychotics, Anti-fungal agents, Anti-helminthics, T lymphocyte activation inhibitors, Anti-IL-1 agents, Glucocorticoids, Anti-cytokine/chemokine antibodies, Anti-cytokine/chemokine/nucleic acid or peptide aptamers, Sex steroids and receptor modulators, Anti-cellular surface receptor antibodies directed against cell surface receptors, Anti-cellular surface receptor nucleic acid or peptide aptamers, Aminosalicylic acid derivatives, Anticholinergic agents, Adrenergic agonists, Cholinergic agonists, Corticosteroids, Antineoplastic chemotherapeutic agents, Phosphodiesterase inhibitors, Leukotriene pathway modulators, Monoclonal antibodies directed against human immunoglobulins, Adrenergic antagonists, Calcium channel antagonists, Dopamine agonists, Serotonin agonists, Dopamine antagonists, Serotonin antagonists, Monoamine reuptake inhibitors, Protease inhibitors, Histamine receptor antagonists, Proton pump inhibitors, HMG-CoA reductase inhibitors, Retinoids, Histone deacetylase inhibitors, Janus kinase/signal transducer and activator of transcription (JAK/STAT) inhibitors, Angiotensin antagonists, Anti-hyperlipidemics, Anti-hyperglycemic agents, Weight loss agents, Anti-parkinsonism agents, Monoamine oxidase inhibitors, Neurosteroids, Pattern recognition receptor antagonists and inhibitors, and Purinergic receptor antagonists and inhibitors.

13. The pharmaceutical composition combination according to claim 12 in the form of a tablet, capsule, granule, powder, gel, caplet, troche, sachet, cachet, pouch, gum, sprinkle, liquid solution, suspension, or buccal and gastro-retentive preparation.

* * * * *